(12) United States Patent
Gellerman

(10) Patent No.: US 10,478,507 B2
(45) Date of Patent: Nov. 19, 2019

(54) PEPTIDE-BASED MULTIPLE-DRUG DELIVERY VEHICLE

(71) Applicant: Ariel-University Research and Development Company Ltd., Ariel (IL)

(72) Inventor: Gary Gellerman, Rishon-LeZion (IL)

(73) Assignee: Ariel-University Research and Development Company Ltd., Ariel (IL)

( * ) Notice: Subject to any disclaimer, the term of this patent is extended or adjusted under 35 U.S.C. 154(b) by 0 days.

(21) Appl. No.: 15/752,909

(22) PCT Filed: Oct. 18, 2016

(86) PCT No.: PCT/IL2016/051127
§ 371 (c)(1),
(2) Date: Feb. 15, 2018

(87) PCT Pub. No.: WO2017/068577
PCT Pub. Date: Apr. 27, 2017

(65) Prior Publication Data
US 2018/0250414 A1  Sep. 6, 2018

Related U.S. Application Data

(60) Provisional application No. 62/243,084, filed on Oct. 18, 2015.

(51) Int. Cl.
*C07K 1/107* (2006.01)
*C07K 1/113* (2006.01)
*A61K 47/64* (2017.01)
*A61K 47/65* (2017.01)
*C07K 2/00* (2006.01)
*A61K 38/00* (2006.01)

(52) U.S. Cl.
CPC ............ *A61K 47/641* (2017.08); *A61K 47/64* (2017.08); *A61K 47/65* (2017.08); *C07K 1/1077* (2013.01); *C07K 1/113* (2013.01); *C07K 2/00* (2013.01); *A61K 38/00* (2013.01); *Y02A 50/411* (2018.01)

(58) Field of Classification Search
CPC ...... A61K 47/62; A61K 47/641; C07K 1/006; C07K 1/1077; C07K 1/113
See application file for complete search history.

(56) References Cited

U.S. PATENT DOCUMENTS

8,524,663 B2 * 9/2013 Kirshenbaum ...... A61K 47/641
                                                      514/9.7
8,658,149 B2   2/2014 Satchi-Fainaro et al.
(Continued)

FOREIGN PATENT DOCUMENTS

WO   WO 03/079972   10/2003
WO   WO 2017/068577   4/2017

OTHER PUBLICATIONS

International Preliminary Report on Patentability dated May 3, 2018 From the International Bureau of WIPO Re. Application No. PCT/IL2016/051127. (8 Pages).
(Continued)

*Primary Examiner* — Jeffrey E. Russel

(57) ABSTRACT

A molecular structure comprising a targeting moiety, a multi-functional peptide platform and a plurality of controllably released bioactive agents attached thereto is provided herein.

3 Claims, 18 Drawing Sheets

(56) References Cited

U.S. PATENT DOCUMENTS

| | | |
|---|---|---|
| 2002/0071843 A1 | 6/2002 | Li et al. |
| 2004/0228831 A1 | 11/2004 | Belinka, Jr. et al. |
| 2012/0122779 A1 | 5/2012 | Kirshenbaum et al. |
| 2014/0079638 A1 | 3/2014 | Satchi-Fainaro et al. |
| 2015/0017115 A1 | 1/2015 | Satchi-Fainaro et al. |

OTHER PUBLICATIONS

International Search Report and the Written Opinion dated Jan. 23, 2017 From the International Searching Authority Re. Application No. PCT/IL2016/051127. (12 Pages).

Arap et al. "Cancer Treatment by Targeted Drug Delivery to Tumor Vasculature in a Mouse Model", Science, New Series, 279(5349): 377-380, Jan. 16, 1998.

Chen et al. "Synthesis and Biological Evaluation of Dimeric RGD Peptide-Paclitaxel Conjugate as a Model for Integrin-Targeted Drug Delivery", Journal of Medicinal Chemistry, 48(4): 1098-1106, Published on Web Jan. 27, 2005.

Ducry et al. "Antibody—Drug Conjugates: Linking Cytotoxic Payloads to Monoclonal Antibodies", Bioconjugate Chemistry, 21(1): 5-13, Published on Web Sep. 21, 2009.

Engel et al. "Targeted Therapy of Breast and Gynecological Cancers with Cytotoxic Analogues of Peptide Hormones", Molecular Pharmaceutics, 4(5): 652-658, Published on Web Aug. 18, 2007.

Falb et al. "In Situ Generation of Fmoc-Amino Acid Chlorides Using Bis-(Trichloromethyl)Carbonate and Its Utilization for Difficult Couplings in Solid-Phase Peptide Synthesis", The Journal of Peptide Research, 53(5): 507-517, May 1999.

Gazal et al. "Synthesis of Novel Protected N[Alpha](0mega-Thioalkyl) Amino Acid Buildings Units and Their Incorporation in Backbone Cyclic Disulfide and Thioetheric Bridged Peptides", Journal of Peptide Research, 58(6): 527-539, Dec. 2001.

Gellerman et al. "Facile Synthesis of Orthogonally Protected Amino Acid Building Blocks for Combinatorial N-Backbone Cyclic Peptide Chemistry", Journal of Peptide Research, 57(4): 277-291, Apr. 2001.

Gilad et al. "'Switch Off/Switch on' Regulation of Drug Cytotoxicity by Conjugation to a Cell Targeting Peptide", European Journal of Medicinal Chemistry, 85: 139-146, Available Online Jul. 22, 2014.

Gilad et al. "Synthesis, Biological Studies and Molecular Dynamics of New Anticancer RGD-Based Peptide Conjugates for Targeted Drug Delivery", Bioorganic & Medicinal Chemistry, 24(2): 294-303, Available Online Dec. 12, 2015.

Gilon et al. "A Backbone-Cyclic, Receptor 5-Selective Somatostatin Analogue: Synthesis, Bioactivity, and Nuclear Magnetic Resonance Conformational Analysis", the Journal of Medicinal Chemistry, 41(6): 919-929, Published on Web Feb. 24, 1998.

Goldshaid et al. "Novel Design Principles Enable Specific Targeting of Imaging and Therapeutic Agents to Necrotic Domains in Breast Tumors", Breast Cancer Research, 12(3): R29-1-R29-18, Published Online May 24, 2010.

Huang et al. "Targeting Delivery of Paclitaxel Into Tumor Cells Via Somatostatin Receptor Endocytosis", Chemistry & Biology, 7: 453-461, Jun. 9, 2000.

Kurzrock et al. "Safety, Pharmacokinetics, and Activity of GRN1005, A Novel Conjugate of Angiopep-2, A Peptide Facilitating Brain Penetration, and Paclitaxel, in Patients with Advanced Solid Tumors", Molecular Cancer Therapeutics, 11(2): 308-316, Published Online Dec. 27, 2011.

Leurs et al. "Design, Synthesis, In Vitro Stability and Cytostatic Effect of Multifunctional Anticancer Drug-Bioconjugates Containing GnRH-III as a Targeting Moiety", Peptide Science, 98(1): 1-10, Published Online Apr. 20, 2011.

Orban et al. "In Vitro Degradation and Antitumor Activity of Oxime Bond-Linked Daunorubicin-GnRH-III Bioconjugates and DNA-Binding Properties of Daunorubicin-Amino Acid Metabolites", Amino Acids, 41(2): 469-483, Published Online Oct. 16, 2010.

Ragozin et al. "Biolabile Peptidyl Delivery Systems Toward Sequential Drug Release", Peptide Science, 106(1): 119-132, Published Online Dec. 11, 2015.

Redko et al. "Synthesis, Drug Release, and Biological Evaluation of New Anticancer Drug-Bioconjugates Containing Somatostatin Backbone Cyclic analog as a Targeting Moiety", Peptide Science, 104(6): 743-752, Published Online Jun. 8, 2015.

Reubi et al. "Concomitant Expression of Several Peptide Receptors in Neuroendocrine Tumours: Molecular Basis for In Vivo Multireceptor Tumour Targeting", European Journal of Nuclear Medicine and Molecular Imaging, 30(5): 781-793, May 2003.

Schally et al. "Cancer Chemotherapy Based on Targeting of Cytotoxic Peptide Conjugates to Their Receptors on Tumors", European Journal of Endocrinology, 141(1): Jul. 1-14, 1999.

Schally et al. "Chemotherapy Targeted to Cancers Through Tumoral Hormone Receptors", Trends in Endocrinology and Metabolism, 15(7): 300-310, Available Online Jul. 31, 2004.

Sun et al. "Effects of Camptothecin Conjugated to a Somatostatin Analog Vector on Growth of Tumor Cell Lines in Culture and Related Tumors in Rodents", Drug Delivery, 11(4): 231-238, Jul.-Aug. 2004.

Sun et al. "Somatostatin Receptor-Targeted Anti-Cancer Therapy", Current Drug Delivery, 891): Jan. 2-10, 2011.

Sun et al. "Targeted Chemotherapy Using a Cytotoxic Somatostatin Conjugate to Inhibit Tumor Growth and Metastasis in Nude Mice", Clinical Medicine: Oncology, 2: 491-499, Published Online Aug. 19, 2008.

Szabo et al. "Development of an Oxime Bond Containing Daunorubicin-Gonadotropin-Releasing Hormone-III Conjugate as a Potential Anticancer Drug", Bioconjugate Chemistry, 20(4): 656-665, Published on Web Mar. 18, 2009.

Zhan et al. "Cyclic RGD Conjugated Poly(Ethylene Glycol)-Co-Poly(Lactic Acid) Micelle Enhances Paclitaxel Anti-Glioblastoma Effect", Journal of Controlled Release, 143: 136-142, Available Online Jan. 7, 2010.

Supplementary European Search Report and the European Search Opinion dated May 31, 2019 From the European Patent Office Re. Application No. 16857040.6. (7 Pages).

\* cited by examiner

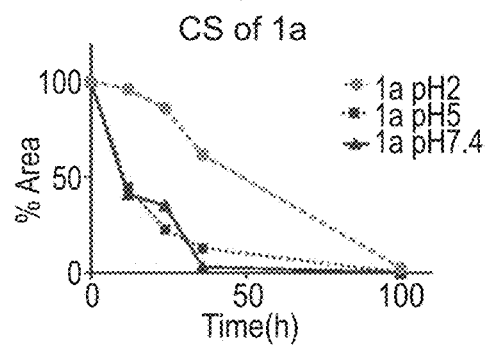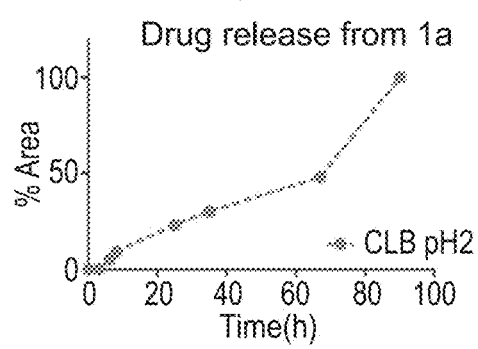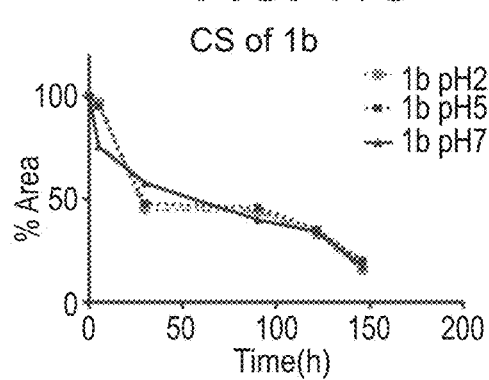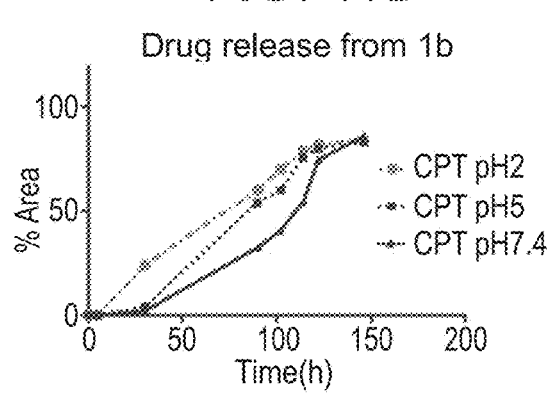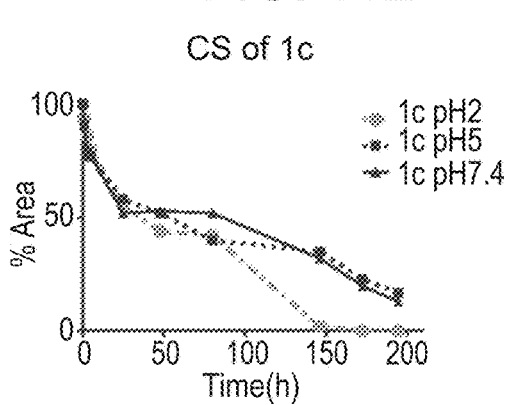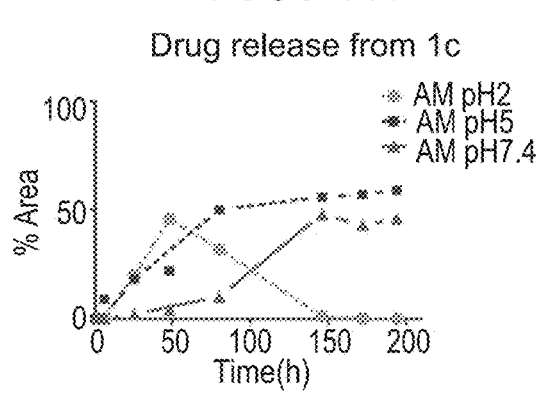

BS (LH) 1a

BS (LH) conjugate 1b

BS (LH) of 1c

BS (LH) of 1d

BS (LH) of 1e

24 h TRAMP C2

72 h TRAMP C2

PEPTIDE-BASED MULTIPLE-DRUG DELIVERY VEHICLE

RELATED APPLICATIONS

This application is a National Phase of PCT Patent Application No. PCT/IL2016/051127 having International filing date of Oct. 18, 2016, which claims the benefit of priority under 35 USC § 119(e) of U.S. Provisional Patent Application No. 62/243,084 filed on Oct. 18, 2015.

FIELD AND BACKGROUND OF THE INVENTION

The present invention, in some embodiments thereof, relates to pharmaceuticals, and more particularly, but not exclusively, to a molecular structure that acts as a multiple-drug delivery vehicle, and to uses thereof.

Delivery of drugs to medicinally targeted loci in a living organism has been for decades a challenging mission of many medical and chemical research endeavors. An even more challenging task is the delivery of more than one type of drug to a target site, while another is the concerted and controlled targeted release of multiple drugs from a single carrier molecule. For example, targeting drugs by conjugation to a targeting moiety (also referred to herein interchangeably as a "carrier molecule", "carrier" and "biomolecular carrier") having a high affinity to specific receptors on cancer cells provides a solution for two major problems in anticancer therapy: the lack of target cell specificity of most anticancer drugs and improvement of their toxicology.

Attempts have been made to employ complex molecular structures to targeting moieties, mainly encapsulating structures, as well polymeric and dendrimers carrier structures. However, these attempts were aimed at, or generally achieved molecular structures that were capable of delivering either one type of drug in multiple copies, or release the drugs under one type of physiological condition and/or rate of release. Over the past decades, carrier-drug conjugates have been developed to target cell delivery of potent anticancer drugs with the aim of eliminating the morbidity-causing non-specific side effects common to conventional chemotherapy. Typically, the carriers are macromolecules such as monoclonal antibodies and other proteins, or smaller molecular carriers like polynucleotide segments and peptides. Despite advances in these areas, the carrier-drug conjugates reported so far are limited to carry one drug type, although drug conjugation chemistry is well elaborated.

Several recent publications presented biologically active peptide-drug conjugates, manifesting improvement of the drug-like features of the linked drugs. It has been demonstrated that bioconjugates containing the GnRH-III peptide can be used as a targeting moiety [Leurs, U. et al., Peptide Sci, 2011, 98, 1-10], and the chemotherapeutic agent daunorubicin has been demonstrated as drug delivery systems for targeted cancer chemotherapy [Organ, E. et al., Amino Acids, 2010, DOI: 10.1007/s00726-010-0766-1; and Szabo, I. et al., Bioconjug Chem, 2009, 20, 656-665]. Selective accumulation and prolonged retention of the RGD analog c(RGDfK), linked to fluorescent bacteriochlorophyll derivative, has been reported in the tumor necrotic domain in MDA-MB-231-RFP bearing mice, which enabled early detection of tumor growth and foster prognosis and the development of novel modes of treatment [Goldshaid, L. et al., Breast Cancer Res, 2010, 12, R29].

The most clinically studied peptide-drug-conjugate is GRN1005, an angiopeptin-2-paclitaxol conjugate that targets lipoprotein receptor protein-1, a cell surface molecule overexpressed on solid tumor cells. This conjugate is under clinical assessment for treatment of advanced solid tumors, in particular in patients with brain metastases [Kurzrock, R. et al., Mol Canc Ther, 2012, 11, 308-316]. Potent luteinizing hormone releasing hormone (LHRH) antagonists, were used as targeting moieties for a variety of cancer drugs, including doxorubicin and its analogs, and studies on conjugates of [D-Lys6]-LHRH-DOX and [D-Lys6]-LHRH-2-pyrrolino-DOX showed increased efficacy of the drug as the LHRH analog maintained its highly targeted binding affinity while the drug retained its cytotoxic effects on the tumor cells [Schally, A. V. and Nagy, A., Eur J Endocrinol, 1999, 141, 1-14].

Another cell-surface receptor family, G protein-coupled somatostatin receptors (SSTRs), have drawn the attention of medicinal chemists as promising targets for TDD by conjugates based on SSTR specific peptide ligand conjugates [Sun, L. C. et al., Curr Drug Del, 2011, 8, 2-10]. The expression of SSTRs in peritumoral veins is a general phenomenon in blood vessels of many tumors [Reubi, J. C. et al., Eur J Nucl Med Mol Imaging, 2003, 30, 781-793].

The aberrant expression of SSTRs in various tumors and angiogenic tumor vessels, offers an additional opportunity for cancer patients to be treated with SST- or analog-based receptor-specific cancer therapy. After binding to their receptors, SST and its analogs are rapidly internalized into the cells and may even translocate to the cell nucleus. This may reduce the side effects of MDR often observed with traditional chemotherapy. Notably, due to the preferential expression of SSTR2 in many tumors and tumoral blood vessels when compared to other SSTR subtypes, most of these SST conjugates have been designed to target SSTR2-specific sites. Several delivery systems based on SST analogs have been reported. JF-10-81, a camptothecin-SSTR2 conjugate, was prepared by directly coupling camptothecin (CPT) to the N-terminus of an S—S bridged octapeptide SST analog via the cleavable carbamate group and a basic N-terminal linking motif [Sun, L. et al., Drug Deliv, 2004, 11, 231-238]. This conjugate had potent inhibitory activity against various human tumors in vivo, including neuroblastoma IMR32, pancreatic cancer CFPAC-1, pancreatic carcinoid BON, prostate cancer PC-3, leukemia MOLT-4, small cell lung cancer NCI-H69 and rat pancreatic cancer CA-20948 [Sun, L. et al., Clin Med Oncol, 2008, 2, 491-499]. Paclitaxel (PTX, taxol), which targets tubulin and leads to the inhibition of cell division, was conjugated to the N-terminal of the octapeptide SST analog octreotide [Huang, C. M. et al., Chem Biol, 2000, 7, 453-461]. This conjugate retained the cell-selective binding of octreotide and the biological activity of PTX, and appeared to be exclusively cytotoxic to breast cancer MCF-7 cells highly expressing SSTR2. The potent cytotoxin doxorubicin (DOX) was conjugated to SSTR2-specific octapeptide SST analog to produce a cytotoxic DOX-SST conjugate AN-238 [Engel, J. B. et al., Mol Pharm, 2007, 4, 652-658]. This anticancer drug conjugate displayed significant anti-tumor activities and reduced toxicity against various cancers such as ovarian, endometrial breast, prostate, pancreatic, renal cell cancers, hepatoma, melanoma, lymphoma, small cell lung cancer (SCLC) and glioblastoma [Schally, A. V. et al., Trends Endocrinol Metab, 2004, 15, 300-310; Schally, A. V. et al., Eur J Endocrinol, 1999, 141, 1-14.]. In addition, AN-238 was reported to overcome multi-drug resistance resulting from conventional chemotherapy [Enge, J. B. et al., Endocr Relat Cancer, 2005, 12, 999-1009].

The chemistry of carrier-drug attachment has received much attention. Main parameters include selection of a linker attachment site that retains carrier activity, linker length and composition, and the design of drug analogs for attachment to the linker. In an exemplary case of antibody-drug conjugates (ADC), two methods are now commonly used for conjugating drugs to antibodies: alkylation of reduced inter chain cysteine disulfides through a non-cleavable maleimido linker and acylation of lysine residues by cleavable linear amino acids. Cathepsin-cleavable linkers are also utilized (for example Val-Cit, or Phe-Lys) bound to self-emulative moiety PABA (p-aminobenzyl alcohol), enabling selective drug release in cancer cells. Spacers are usually essential extensions of the drug linkage and are responsible for avoiding the shielding of the active site of the antibody as well as improving solubility properties of ADCs (for example by the use of polyethylene glycol).

Carrier-drug conjugates have been successfully demonstrated and employed for the targeted delivery of drugs and toxins to receptor-positive murine leukemic cells. In particular, the use of multifunctional dendrone linkers that bear several covalently bound DNA alkylating chlorambucil (Leukeran) molecules to one peptide carrier have enhanced efficacy of growth inhibition of targeted cancer cells.

Ducry, L. et al., [*Bioconjugate Chem.*, 2010, 21, pp. 5-13] present antibody-drug conjugates (ADCs) that combine the specificity of monoclonal antibodies (mAbs) with the potency of cytotoxic molecules.

U.S. Pat. No. 5,714,166 relates to a dendrimer coupled to at least one bioactive agent, particularly the agent being a biological response modifier. U.S. Pat. No. 5,830,986 provides a method for synthesizing a dendrimer based on polyethylene oxide for binding a biologically active molecule. U.S. Pat. No. 6,020,457 teaches dendritic polymers for drug delivery, containing a disulfide moiety in the core. U.S. Patent Application No. 2002/0071843 relates to a targeting therapeutic agent comprising a targeting entity which binds to a site of pathology, a linking factor, such as a dendrimer, and a therapeutic entity, the factor eventually binding additional materials. U.S. Patent Application No. 2003/0180250 provides a dendrimer complexed with an anti-inflammatory drug. WO 2004/019993 discloses a self-immolative dendrimer that releases many active moieties upon interacting with a single activating event. U.S. Patent Application No. 2004/0228831 describes a polymeric drug conjugate comprising one or more biologically active agents linked via an enzymatically cleavable linker, for targeting a diseased tissue.

WO 2008/047345 teaches a multifunctional platform for covalent binding of at least two different therapeutic or diagnostic agents and for their sequential release at a target site in a biological environment.

Gilad, Y et al. [*Eur J Med Chem.*, 2014, 85, pp. 139-46] each an amino acid-based platform loaded with one or two drugs for conjugation to a peptide targeting moiety.

Additional background art include U.S. Pat. Nos. 8,703,114 and 9,050,370, U.S. Patent Application Nos. 20150017115 and 20140271483, and WO 2014/203189.

All documents cited herein are hereby incorporated by reference.

SUMMARY OF THE INVENTION

According to an aspect of some embodiments of the present invention, there is provided a molecular structure represented by Formula I:

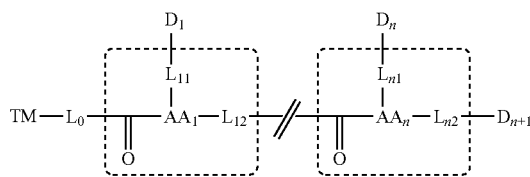

Formula I wherein:

$AA_1$ and $AA_n$ are each independently an amino acid residue;

n is an integer equal or larger than 2 and denoting a number of the amino acid residues in the structure;

TM is a targeting moiety;

$L_0$, $L_{11}$, $L_{12}$, $L_{n1}$ and $L_{n2}$ are each independently a linking moiety;

$D_1$, $D_n$ and $D_{n+1}$ are each independently a bioactive agent or absent, provided that at least two of $D_1$, $D_n$ and $D_{n+1}$ are each independently a bioactive agent.

In some embodiments, $D_1$, $D_n$ and $D_{n+1}$ are each independently a bioactive agent.

In some embodiments, each of the $D_1$, $D_n$ and $D_{n+1}$ is the same bioactive agent.

In some embodiments, at least one bioactive agent of the $D_1$, $D_n$ and $D_{n+1}$ is different than at least one other bioactive agent of the $D_1$, $D_n$ and $D_{n+1}$.

In some embodiments, each of the $D_1$, $D_n$ and $D_{n+1}$ is different.

In some embodiments, the mechanism of biological activity of each of the $D_1$, $D_n$ and $D_{n+1}$ is the same.

In some embodiments, the mechanism of biological activity of at least one bioactive agent of the $D_1$, $D_n$ and $D_{n+1}$ is different than a mechanism of biological activity of at least one other bioactive agent of the $D_1$, $D_n$ and $D_{n+1}$.

In some embodiments, the mechanism of biological activity of each of the $D_1$, $D_n$ and $D_{n+1}$ is the different.

In some embodiments, each of the $D_1$, $D_n$ and $D_{n+1}$ is characterized by at least one ADME-Tox parameter, and the parameter of at least one of the $D_1$, $D_n$ and $D_{n+1}$ is different than the parameter of others of the $D_1$, $D_n$ and $D_{n+1}$.

In some embodiments, each of the $L_{11}$ and $L_{n1}$ is a liable linking moiety.

In some embodiments, each of the $L_{11}$ and $Ln_1$ is characterized by a cleavage condition, and the condition of at least one of the $L_{11}$ and $Ln_1$ is different than a cleavage condition of others of the $L_{11}$ and $Ln_1$.

In some embodiments, each of the $L_{12}$ and $L_{n2}$ is a peptide bond (amide).

In some embodiments, $D_1$, $D_n$ and $D_{n+1}$ are each independently selected from the group consisting of an anti-proliferative agent, an anti-cancer agent, a chemosensitizing agent, an anti-inflammatory agent, an antimicrobial agent, an anti-hypertensive agent and any combination thereof.

According to an aspect of some embodiments of the present invention, there is provided a pharmaceutical composition includes, the molecular structure presented herein as an active ingredient, and a pharmaceutically acceptable carrier.

In some embodiments, the pharmaceutical composition presented herein is packaged in a packaging material and identified in print, in or on the packaging material, for use in the treatment of a medical condition.

According to an aspect of some embodiments of the present invention, there is provided a use of the molecular structure presented herein, in the preparation of a medicament.

In some embodiments, the medicament is for treating a medical condition.

According to an aspect of some embodiments of the present invention, there is provided a method of treating a medical condition in a subject in need thereof, the method includes administering to the subject a therapeutically effective amount of the molecular structure presented herein or the pharmaceutical composition presented herein.

In some embodiments, the medical condition is selected from the group consisting of a microorganism infection, cancer, an autoimmune disease, a genetic disease, a degenerative disease, a psychiatric disease, a peptic ulcer disease, Alzheimer's disease, rheumatoid arthritis, post-traumatic stress disorder, Crohn's disease, tuberculosis, leprosy, malaria, and HIV/AIDS.

According to an aspect of some embodiments of the present invention, there is provided a process of preparing the molecular structure presented herein, the process includes:

binding a targeting moiety to a solid support;
linking a first amino acid to the targeting moiety;
attaching a first bioactive agent to the first amino acid;
linking a second amino acid to the first amino acid;
attaching a second bioactive agent to the second amino acid;
attaching a third bioactive agent to the second amino acid; and
detaching the targeting moiety from the solid support to thereby obtain the molecular structure.

In some embodiments, the process further includes, prior to attaching the third bioactive agent to the second amino acid:

linking a third amino acid to the second amino acid;
attaching a third bioactive agent to the third amino acid; and
attaching a fourth bioactive agent to the third amino acid.

In some embodiments, linking and/or attaching is effected via a functional group on the targeting moiety, or a functional group on a side chain, or on an alpha carbon of the amino acid.

In some embodiments, linking and/or attaching to the functional group further includes removing a protection group on the functional group.

As used herein the term "about" refers to ±10%.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIG. 11A-J present the results of the chemo-stability and drug release profiles assays, conducted for conjugates 1a-e at pH 2, 5 and 7.4. Degradation of 1a (FIG. 11A), 1b (FIG. 11C), 1c (FIG. 11E), 1d (FIG. 11G), 1e (FIG. 11I), and the release of the corresponding drugs: CLB (FIG. 11B), CPT (FIG. 11D), AM (FIG. 11F), ABT-751 (FIG. 11H), and COMB (FIG. 11J);

FIGS. 12A-E present the results of the bio-stability and drug release profiles assays conducted for conjugates 1a-e in LH, wherein FIG. 12A shows the results of the biostability assay of conjugate 1a and release of CLB, FIG. 12B shows the results of the biostability assay of conjugate 1b and release of CPT, FIG. 12C shows the results of the biostability assay of conjugate 1c and release of AM, FIG. 12D shows the results of the biostability assay of conjugate 1d and release of ABT-751, and FIG. 12E shows the results of the biostability assay of conjugate 1e and release of COMB;

FIG. 13B. H1299; FIG. 13C. TRAMP C2) against the SSTR2 low expression cell line (FIG. 13D) HEK as negative control;

FIGS. 19A-D present the results of the viability assay (% surviving cells) of the cell cultures calculated relative to the control, 100% viability. The significances of the results are shown by the corresponding p values, wherein FIG. 19A and FIG. 19B show the viability of treated TRAMP C2 cells after 24 h and 72 h, respectively, and FIG. 19C and FIG. 19D show the viability of HEK 293 cells after 24 h and 72 h, respectively.

DESCRIPTION OF EMBODIMENTS OF THE INVENTION

The present invention, in some embodiments thereof, relates to pharmaceuticals, and more particularly, but not exclusively, to a multiple-drug delivery vehicle, and to uses thereof.

Before explaining at least one embodiment of the invention in detail, it is to be understood that the invention is not necessarily limited in its application to the details set forth in the following description or exemplified by the Examples. The disclosure is meant to encompass other embodiments or of being practiced or carried out in various ways.

While conceiving the present invention, the present inventor envisioned a comprehensive therapeutic potential for carrier-drug molecular structures (referred to herein for short as "molecular structures") that consist of a targeting moiety (carrier) and several different drug molecules linked via biodegradable linking moieties to multifunctional amino acid platforms (MAAP) which is linked to a target specific carrier molecule.

Figure 1:
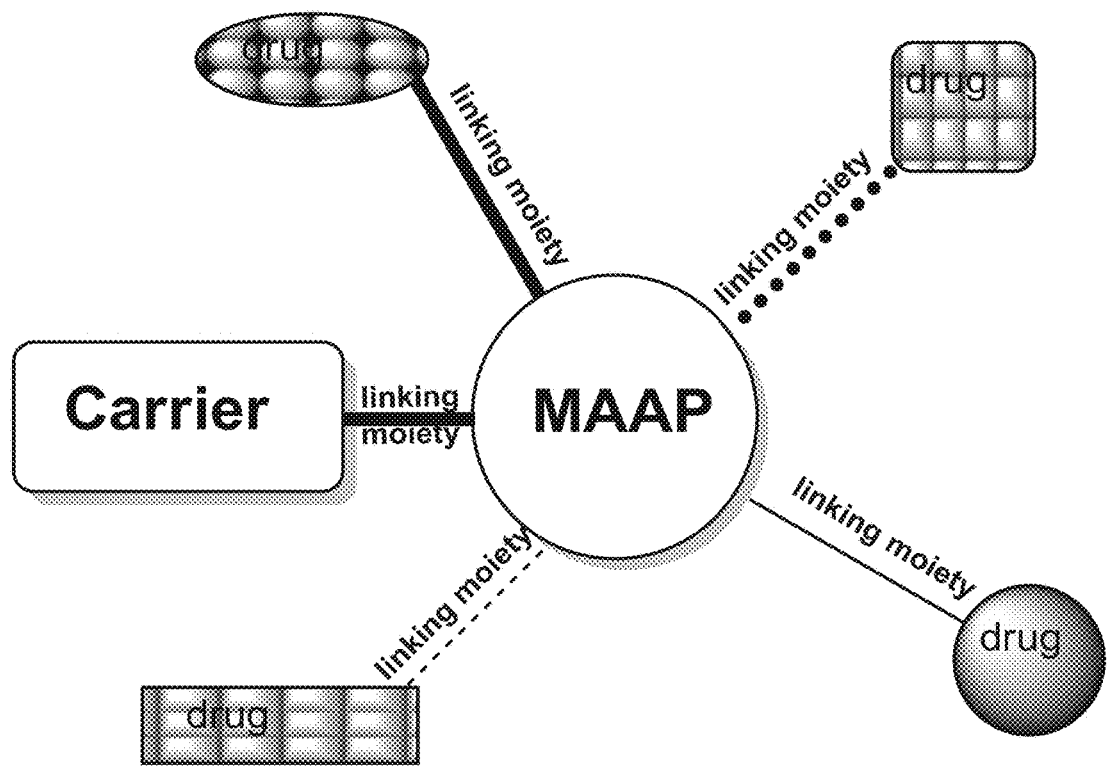
FIG. 1 presents a schematic illustration of a carrier-drug molecular structure, according to some embodiments of the invention.

FIG. 1 presents a schematic illustration of a carrier-drug molecular structure, according to some embodiments of the invention.

The linkage of several drugs to a single targeting moiety (also referred to herein interchangeably as a "carrier molecule" or "carrier") might further enhance their therapeutic efficacy, particularly if the molecular structure that carries the various drugs in designed for a pre-determined drug release profile. The drugs can be similar (multiple copies of the same drug), different in terms of chemical structure but similar in mechanism of action, or different in terms of both chemical structure and mechanism of action. Such molecular structures are designed to release the multiple-drug payload specifically at the targeted cells/tissue/organ/bodily-site and thereby avoid exposure of benign cells/tissue to the drug treatment. The release profile is controlled by the type of the biodegradable linking moieties, whereas a multiple copies of an identical drug can be released sequentially or simultaneously, or a series of different drugs can be released sequentially or simultaneously.

The rationale behind this concept is based on the following assumptions:

i) Targeting moieties can typically be linked to a short peptide having a relatively small number of amino acid (2-10);

ii) Amino acids are naturally occurring and thus are generally non-toxic;

iii) Prodrugs can be prepared with enzymatically cleavable linking moieties such as amides, esters, carbamates, carbonates and the like, thus various drugs can be linked to MAAPs through such enzymatically cleavable linking moieties;

iv) Drugs linked to amino acids via such enzymatically cleavable linking moieties can be cleaved enzymatically in vivo at a pre-selected targeted tissue/organ/ bodily site;

v) The release profile of each of the drugs depends, inter alia, on the nature of the linking moiety, the physiological environment (enzymes and other factors) and the drug molecule itself;

vi) The release profile can be controlled by selection and optimization of drug-linking parameters in the design of a drug-loaded MAAP; and vii) All the breakdown products of the MAAP.

The present inventor has contemplated that such MAAP technology, according to some embodiments of the present invention, can be integrated into the rational design and application of targeted drug delivery strategies and ultimately to a broader therapeutic spectrum of more effective therapies, such as cancer therapy.

While searching for a versatile molecular drug delivery vehicle for targeted delivery of multiple and varied bioactive agents, which is capable of releasing each of the bioactive agents under different physiological conditions (e.g., enzymatic cleavage), and further have a generally pharmaceutically acceptable components, the present inventor has designed a peptide, referred to herein as multifunctional amino acid platforms or MAAP, having two or more amino acid residues, wherein each amino acid residue is capable of carrying at least one of a wide range of bioactive agents, each attached thereto via one of a variety of cleavable linking moieties. By tethering the resulting MAAP to a targeting moiety, the preset inventor has accomplished a peptide-based molecular vehicle which can deliver a combination of drugs to a targeted locus (targeted bodily site), or a multiple copies of a drug which can be released interspersedly at the targeted locus, or a combination of drugs which can be released interspersedly at the targeted bodily site.

The presently disclosed molecular drug delivery vehicle comprises four general structural features: a peptide backbone, a targeting moiety, a plurality of bioactive agents and a plurality of linking moieties that connect between the peptide backbone and the targeting moiety, and connect between the peptide backbone and the bioactive agents. The nature of the amino acid which for the backbone is such that each can be identical or different, adding another way to affect the rate of release of the attached bioactive agents, which is further affected by the nature of the linking moieties themselves.

For example, in a molecular structure where n=2, the molecular structure is represented by the general formula:

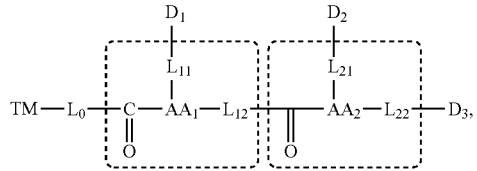

for n=3, the molecular structure is represented by the general formula:

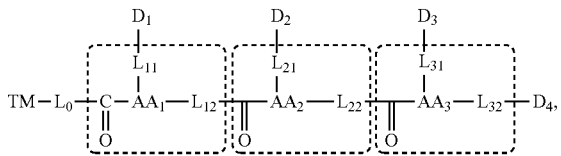

and for n=4, the molecular structure is represented by the general formula:

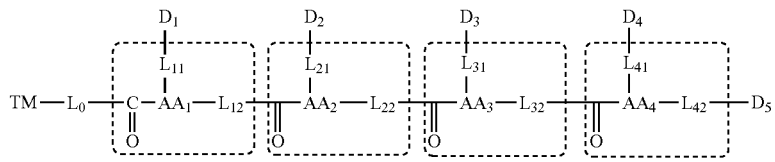

Hence, according to an aspect of some embodiments of the present invention, there is provided a molecular structure represented by general Formula I:

Formula I

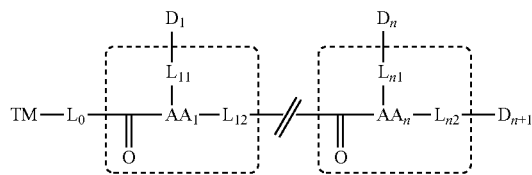

wherein:
the dashed envelope encompasses a repeating unit in the molecular structure;
the pair of slanted parallel lines denotes a continuous chain of repeating units in the molecular structure, wherein n is for example 2, 3, 4 and so on up to highest value for n;
n is an integer equal or larger than 2;
$AA_1$ and $AA_n$ are each independently an amino acid residue;
TM is a targeting moiety;
$L_0$, $L_{11}$, $L_{12}$, $L_{n1}$ and $L_{n2}$ are each independently a linking moiety; and
$D_1$, $D_n$ and $D_{n+1}$ are each independently a bioactive agent or absent, provided that at least two of $D_1$, $D_n$ and $D_{n+1}$ are each independently a bioactive agent.

The molecular structure represented by general Formula I is a peptide chain of two or more amino acid residues, wherein n=2, 3, 4 or more, according to the following exemplary structural representations.

The variable of "n" may also range higher than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50. In some embodiments of the present invention, n=2, 3, 4, 5, 6, 7, 8 or 9. In some embodiments, n=2-5.

For any of the embodiments described herein, the molecular structures described herein may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be a base addition salt comprising at least one acidic (e.g., phenol and/or carboxylic acid) group of the compound which is in a negatively charged form (e.g., wherein the acidic group is deprotonated), in combination with at least one counter-ion, derived from the selected base, that forms a pharmaceutically acceptable salt.

The base addition salts of the compounds described herein may therefore be complexes formed between one or more acidic groups of the drug and one or more equivalents of a base.

The base addition salts may include a variety of organic and inorganic counter-ions and bases, such as, but not limited to, sodium (e.g., by addition of NaOH), potassium (e.g., by addition of KOH), calcium (e.g., by addition of Ca(OH)$_2$, magnesium (e.g., by addition of Mg(OH)$_2$), aluminum (e.g., by addition of Al(OH)$_3$ and ammonium (e.g., by addition of ammonia). Each of these acid addition salts can be either a mono-addition salt or a poly-addition salt, as these terms are defined herein.

Depending on the stoichiometric proportions between the charged group(s) in the compound and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

Further, each of the compounds described herein, including the salts thereof, can be in a form of a solvate or a hydrate thereof.

The compounds described herein can be used as polymorphs and the present embodiments further encompass any isomorph of the compounds and any combination thereof.

The present embodiments further encompass any enantiomers and diastereomers of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

Amino Acid:

In some embodiments, each amino acid may be the same or different, and each amino acid forms a part of a single peptide chain (peptide). A single peptide may comprise a variety of amino acids or may comprise only one type of amino acid. In some embodiments, the single peptide comprises one or more amino acid residues.

As used herein throughout the term "amino acid" or "amino acids" is understood to include the 20 genetically coded amino acids selected from the group consisting of L- or D-glycyl, L- or D-alanyl, L- or D-valinyl, L- or D-leucyl, L- or D-isoleucyl, L- or D-threonyl, L- or D-seryl, L- or D-cysteinyl, L- or D-methionyl, L- or D-aspartyl, L- or Dglutamyl, L- or D-histidyl, L- or D-lysinyl, L- or D-asparagyl, L- or D-glutaminyl, L- or D-arginyl, L- or D-phenylalanyl, L- or D-tyrosyl, L- or D-tryptophyl, or L- or D-prolinyl; as well as those amino acids which are modified synthetically or post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids and other non-naturally occurring amino acids.

The term "amino acid residue" refers to the major moiety of an amino acid which forms a part of a larger molecular structure, such as a peptide, protein and the likes. For example, in a polypeptide chain, the amino acid residue of an amino acid comprises the alpha carbon and the side-chain as in the free amino acid, while the amine group and the carboxyl group each independently form a peptide bond (a linking moiety) with the neighboring amino acid residues.

Tables 1 and 2 below list the genetically encoded amino acids (Table 1) and non-limiting examples of non-conventional/modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |

TABLE 2-continued

| Non-conventional amino acid | Code | Non-conventional amino acid | Code |
|---|---|---|---|
| aminonorbornyl-carboxylate | Norb | L-N-methylglutamine | Nmgln |
|  |  | L-N-methylglutamic acid | Nmglu |
| Cyclohexylalanine | Chexa | L-N-methylhistidine | Nmhis |
| Cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D/L-ornithine | D/Lorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-☐-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methylα-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | ☐-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-☐-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methylα-napthylalanine | Nmanap |
| D-N-methylvaline | Dnmval | N-methylpenicillamine | Nmpen |
| ☐-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-☐-aminobutyrate | Nmgabu |
| N-methylcyclohexylalanine | Nmchex | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |

TABLE 2-continued

| Non-conventional amino acid | Code | Non-conventional amino acid | Code |
|---|---|---|---|
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| □-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
|  | Nnbhm | D/L-citrulline | D/Lctr |
| N-(N-(2,2-diphenylethyl)car-bamylmethyl-glycine | Nnbhm |  |  |
| 1-carboxy-1-(2,2-diphenyl ethylamino)cyclopropane | Nmbc |  |  |
| N-(N-(3,3-diphenylpropyl)car-bamylmethyl(1)glycine | Nnbhe |  |  |

According to some embodiments, amino acids that are suitable for forming a part of the molecular structure presented herein are those that exhibit at least one functional group in their side-chain. For example, a lysine residue exhibits an amino group at the end of its side-chain; a glutamic acid residue exhibits a carboxyl group at the end of its side-chain; and a cysteine residue exhibits a thiol group at the end of its side-chain. Following these non-limiting examples, each of the amino, carboxyl and thiol group can form the basis for a different linking moiety.

As used herein, the term "amino acid" refers to both an amino acid, alone (e.g., lysine), or an amino acid residue (e.g., lysyl). When two or more amino acids combine to form a peptide and the elements of water are removed, what remains of each amino acid may be called an "amino acid residue". Amino-acid residues are structures that lack a hydrogen atom of the amino group (—NH—C$_α$HR—C(=O)OH), or the hydroxyl moiety of the carboxyl group (NH$_2$—C$_α$HR—C(=O)—), or both (—NH—C$_α$HR—C(=O)—); all units of a peptide chain are therefore amino acid residues. Amino acids may terminate in —C(=O)OH, —C(=O)O(R), wherein R is a carboxylic acid protecting group, —C(=O)NHR$^1$, or —NHR$^2$, wherein R$^1$ and R$^2$ are each independently an H or amino protecting group.

As used herein, a "peptide" refers to two or more amino acids joined together by an amide bond, also referred to herein as a peptide bond. Peptides may terminate in any fashion described above regarding amino acids.

Amino acids can be linked to the targeting moiety, to one-another and/or to any one of the bioactive agents via the amino and/or carboxyl groups on the α-carbon thereof, and/or via a functional group on the side-chain thereof.

Examples of amino acids, which are useful in the context of the present invention, include, without limitation, lysine exhibiting an amino reactive group, threonine exhibiting a hydroxyl reactive group, aspartic acid exhibiting a carboxyl reactive group, ornithine exhibiting an amino reactive group, cysteine exhibiting a thiol reactive group, tyrosine exhibiting a hydroxyl reactive group, and glutamic acid exhibiting a carboxyl reactive group.

Linking Moiety:

As used herein, the term "moiety" describes portion of a molecule, and typically a major portion thereof, or a group of atoms pertaining to a specific function.

As used herein, the words "link", "linked", "linkage" "linker", "bound" or "attached", are used interchangeably herein and refer to the presence of at least one covalent bond between species, unless specifically noted otherwise.

As used herein, the term "linking moiety" describes a chemical moiety (a group of atoms or a covalent bond) that links two chemical moieties via one or more covalent bonds. A linking moiety may include atoms that form a part of one or both of the chemical moieties it links, and/or include atoms that do not form a part of one or both of the chemical moieties it links. For example, a peptide bond (amide) linking moiety that links two amino acids includes at least a nitrogen atom and a hydrogen atom from one amino acid and at least a carboxyl of the other amino acid. In general, the linking moiety can be formed during a chemical reaction, such that by reacting two or more reactive groups, the linking moiety is formed as a new chemical entity which can comprise a bond (between two atoms), or one or more bonded atoms. Alternatively, the linking moiety can be an independent chemical moiety comprising two or more reactive groups to which the reactive groups of other compounds can be attached, either directly or indirectly, as is detailed hereinunder.

The positions at which the bioactive agent is linked to the molecular structure presented herein are generally selected such that once cleaved off the molecular structure, any remaining moiety stemming from the linking moiety (or a spacer moiety) on the bioactive agent, if at all, does not substantially preclude its biological activity (mechanism of biological activity). Suitable positions depend on the type of bioactive agent. According to some embodiments of the present invention, the linking moieties are form such that the biological activity of the bioactive agent, once released from the molecular structure, is not abolished and remains substantially the same as the biological activity of a similar pristine bioactive agent.

In some embodiments, the term "linking moiety" encompasses an amino acid residue, or a peptide of two or more amino acids residues. In such embodiments, the molecular structure may be regarded as one that comprises one or more amino acid residues that do not bear a bioactive agent.

In some embodiments, the term "linking moiety" is defined so as not to encompass an amino acid residue or a peptide. In such embodiments, the molecular structure may be regarded as one that does not include amino acid residues that do not bear at least one bioactive agent.

The phrase "reactive group", as used herein, refers to a chemical group that is capable of undergoing a chemical reaction that typically leads to the formation a covalent bond. Chemical reactions that lead to a bond formation include, for example, cycloaddition reactions (such as the Diels-Alder's reaction, the 1,3-dipolar cycloaddition Huisgen reaction, and the similar "click reaction"), condensations, nucleophilic and electrophilic addition reactions, nucleophilic and electrophilic substitutions, addition and elimination reactions, alkylation reactions, rearrangement reactions and any other known organic reactions that involve a reactive group.

Representative examples of reactive groups include, without limitation, acyl halide, aldehyde, alkoxy, alkyne, amide, amine, aryloxy, azide, aziridine, azo, carbamate, carbonyl, carboxyl, carboxylate, cyano, diene, dienophile, epoxy, guanidine, guanyl, halide, hydrazide, hydrazine, hydroxy, hydroxylamine, imino, isocyanate, nitro, phosphate, phosphonate, sulfinyl, sulfonamide, sulfonate, thioalkoxy, thioaryloxy, thiocarbamate, thiocarbonyl, thiohydroxy, thiourea and urea, as these terms are defined hereinafter.

According some embodiments of the present invention, various elements of the molecular structure presented herein are attached to one or more linking moieties via spacer moieties. As used herein, the phrase "spacer moiety" describes a chemical moiety that typically extends between two chemical moieties and is attached to each of the chemical moieties via covalent bonds. The spacer moiety may be linear or cyclic, be branched or unbranched, rigid or flexible.

The nature of the spacer moieties can be regarded as having an effect on two aspects, the synthetic aspect, namely the influence of the spacer moieties on the process of preparing the molecular structures presented herein, and the influence of the spacer moieties on the biology activity of the molecular structures in terms of drug-release profile(s), biological activity, bioavailability and other ADME-Tox considerations.

According to some embodiments of the present invention, the spacer moieties are selected such that they allow and/or promote the conjugation reaction between various elements of the molecular structures presented herein, and reduce the probability for the formation of side-products due to undesired reactions. Such traits can be selected for in terms of spacer's length, flexibility, structure and specific chemical reactivity or lack thereof. Spacer moieties with fewer reactive groups will present a simpler synthetic challenge, requiring less protection/deprotection steps and affording higher chemical yields. For example, saturated and linear alkyls of 1-10, or 1-5 carbon atoms, having one reactive group at the end atom for conjugation with a corresponding reactive group, would afford substantially higher yield and fewer side products. Similarly, a spacer moiety based on one or two chained benzyl rings would also lead to an efficient conjugation reaction.

According to some embodiments of the present invention, the spacer moieties are selected such that they provide favorable cleavage conditions, as these are discussed hereinbelow. For example, a spacer may alter the accessibility of an enzyme to the linking moiety, thereby allowing the enzyme to cleave the linkage between the bioactive agent and the molecular structure.

According to some embodiments of the present invention, the spacer moieties include, without limitation, —CH$_2$—, —CH$_2$—O—, —(CH$_2$)$_2$—, —(CH$_2$)$_2$—O—, —(CH$_2$)$_3$—, —(CH$_2$)$_3$—O—, —(CH$_2$)$_4$—, —(CH$_2$)$_5$—, —(CH$_2$)$_6$—, —(CH(CH$_3$))—CH$_2$—, —CH═CH—CH═CH—, —C≡C—C≡C—, —CH$_2$CH(OH)CH$_2$—, —CH$_2$—O—CH$_2$—, —CH$_2$—O—CH$_2$—O—, —(CH$_2$)$_2$—O—(CH$_2$)$_2$—, —(CH$_2$)$_2$—O—(CH$_2$)$_2$—O—, —CH$_2$-mC$_6$H$_4$—CH$_2$—, —CH$_2$-mC$_6$H$_4$—CH$_2$—O—, —CH$_2$-pC$_6$H$_4$—CH$_2$—, —CH$_2$-pC$_6$H$_4$—CH$_2$—O—, —CH$_2$—NHCO—, —C$_6$H$_4$—NHCO—, —CH$_2$—O—CH$_2$— and —CH═CH—CH$_2$—NH—(CH$_2$)$_2$—.

In some embodiments, a spacer moiety can be regarded as forming a part of a linking moiety.

Examples of linking moieties, according to some embodiments of the present invention, include without limitation, amide, carbamate, carbonate, lactone, lactam, carboxylate, ester, cycloalkene, cyclohexene, heteroalicyclic, heteroaryl, triazine, triazole, disulfide, imine, imide, oxime, aldimine, ketimine, hydrazone, semicarbazone, acetal, ketal, aminal, aminoacetal, thioacetal, thioketal, phosphate ester, and the like. Other linking moieties are defined hereinbelow, and further other linking moieties are contemplated within the scope of the term as used herein.

According to some embodiments, the linking moiety is selected from the group consisting of:

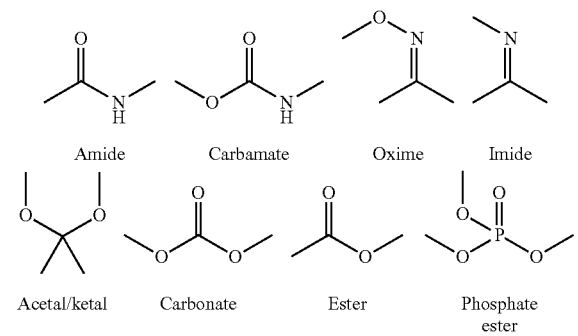

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

As used herein, the terms "amine" or "amino", describe both a —NR'R" end group and a —NR'— linking moiety, wherein R' and R" are each independently hydrogen, alkyl, cycloalkyl, aryl, as these terms are defined hereinbelow.

Herein throughout, the phrase "end group" describes a chemical group that is attached to one compound (a substituent; a reactive group; a functional group etc.), while the term "linking moiety" describes a group that is attached to two compounds and links therebetween.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydrogen, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine, as these terms are defined herein.

The term "alkyl" describes a saturated aliphatic hydrocarbon including straight chain (unbranched) and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking moiety, as this phrase is defined hereinabove, which connects two or more moieties via at least two carbons in its chain. When an alkyl is a linking moiety, it is also referred to herein as "alkylene", e.g., methylene, ethylene, propylene, etc.

The term "alkenyl" describes an unsaturated alkyl, as defined herein, having at least two carbon atoms and at least one carbon-carbon double bond. The alkenyl may be substituted or unsubstituted by one or more substituents, as described for alkyl hereinabove.

The terms "alkynyl" or "alkyne", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e., rings that share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking moiety, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking moiety, as this phrase is defined hereinabove, connecting two or more moieties at two or more positions thereof. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking moiety, as this term is defined hereinabove, connecting two or more moieties at two or more positions thereof. Preferably, the aryl is phenyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking moiety, as this phrase is defined hereinabove, connecting two or more moieties at two or more positions thereof. Representative examples are pyridine, pyrrole, oxazole, indole, purine and the like.

The term "alkaryl" describes an alkyl, as defined herein, which is substituted by one or more aryl or heteroaryl groups. An example of alkaryl is benzyl.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

As used herein, the term "acyl" refers to a group having the general formula —C(=O)R', —C(=O)OR', —C(=O)—O—C(=O)R', —C(=O)SR', —C(=O)N(R')$_2$, —C(=S)R', —C(=S)N(R')$_2$, and —C(=S)S(R'), —C(=NR')R", —C(=NR')OR", —C(=NR')SR", and —C(=NR')N(R")$_2$, wherein R' and R" are each independently hydrogen, halo, substituted or unsubstituted hydroxyl, substituted or unsubstituted thiol, substituted or unsubstituted amine, substituted or unsubstituted acyl, cyclic or acyclic, substituted or unsubstituted, branched or unbranched aliphatic, cyclic or acyclic, substituted or unsubstituted, branched or unbranched heteroaliphatic, cyclic or acyclic, substituted or unsubstituted, branched or unbranched alkyl, cyclic or acyclic, substituted or unsubstituted, branched or unbranched alkenyl, substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X_1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thioxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl) alkyl or (cycloalkyl)alkenyl.

As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur.

Suitable heteroaliphatic groups include, but are not limited to, linear or branched, heteroalkyl, heteroalkenyl, and heteroalkynyl groups.

The term "halo" describes fluorine, chlorine, bromine or iodine substituent.

The term "halide" describes an anion of a halogen atom, namely F$^-$, Cl$^-$ Br$^-$ and I$^-$.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking moiety, as these phrases are defined hereinabove, where R' is as defined hereinabove.

The term "thiosulfate" describes a —O—S(=S)(=O)—OR' end group or a —O—S(=S)(=O)—O— linking moiety, as these phrases are defined hereinabove, where R' is as defined hereinabove.

The term "sulfite" describes an —O—S(=O)—O—R' end group or a —O—S(=O)—O— group linking moiety, as these phrases are defined hereinabove, where R' is as defined hereinabove.

The term "thiosulfite" describes a —O—S(=S)—O—R' end group or an —O—S(=S)—O— group linking moiety, as these phrases are defined hereinabove, where R' is as defined hereinabove.

The term "sulfinate" or "sulfinyl" describes a —S(=O)—OR' end group or an —S(=O)—O— group linking moiety, as these phrases are defined hereinabove, where R' is as defined hereinabove.

The terms "solfoxide" or "sulfinyl" describe a —S(=O) R' end group or an —S(=O)— linking moiety, as these phrases are defined hereinabove, where R' is as defined hereinabove.

The term "sulfonate" or "sulfonyl" describes a —S(=O)$_2$—R' end group or an —S(=O)$_2$— linking moiety, as these phrases are defined hereinabove, where R' is as defined herein.

The term "S-sulfonamide" describes a —S(=O)$_2$—NR'R" end group or a —S(=O)$_2$—NR'— linking moiety, as these phrases are defined hereinabove, with R' and R" as defined herein.

The term "N-sulfonamide" describes an R'S(=O)₂—NR"— end group or a —S(=O)₂—NR'— linking moiety, as these phrases are defined hereinabove, where R' and R" are as defined herein.

The term "disulfide" refers to a —S—SR' end group or a —S—S— linking moiety, as these phrases are defined hereinabove, where R' is as defined herein.

The term "phosphate" describes an —O—P(=O)₂(OR') end or reactive group or a —O—P(=O)₂(O)— linking moiety, as these phrases are defined hereinabove, with R' as defined herein.

The term "phosphonate" describes a —P(=O)(OR')(OR") end or reactive group or a —P(=O)(OR')(O)— linking moiety, as these phrases are defined hereinabove, with R' and R" as defined herein.

The term "thiophosphonate" describes a —P(=S)(OR')(OR") end group or a —P(=S)(OR')(O)— linking moiety, as these phrases are defined hereinabove, with R' and R" as defined herein.

The term "carbonyl" or "carbonate" as used herein, describes a —C(=O)—R' end group or a —C(=O)— linking moiety, as these phrases are defined hereinabove, with R' as defined herein.

The term "thiocarbonyl" as used herein, describes a —C(=S)—R' end group or a —C(=S)— linking moiety, as these phrases are defined hereinabove, with R' as defined herein.

The term "oxo" as used herein, described a =O end group.

The term "thioxo" as used herein, described a =S end group.

The term "oxime" describes a =N—OH end group or a =N—O— linking moiety, as these phrases are defined hereinabove.

The term "hydroxyl" describes a —OH group.

As used herein, the term "aldehyde" refers to an —C(=O)—H group.

The term "acyl halide" describes a —(C=O)R"" group wherein R"" is halo, as defined hereinabove.

The term "alkoxy" as used herein describes an —O-alkyl, an —O-cycloalkyl, as defined hereinabove. The ether group —O— is also a possible linking moiety.

The term "aryloxy" describes both an —O-aryl and an —O-heteroaryl group, as defined herein.

The term "disulfide" as used herein describes an —S—S— linking moiety, which in some cases forms between two thiohydroxyl groups.

The terms "thio", "sulfhydryl" or "thiohydroxyl" as used herein describe an —SH group.

The term "thioalkoxy" or "thioether" describes both a —S-alkyl group, and a —S-cycloalkyl group, as defined herein. The thioether group —S— is also a possible linking moiety.

The term "thioaryloxy" describes both a —S-aryl and a —S-heteroaryl group, as defined herein. The thioarylether group —S-aryl- is also a possible linking moiety.

The term "cyano" or "nitrile" describes a —C≡N group.

The term "isocyanate" describes an —N=C=O group.

The term "nitro" describes an —NO₂ group.

The term "carboxylate" or "ester", as used herein encompasses C-carboxylate and O-carboxylate.

The term "C-carboxylate" describes a —C(=O)—OR' end group or a —C(=O)—O— linking moiety, as these phrases are defined hereinabove, where R' is as defined herein.

The term "O-carboxylate" describes a —OC(=O)R' end group or a —OC(=O)— linking moiety, as these phrases are defined hereinabove, where R' is as defined herein.

The term "thiocarboxylate" as used herein encompasses "C-thiocarboxylate and O-thiocarboxylate.

The term "C-thiocarboxylate" describes a —C(=S)—OR' end group or a —C(=S)—O— linking moiety, as these phrases are defined hereinabove, where R' is as defined herein.

The term "O-thiocarboxylate" describes a —OC(=S)R' end group or a —OC(=S)— linking moiety, as these phrases are defined hereinabove, where R' is as defined herein.

The term "carbamate" as used herein encompasses N-carbamate and O-carbamate.

The term "N-carbamate" describes an R"OC(=O)—NR'— end group or a —OC(=O)—NR'— linking moiety, as these phrases are defined hereinabove, with R' and R" as defined herein.

The term "O-carbamate" describes an —OC(=O)—NR'R" end group or an —OC(=O)—NR'— linking moiety, as these phrases are defined hereinabove, with R' and R" as defined herein.

The term "thiocarbamate" as used herein encompasses N-thiocarbamate and O-thiocarbamate.

The term "O-thiocarbamate" describes a —OC(=S)—NR'R" end group or a —OC(=S)—NR'— linking moiety, as these phrases are defined hereinabove, with R' and R" as defined herein.

The term "N-thiocarbamate" describes an R"OC(=S)NR'— end group or a —OC(=S)NR'— linking moiety, as these phrases are defined hereinabove, with R' and R" as defined herein.

The term "dithiocarbamate" as used herein encompasses N-dithiocarbamate and S-dithiocarbamate.

The term "S-dithiocarbamate" describes a —SC(=S)—NR'R" end group or a —SC(=S)NR'— linking moiety, as these phrases are defined hereinabove, with R' and R" as defined herein.

The term "N-dithiocarbamate" describes an R"SC(=S)NR'— end group or a —SC(=S)NR'— linking moiety, as these phrases are defined hereinabove, with R' and R" as defined herein.

The term "urea", which is also referred to herein as "ureido", describes a —NR'C(=O)—NR"R'" end group or a —NR'C(=O)—NR"— linking moiety, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking moiety, with R', R" and R'" as defined herein.

The term "amide" as used herein encompasses C-amide and N-amide.

The term "C-amide" describes a —C(=O)—NR'R" end group or a —C(=O)—NR'— linking moiety, as these phrases are defined hereinabove, where R' and R" are as defined herein.

The term "N-amide" describes a R'C(=O)—NR"— end group or a R'C(=O)—N— linking moiety, as these phrases are defined hereinabove, where R' and R" are as defined herein.

The term "imine", which is also referred to in the art interchangeably as "Schiff-base", describes a —N=CR'— linking moiety, with R' as defined herein or hydrogen. As is well known in the art, Schiff bases are typically formed by reacting an aldehyde or a ketone and an amine-containing moiety such as amine, hydrazine, hydrazide and the like, as these terms are defined herein. The term "aldimine" refers to a —CH=N— imine which is derived from an aldehyde. The term "ketimine" refers to a —CR'=N— imine which is derived from a ketone.

The term "hydrazone" refers to a —R'C=N—NR"— linking moiety, wherein R' and R" are as defined herein.

The term "semicarbazone" refers to a linking moiety which forms in a condensation reaction between an aldehyde or ketone and semicarbazide. A semicarbazone linking moiety stemming from a ketone is a —R'C=NNR"C(=O)NR'''—, and a linking moiety stemming from an aldehyde is a —CR'=NNR"C(=O)NR'''—, wherein R' and R" are as defined herein and R''' or as defined for R'.

As used herein, the term "lactone" refers to a cyclic ester, namely the intra-condensation product of an alcohol group —OH and a carboxylic acid group —COOH in the same molecule.

As used herein, the term "lactam" refers to a cyclic amide, as this term is defined herein. A lactam with two carbon atoms beside the carbonyl and four ring atoms in total is referred to as a β-lactam, a lactam with three carbon atoms beside the carbonyl and five ring atoms in total is referred to as a γ-lactam, a lactam with four carbon atoms beside the carbonyl and six ring atoms in total is referred to as a δ-lactam, and so on.

The term "guanyl" describes a R'R"NC(=N)— end group or a —R'NC(=N)— linking moiety, as these phrases are defined hereinabove, where R' and R" are as defined herein.

The term "guanidine" describes a —R'NC(=N)—NR"R''' end group or a —R'NC(=N)— NR"— linking moiety, as these phrases are defined hereinabove, where R', R" and R''' are as defined herein.

The term "hydrazine" describes a —NR'—NR"R''' end group or a —NR'—NR"— linking moiety, as these phrases are defined hereinabove, with R', R", and R''' as defined herein.

As used herein, the term "hydrazide" describes a —C(=O)—NR'—NR"R''' end group or a —C(=O)—NR'—NR"— linking moiety, as these phrases are defined hereinabove, where R', R" and R''' are as defined herein.

The term "hydroxylamine", as used herein, refers to either a —NHOH group or a —ONH₂.

As used herein, the terms "azo" or "diazo" describe a —N=N—R' end group or a —N=N— linking moiety, as these phrases are defined hereinabove, where R' is as defined herein.

As used herein, the term "azido" described a —N=N⁺=N⁻ (—N₃) end group.

The term "triazine" refers to a heterocyclic ring, analogous to the six-membered benzene ring but with three carbons replaced by nitrogen atoms. The three isomers of triazine are distinguished from each other by the positions of their nitrogen atoms, and are referred to as 1,2,3-triazine, 1,2,4-triazine, and 1,3,5-triazine. Other aromatic nitrogen heterocycles include pyridines with 1 ring nitrogen atom, diazines with 2 nitrogen atoms in the ring and tetrazines with 4 ring nitrogen atoms.

The term "triazole" refers to either one of a pair of isomeric chemical compounds with molecular formula $C_2H_3N_3$, having a five-membered ring of two carbon atoms and three nitrogen atoms, namely 1,2,3-triazoles and 1,2,4-triazoles.

The term "aziridine", as used herein, refers to a reactive group which is a three membered heterocycle with one amine group and two methylene groups, having a molecular formula of —$C_2H_3$NH.

As used herein, the term "thiohydrazide" describes a —C(=S)—NR'—NR"R''' end group or a —C(=S)—NR'—NR"— linking moiety, as these phrases are defined hereinabove, where R', R" and R''' are as defined herein.

As used herein, the term "methyleneamine" describes an —NR'—CH₂—CH=CR"R''' end group or a —NR'—CH₂—CH=CR"— linking moiety, as these phrases are defined hereinabove, where R', R" and R''' are as defined herein.

The term "diene", as used herein, refers to a —CR'=CR"—CR'''=CR''''— group, wherein R' as defined hereinabove, and R", R''' and R'''' are as defined for R'.

The term "dienophile", as used herein, refers to a reactive group that reacts with a diene, typically in a Diels-Alder reaction mechanism, hence a dienophile is typically a double bond or an alkenyl.

The term "epoxy", as used herein, refers to a reactive group which is a three membered heterocycle with one oxygen and two methylene groups, having a molecular formula of —$C_2H_3$O.

The phrase "covalent bond", as used herein, refers to one or more pairs of electrons that are shared between atoms in a form of chemical bonding.

According to some embodiments of the present invention, some linking moieties result from a reaction between two reactive groups. Alternatively, a desired linking moiety is first generated and a bioactive agent and/or a spacer moiety are attached thereto.

Linking Moiety Lability:

According to some embodiments of the present invention, the linking moiety is stable at physiological conditions, namely the linking moiety does not disintegrate for the duration of exposure to the physiological environment in the bodily site. Such linking moiety is referred to herein a "biostable". Biostable linking moieties offer the advantage of an extended period of time at which the molecular structure can exert its biological activity (releasing bioactive agents at the targeted bodily site), up to the time it is secreted or otherwise removed from the bodily site. An exemplary biostable linking moiety is a triazole-based linking moiety. It is noted that biostability is also a relative term, meaning that a biostable linking moiety takes longer to break or requires certain cleavage conditions which hare less frequently encountered by the molecular structure when present in physiological conditions.

In the context of some embodiments of the present invention, biocleavable linking moieties are selected so as to break and release the bioactive agent attached thereto at certain conditions, referred to herein as "drug-releasing conditions" or "cleavage conditions".

In some embodiments, linking moieties that link between the MAAP and the targeting moiety, and link between the amino acid residues in the MAAP, and denoted respectively $L_0$ and $L_{12}$, $L_{22}$ ... $L_{n2}$ in general Formula I, are selected to be more biostable than other lining moieties, such as those linking the bioactive agents to the MAAP. In some embodiments, $L_{12}$, $L_{22}$ ... $L_{n2}$ are amides (peptide bonds). In some embodiments, $L_0$ and $L_{12}$, $L_{22}$ ... $L_{n2}$ are amides.

According to some embodiments of the present invention, some of the linking moieties are biocleavable-linking moieties. As used herein, the terms "biocleavable" and "biodegradable" are used interchangeably to refer to moieties that degrade (i.e., break and/or lose at least some of their covalent structure) under physiological or endosomal conditions. Biodegradable moieties are not necessarily hydrolytically degradable and may require enzymatic action to degrade.

As used herein, the terms "biocleavable moiety" or "biodegradable moiety" describe a chemical moiety, which undergoes cleavage in a biological system such as, for example, the digestive system of an organism or a metabolic system in a living cell.

In some embodiments, biocleavable linking moieties are selected according to their susceptibility to certain enzymes that are likely to be present at the targeted bodily site or at any other bodily site where cleavage is intended, thereby defining the cleavage conditions.

Representative examples of biocleavable moieties include, without limitation, amides, carboxylates, carbamates, phosphates, hydrazides, thiohydrazides, disulfides, epoxides, peroxo and methyleneamines. Such moieties are typically subjected to enzymatic cleavages in a biological system, by enzymes such as, for example, hydrolases, amidases, kinases, peptidases, phospholipases, lipases, proteases, esterases, epoxide hydrolases, nitrilases, glycosidases and the like.

For example, hydrolases (EC number beginning with 3) catalyze hydrolysis of a chemical bond according to the general reaction scheme A-B+$H_2O$→A-OH+B-H. Ester bonds are cleaved by sub-group of hydrolases known as esterases (EC number beginning with 3.1), which include nucleases, phosphodiesterases, lipases and phosphatases. Hydrolases having an EC number beginning with 3.4 are peptidases, which act on peptide bonds.

Additional information pertaining to enzymes, enzymatic reactions, and enzyme-linking moiety correlations can be found in various publically accessible sources, such as Bairoch A., "*The ENZYME database in 2000*", *Nucleic Acids Res,* 2000, 28, pp. 304-305.

In some embodiments, certain linking moieties are selected to be more labile, such as the $L_{11} L_{21} \ldots L_{n1}$ linking moieties, which are defined in general Formula I as the moieties linking between the various bioactive agents and the molecular structure presented herein. By "more labile", it is meant that some of the linking moieties have a higher tendency to break at given cleavage conditions compared to other linking moieties. In some embodiments, the linking moieties are selected according to a certain lability hierarchy that allows the design of a particular drug-releasing profile, and/or a particular multi-drug-releasing profile, wherein the order and the rate of drug release is controllable according to the lability hierarchy. In the context of some embodiment of the invention, the more labile linking moieties, higher in the lability hierarchy will break first and at a higher rate than those lower in the lability hierarchy. The ability to select linking moieties according to their lability hierarchy provides molecular structures with differential multi-drug releasing profiles, according to some embodiments of the present invention.

The selection of the linking moieties according to lability hierarchy is determined according to the cleavage conditions, which the molecular structure is expected to experience once it is administered into a living cell/tissue/organ (collectively referred to herein as a "bodily site"). Cleavage conditions include the chemical and physical conditions that are present in the bodily site, such as temperature, pH, the presence of reactive species and the presence of enzymes, all of which can cause a given linking moiety to break and release the bioactive agent attached thereto.

For example, some linking moieties are more labile (susceptible to) in higher temperatures, while others are susceptible to higher or lower pH values compared to other linking moieties. In such cases, a molecular structure which is design to target a bodily site that is characterized by a localized pH value compared to its surroundings, an acid-labile or an $H^+$-labile linking moiety is advantageously selected to release the bioactive agent it bears.

In some embodiments, each of $L_{11}, L_{21} \ldots L_{n1}$ is characterized by a given cleavage condition, and any one of $L_{11}, L_{21} \ldots L_{n1}$ is selected such that at least one of $L_{11}, L_{21} \ldots L_{n1}$ is different than the other $L_{11}, L_{21} \ldots L_{n1}$ linking moieties, based on the cleavage condition thereof. In some embodiments, each of $L_{11}, L_{21} \ldots L_{n1}$ is selected such that it is characterized by having a different cleavage condition.

Bioactive Agent:

As discussed hereinabove, the molecular structures is designed to carry a multiple-drug payload, which can comprise several copies of the same drug, linked by similar or different linking moieties, to control the release profile of the payload, or comprise of a series of different drugs linked by similar or different linking moieties. In cases where the drugs are the same, the molecular structures of the present invention provide for substantial enhancement of the functionality of the drugs, both in terms of localized release, concerted release or prolonged sequential release thereof. In cases where the drugs are different one from one-another, the molecular structures of the present invention provides for simultaneous, concerted or sequential release of the drugs and can therefore be specifically advantageous in cases where the different drugs confer a cumulative and/or a synergistic effect.

In the context of the present embodiments, the terms "bioactive agent", "pharmaceutically active agent" and "drug" are used interchangeably.

As used herein, the terms "bioactive agent" and "drug" refer to small molecules or biomolecules that alter, inhibit, activate, or otherwise affect a biological mechanism or event. Bioactive agent that can be tethered to the MAAP, according to embodiments of the present invention include, but are not limited to, anti-cancer substances for all types and stages of cancer and cancer treatments (chemotherapeutic, proliferative, acute, genetic, spontaneous etc.), anti-proliferative agents, chemo sensitizing agents, anti-inflammatory agents (including steroidal and non-steroidal anti-inflammatory agents and anti-pyretic agents), antimicrobial agents (including antibiotics, antiviral, antifungal, anti-parasite, anti-protozoan etc.), anti-oxidants, hormones, anti-hypertensive agents, anti-AIDS substances, anti-diabetic substances, immunosuppressants, enzyme inhibitors, neurotoxins, opioids, hypnotics, anti-histamines, lubricants, tranquilizers, anti-convulsants, muscle relaxants and anti-Parkinson substances, antipruritic agents, anti-spasmodics and muscle contractants including channel blockers, miotics and anti-cholinergics, anti-glaucoma compounds, modulators of cell-extracellular matrix interactions including cell growth inhibitors and anti-adhesion molecules, vitamins, vasodilating agents, inhibitors of DNA, RNA or protein synthesis, analgesics, anti-angiogenic factors, anti-secretory factors, anticoagulants and/or anti-thrombotic agents, anesthetics, ophthalmics, prostaglandins, anti-depressants, antipsychotic substances, anti-emetics, radioactive agents and imaging agents. A more comprehensive listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 Da. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, are all considered acceptable for use in accordance with the present invention.

Anti-cancer drugs that can be linked and controllably released from the molecular structure according to some embodiments of the invention include, but are not limited to Chlorambucil; 3-(9-Acridinylamino)-5-(hydroxymethyl) aniline; Azatoxin; Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Non-limiting examples of chemotherapeutic agents that can be efficiently delivered by the molecular structures of the present invention, include amino containing chemotherapeutic agents such as camptothecin, daunorubicin, doxorubicin, N-(5,5-diacetoxypentyl)doxorubicin, anthracycline, mitomycin C, mitomycin A, 9-amino aminopertin, antinomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, irinotecan, topotecan, 9-amino camptothecin, paclitaxel, docetaxel, esperamycin, 1,8-dihydroxy-bicyclo [7.3.1]trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents. Additional chemotherapeutic agents include, without limitation, an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, a gonadotropin-releasing hormone analog, bleomycin, doxorubicin, paclitaxel, 4-OH cyclophosphamide and cisplatinum.

Anti-inflammatory drugs that can be linked and controllably released from the molecular structure according to some embodiments of the invention include, but are not limited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate;

Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

Suitable antimicrobial agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

Representative examples of hormones include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Non-limiting examples of analgesic agents that can be efficiently delivered by the molecular structures of the present invention, include acetaminophen, alfentanil hydrochloride, aminobenzoate potassium, aminobenzoate sodium, anidoxime, anileridine, anileridine hydrochloride, anilopam hydrochloride, anirolac, antipyrine, aspirin, benoxaprofen, benzydamine hydrochloride, bicifadine hydrochloride, brifentanil hydrochloride, bromadoline maleate, bromfenac sodium, buprenorphine hydrochloride, butacetin, butixirate, butorphanol, butorphanol tartrate, carbamazepine, carbaspirin calcium, carbiphene hydrochloride, carfentanil citrate, ciprefadol succinate, ciramadol, ciramadol hydrochloride, clonixeril, clonixin, codeine, codeine phosphate, codeine sulfate, conorphone hydrochloride, cyclazocine, dexoxadrol hydrochloride, dexpemedolac, dezocine, diflunisal, dihydrocodeine bitartrate, dimefadane, dipyrone, doxpicomine hydrochloride, drinidene, enadoline hydrochloride, epirizole, ergotamine tartrate, ethoxazene hydrochloride, etofenamate, eugenol, fenoprofen, fenoprofen calcium, fentanyl citrate, floctafenine, flufenisal, flunixin, flunixin meglumine, flupirtine maleate, fluproquazone, fluradoline hydrochloride, flurbiprofen, hydromorphone hydrochloride, ibufenac, indoprofen, ketazocine, ketorfanol, ketorolac tromethamine, letimide hydrochloride, levomethadyl acetate, levomethadyl acetate hydrochloride, levonantradol hydrochloride, levorphanol tartrate, lofemizole hydrochloride, lofentanil oxalate, lorcinadol, lornoxicam, magnesium salicylate, mefenamic acid, menabitan hydrochloride, meperidine hydrochloride, meptazinol hydrochloride, methadone hydrochloride, methadyl acetate, methopholine, methotrimeprazine, metkephamid acetate, mimbane hydrochloride, mirfentanil hydrochloride, molinazone, morphine sulfate, moxazocine, nabitan hydrochloride, nalbuphine hydrochloride, nalmexone hydrochloride, namoxyrate, nantradol hydrochloride, naproxen, naproxen sodium, naproxol, nefopam hydrochloride, nexeridine hydrochloride, noracymethadol hydrochloride, ocfentanil hydrochloride, octazamide, olvanil, oxetorone fumarate, oxycodone, oxycodone hydrochloride, oxycodone terephthalate, oxymorphone hydrochloride, pemedolac, pentamorphone, pentazocine, pentazocine hydrochloride, pentazocine lactate, phenazopyridine hydrochloride, phenyramidol hydrochloride, picenadol hydrochloride, pinadoline, pirfenidone, piroxicam olamine, pravadoline maleate, prodilidine hydrochloride, profadol hydrochloride, propiram fumarate, propoxyphene hydrochloride, propoxyphene nap sylate, proxazole, proxazole citrate, proxorphan tartrate, pyrroliphene hydrochloride, remifentanil hydrochloride, salcolex, salethamide maleate, salicylamide, salicylate meglumine, salsalate, sodium salicylate, spiradoline mesylate, sufentanil, sufentanil citrate, talmetacin, talniflumate, talosalate, tazadolene succinate, tebufelone, tetrydamine, tifurac sodium, tilidine hydrochloride, tiopinac, tonazocine mesylate, tramadol hydrochloride, trefentanil hydrochloride, trolamine, veradoline hydrochloride, verilopam hydrochloride, volazocine, xorphanol mesylate, xylazine hydrochloride, zenazocine mesylate, zomepirac sodium and zucapsaicin.

Mechanism of Therapeutic Biological Activity:

According to some embodiments, the molecular structure carries at least two types of drugs which differ than one another by their mechanism of biological activity. Without being bound by any particular theory, it is assumed that a molecular structure that can deliver at least two bioactive agents that act by two different mechanism of biological activity, would provide superior therapeutic effects, particularly when attempting to affect a resistant cellular system, such as resistant strains of pathogenic microorganisms or multi-drug resistant cancerous cells.

In the context of embodiments of the present invention, the phrase "mechanism of biological activity" refers to the biochemical mechanism by which a drug exerts its beneficial therapeutic effect. Example of mechanisms of biological activity include cell membrane disruption, destabilization and permeabilization, disruption of cell metabolism, protein synthesis disruption, disruption of DNA/RNA transcription, translation and replication, disruption of cell division, and the like.

A representative example of a treatment of a medical condition that can benefit from using a combination of drugs having a different mechanism of biological activity is cancer. In the broad sense, most anti-cancer drugs work by impairing mitosis (cell division), effectively targeting fast-dividing cells. As these drugs cause damage to cells, they are termed cytotoxic. They prevent mitosis by various mechanisms including damaging DNA and inhibition of the cellular machinery involved in cell division. Without being bound by any particular theory, it is assumed that these drugs kill cancer cells by inducing a programmed form of cell death known as apoptosis. As anti-cancer chemotherapy affects cell division, tumors with high growth rates (such as acute myelogenous leukemia and the aggressive lymphomas, including Hodgkin's disease) are more sensitive to chemotherapy, as a larger proportion of the targeted cells are undergoing cell division at any time. Since malignancies with slower growth rates, such as indolent lymphomas, and heterogeneic tumors, tend to respond to chemotherapy more modestly, a combination of drugs that exert cell division inhibition with drugs that exert other mechanism of biological activity, such as anti-protein-biosynthesis activity, metabolism and cell membrane disruption is advantageous.

In some embodiments, the anti-cancer drug is an alkylating agent, or alkylating antineoplastic agent. Alkylating agents constitute a class of chemotherapeutics that exhibit the capacity to alkylate a wide range of molecules, including proteins, RNA and DNA, and this capacity to bind covalently to DNA via their alkyl group is the primary cause for their anti-cancer effects. DNA is made of two strands and the molecules may either bind twice to one strand of DNA (intrastrand crosslink) or may bind once to both strands (interstrand crosslink). If the cell tries to replicate crosslinked DNA during cell division, or tries to repair it, the DNA strands can break, and this leads to a form of programmed cell death called apoptosis. Alkylating agents will work at any point in the cell cycle and thus are known as cell cycle-independent drugs. For this reason the effect on the cell is dose dependent; the fraction of cells that die is directly proportional to the dose of drug. Subtypes of alkylating agents include nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin, which impair cell function by forming covalent bonds with the amino, carboxyl, sulfhydryl, and phosphate groups in biologically important molecules. Non-classical alkylating agents include procarbazine and hexamethylmelamine.

In some embodiments, the anti-cancer drug is an anti-metabolism agent, or an anti-metabolite. Anti-metabolites are a group of molecules that impede DNA and RNA synthesis; many of which have a similar structure to the building blocks of DNA and RNA. The building blocks are nucleotides; a molecule comprising a nucleobase, a sugar and a phosphate group. The nucleobases are divided into purines (guanine and adenine) and pyrimidines (cytosine, thymine and uracil). Anti-metabolites resemble either nucleobases or nucleosides (a nucleotide without the phosphate group), but have altered chemical groups. These drugs exert their effect by either blocking the enzymes required for DNA synthesis or becoming incorporated into DNA or RNA. By inhibiting the enzymes involved in DNA synthesis, anti-metabolites prevent mitosis because the DNA cannot duplicate itself. Also, after misincorporation of the molecules into DNA, DNA damage can occur and programmed cell death (apoptosis) is induced. Unlike alkylating agents, anti-metabolites are cell cycle dependent, which means that they exert therapeutic biological activity only during a specific part of the cell cycle, in this case 5-phase (the DNA synthesis phase). For this reason, at a certain dose, the effect plateaus and proportionally no more cell death occurs with increased doses. Subtypes of the anti-metabolites are the anti-folates, fluoropyrimidines, deoxynucleoside analogues and thiopurines. Examples of anti-folates include methotrexate and pemetrexed. Methotrexate inhibits dihydrofolate reductase (DHFR), an enzyme that regenerates tetrahydrofolate from dihydrofolate. When the enzyme is inhibited by methotrexate, the cellular levels of folate coenzymes diminish. These are required for thymidylate and purine production, which are both essential for DNA synthesis and cell division. Pemetrexed is another anti-metabolite that affects purine and pyrimidine production, and therefore also inhibits DNA synthesis. It primarily inhibits the enzyme thymidylate synthase, but also has effects on DHFR, aminoimidazole carboxamide ribonucleotide formyltransferase and glycinamide ribonucleotide formyltransferase. The fluoropyrimidine family of anti-metabolites includes fluorouracil and capecitabine, whereas fluorouracil is a nucleobase analogue that is metabolised in cells to form at least two active products; 5-fluourouridine monophosphate (FUMP) and 5-fluoro-2'-deoxyuridine 5'-phosphate (fdUMP). FUMP becomes incorporated into RNA and fdUMP inhibits the enzyme thymidylate synthase; both of which lead to cell death. Capecitabine can be used in the context of some embodiments of the present invention as a prodrug of 5-fluorouracil, whereas once released off the molecular structure, capecitabine is broken down in cells to produce the active drug 5-fluorouracil. Deoxynucleoside analogues include cytarabine, gemcitabine, decitabine, vidaza (5-azacytidine), fludarabine, nelarabine, cladribine, clofarabine and pentostatin. Thiopurines include thioguanine and mercaptopurine.

In some embodiments, the anti-cancer drug is an anti-microtubular agent, or an anti-microtubule. Anti-microtubule agents are plant-derived chemicals that block cell division by preventing microtubule function. Microtubules are an important cellular structure composed of two proteins; α-tubulin and β-tubulin, which are hollow rod shaped structures that are required for cell division, among other cellular functions. Microtubules are dynamic structures, which means that they are permanently in a state of assembly and disassembly. Vinca alkaloids and taxanes are the two main groups of anti-microtubule agents, and although both of these groups of drugs cause microtubule dysfunction, their mechanisms of action are completely opposite. The vinca alkaloids prevent the formation of the microtubules, whereas the taxanes prevent the microtubule disassembly; by doing so, they prevent the cancer cells from completing mitosis. Following this, cell cycle arrest occurs, which induces programmed cell death (apoptosis). In addition, these drugs can affect blood vessel growth; an essential process that tumors utilize in order to grow and metastasize. *Vinca* alkaloids are derived from the Madagascar periwinkle, *Catharanthus roseus* (formerly known as *Vinca rosea*). They bind to specific sites on tubulin, inhibiting the assembly of tubulin into microtubules. The original *vinca* alkaloids are completely natural chemicals that include vincristine and vinblastine. Following the success of these drugs, semi-synthetic *vinca* alkaloids were produced: vinorelbine, vindesine, and vinflunine. These drugs are cell cycle-specific. They bind to the tubulin molecules in S-phase and prevent proper microtubule formation required for M-phase.

Taxanes are natural and semi-synthetic drugs. The first drug of their class, paclitaxel, was originally extracted from the Pacific Yew tree, *Taxus brevifolia*. Some of these drugs, such as docetaxel, are produced semi-synthetically from a chemical found in the bark of another Yew tree; *Taxus baccata*. These drugs promote microtubule stability, preventing their disassembly. Paclitaxel prevents the cell cycle at the boundary of G2-M, whereas docetaxel exerts its effect during S-phase. Taxanes present difficulties in formulation as medicines because they are poorly soluble in water, and the tethering thereof to a molecular structure, according to some embodiments of the present invention, may improve the usefulness of this drug.

The anti-microtubule podophyllotoxin is an antineoplastic lignan obtained primarily from the American Mayapple (*Podophyllum peltatum*) and Himalayan Mayapple (*Podophyllum hexandrum* or *Podophyllum emodi*). It has anti-microtubule activity, and its mechanism is similar to that of *vinca* alkaloids in that they bind to tubulin, inhibiting microtubule formation. Podophyllotoxin is used to produce two other drugs with different mechanisms of action: etoposide and teniposide.

In some embodiments, the anti-cancer drug is a topoisomerase inhibitor. Topoisomerase inhibitors are drugs that affect the activity of two enzymes: topoisomerase I and topoisomerase II. When the DNA double-strand helix is unwound, during DNA replication or transcription, for example, the adjacent unopened DNA winds tighter (supercoils), like opening the middle of a twisted rope. The stress caused by this effect is in part aided by the topoisomerase enzymes. They produce single- or double-strand breaks into DNA, reducing the tension in the DNA strand. This allows the normal unwinding of DNA to occur during replication or transcription, and inhibition of topoisomerase I or II interferes with both of these processes.

Two topoisomerase I inhibitors, irinotecan and topotecan, are semi-synthetically derived from camptothecin, which is obtained from the Chinese ornamental tree *Camptotheca acuminata*. Drugs that target topoisomerase II can be divided into two groups. The topoisomerase II poisons cause increased levels enzymes bound to DNA. This prevents DNA replication and transcription, causes DNA strand breaks, and leads to programmed cell death (apoptosis). These agents include etoposide, doxorubicin, mitoxantrone and teniposide. The second group, catalytic inhibitors, are drugs that block the activity of topoisomerase II, and therefore prevent DNA synthesis and translation because the DNA cannot unwind properly. This group includes novobiocin, merbarone, and aclarubicin, which also have other significant mechanisms of biological activity.

In some embodiments, the anti-cancer drug is a cytotoxic antibiotic agent or cytotoxic antibiotics. Cytotoxic antibiotics are a varied group of drugs that have various mechanisms of biological activity (therapeutic action). The group includes anthracyclines and other drugs such as actinomycin, bleomycin, plicamycin and mitomycin. Doxorubicin and daunorubicin were the first two anthracyclines, and were obtained from the bacterium *Streptomyces peucetius*. Derivatives of these compounds include epirubicin and idarubicin. Other clinically used drugs in the anthracyline group are pirarubicin, aclarubicin, and mitoxantrone. The mechanisms of biological activity of anthracyclines include DNA intercalation (molecules insert between the two strands of DNA), generation of highly reactive free radicals that damage intercellular molecules and topoisomerase inhibition. Actinomycin is a complex molecule that intercalates DNA and prevents RNA synthesis. Bleomycin, a glycopeptide isolated from *Streptomyces verticillus*, also intercalates DNA, but produces free radicals that damage DNA. This occurs when bleomycin binds to a metal ion, becomes chemically reduced and reacts with oxygen. Mitomycin is a cytotoxic antibiotic with the ability to alkylate DNA.

According to some embodiments of the present invention, the drugs that are delivered by the molecular structure presented herein are selected according to their individual pharmacokinetics and pharmacology parameters for absorption, distribution, metabolism, excretion and toxicity (ADME-Tox), collectively referred to herein as ADME-Tox parameters. These ADME-Tox parameters govern some of the therapeutic efficacy of the drugs, hence while some drugs may be highly potent in vitro, their ADME-Tox parameters may render them less effective due to slow absorption and/or distribution, and/or rapid metabolism and/or excretion.

According to some embodiments of the present invention, at least one of the drugs that are delivered by the molecular structure presented herein, is selected to exhibit at least one ADME-Tox parameter that is different than the ADME-Tox parameter of the others drugs on the same molecular structure.

Targeting Moiety:

As used herein, the term "targeting moiety" describes a molecular entity that exhibits an affinity to a desired bodily site (e.g., particular organ, cells and/or tissues). In some embodiments, a targeting moiety is specific to certain targets. The target is typically a biomolecule that occurs at a higher concentration or exclusively at the targeted bodily site. In some embodiments, the targeting moiety is a biomolecule or a derivative thereof that has a specific and relatively high affinity to the target.

Targeting moieties are often employed as the bimolecular carrier in order to direct a drug to specific structures in the body or sites of physiological functions. According to some embodiments, a targeting moiety is a compound with structure or site specific reactivity.

Exemplary targeting agents include, without limitation, peptides, proteins, porphyrins, hormones, antigens, haptens, antibodies and fragments thereof, DNA fragments, RNA fragments and analogs and derivatives thereof, and any receptor ligands that bind to receptors that are expressed specifically or more abundantly at the targeted bodily sites.

As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

In some embodiments, a targeting moiety comprises a cell-internalizing moiety, such that the molecular structure can more readily penetrate a targeted cell. Exemplary cell-internalizing moieties include, without limitation, positively charges (at physiological environment) moieties such as guanidines and amines, and moieties containing same (e.g., arginine and lysine).

In some embodiments, the targeting moiety exhibits a specific affinity to cancerous cells and neoplastic tissues. Such targeting moieties may be used to target the molecular structure presented herein, thereby delivering anticancerous bioactive agents, according to some embodiments of the present invention, to cancerous cells and tissues. The result is an enhanced effect and an improved exposure of the cancerous cells and neoplastic tissues to the anticancerous bioactive agent, preferably accompanied by reduced exposure of non-cancerous cells to the anticancerous bioactive agents.

A class of compounds that is suitable as targeting moieties, according to some embodiments of the present invention, are short peptides and peptide analogs, generally referred to herein as peptidomimetic compounds, that display more favorable pharmacological properties than their prototype native peptides. The native peptide itself, the pharmacological properties of which have been optimized, generally serves as a lead for the development of these peptidomimetics. In general, a small number of amino acids (usually four to eight) are responsible for the biological activity (recognition and binding; targeting) of a peptide ligand (targeting moiety) by a receptor (target). Once this biologically active site is determined, a lead structure for development of peptidomimetic can be optimized, for example by molecular modeling programs. U.S. Pat. Nos. 5,811,392, 6,407,059 and 7,084,244, which are incorporated herein by reference in their entirety, describe the preparation and use of a class of cyclic peptidomimetic targeting moieties, which can be used in the context of some embodiments of the present invention.

Peptide nucleic acid (PNA) constitute an exemplary class of targeting moiety that may be used in the context of some embodiments of the present invention. U.S. Pat. No. 6,395,474, which is incorporated herein by reference in its entirety, describes PNA as an analogue of DNA in which the phosphodiester backbone of DNA is replaced with a pseudopeptide such as N-(2-amino-ethyl)-glycine. Methylenecarbonyl linkers attach DNA, RNA, or synthetic nucleobases to the polyamide backbone. PNA, obeying Watson-Crick hydrogen bonding rules, mimics the behavior of DNA and RNA by binding to complementary nucleic acid sequences such as those found in DNA, RNA, and other PNAs. An exemplary molecular structure utilizing PNA, according to some embodiments of the present invention, may bind, for example, to a specific mutated nucleic acid sequence found in the DNA of a cancerous tumor.

One example of a class of targeting moieties, which can be used advantageously in the context of embodiments of the present invention, is the family of tumor-targeting moieties that bind selectively to $\alpha_v\beta_3$ and $\alpha_v\beta_5$ integrins, referred to herein as the RGD (Arg-Gly-Asp) family [Arap, W. et al., *Science*, 1998, 279(5349):377-80]. Short peptides and peptidomimetic analogs, which are based on the RGD motif and exhibit is biological binding activity, can be used as targeting moieties in a molecular structure, according to some embodiments of the present invention, to inhibit the growth and possibly eradicate tumors in the treatment of cancer.

Additional targeting moieties, which can be used effectively in the context of the molecular structures presented herein for treating cancer, are described in the literature [e.g., "Novel Oncology Therapeutics: Targeted Drug Delivery for Cancer", *Journal of Drug Delivery*, Vol. 2013, 2013].

Applications:

Since the molecular structures presented herein carry, deliver and controllably release a wide variety of drugs, the molecular structures can be used to treat various medical conditions. The molecular structures presented herein can therefore be used as an active ingredient in a variety of pharmaceutical compositions, and in the preparation of a variety of medicaments.

Accordingly there is provided a pharmaceutical composition that includes, as an active ingredient, the molecular structure, according to embodiments of the present invention, and a pharmaceutically acceptable carrier.

Similarly, there is provided a use of the molecular structure, according to embodiments of the present invention, in the preparation of a medicament.

According to some embodiments of the present invention, the pharmaceutical composition or medicament, are used to treat a medical condition.

Also provided herein is a method of treating a medical condition in a subject in need thereof, which includes administering to the subject a therapeutically effective amount of the molecular structure, according to embodiments of the present invention.

As used herein, the phrase "therapeutically effective amount" describes an amount of an active agent or a molecular structure being administered, which will relieve to some extent one or more of the symptoms of the medical condition being treated. In the context of the present embodiments, the phrase "therapeutically effective amount" describes an amount of a molecular structure being administered and/or re-administered, which will relieve to some extent one or more of the symptoms of the condition being treated by being at a level that is harmful to the target cell(s) or microorganism(s), and cause a disruption to the life-cycle of the target cell(s) or microorganism(s).

In the context of embodiments of the present invention, the therapeutically effective amount may refer to the molecular structure as a whole or to the amount of one or more bioactive agent releasably attached thereto. The efficacy of any bioactive agent, including the molecular structures presented herein, can be determined by several methodologies known in the art.

According to another aspect of embodiments of the present invention, any one of the molecular structures described herein is identified for use in treating a subject diagnosed with a medical condition treatable by at least one of the drugs linked and controllably releasable from the molecular structure.

According to another aspect of embodiments of the present invention, there is provided a use of any of the molecular structures described herein as a medicament. In some embodiments, the medicament is for treating a subject diagnosed with a medical condition treatable by at least one of the drugs linked and controllably releasable from the molecular structure.

In any of the methods and uses described herein, the molecular structure can be administered as a part of a pharmaceutical composition, which further comprises a pharmaceutical acceptable carrier, as detailed hereinbelow. The carrier is selected suitable to the selected route of administration.

The molecular structures presented herein can be administered via any administration route, including, but not limited to, orally, by inhalation, or parenterally, for example, by intravenous drip or intraperitoneal, subcutaneous, intramuscular or intravenous injection, or topically (including ophtalmically, vaginally, rectally, intranasally).

According to some embodiments, the composition is packaged in a packaging material and identified in print, in or on the packaging material, for use in the treatment of a medical condition treatable by at least one of the drugs linked and controllably releasable from the molecular structure.

As used herein the phrase "pharmaceutical composition" or the term "medicament" refer to a preparation of the molecular structures presented herein, with other chemical components such as pharmaceutically acceptable and suitable carriers and excipients, and optionally with additional active agents. The purpose of a pharmaceutical composition is to facilitate administration of the molecular structure to a subject.

Hereinafter, the term "pharmaceutically acceptable carrier" refers to a carrier or a diluent that does not cause significant irritation to an organism and does not abrogate the biological activity and properties of the administered molecular structure. Examples, without limitations, of pharmaceutically acceptable carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a molecular structure. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Pharmaceutical compositions for use in accordance with embodiments of the invention thus may be formulated in conventional manner using one or more pharmaceutically acceptable carriers comprising excipients and auxiliaries, which facilitate processing of the molecular structures presented herein into preparations which can be used pharmaceutically. Proper formulation is dependent upon the route of administration chosen. Toxicity and therapeutic efficacy of the molecular structure presented herein can be determined by standard pharmaceutical procedures in experimental animals, e.g., by determining the $EC_{50}$, the $IC_{50}$ and the LD50 (lethal dose causing death in 50% of the tested animals) for a subject combination of antimicrobial agent(s) and polymer(s). The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "*The Pharmacological Basis of Therapeutics*", Ch. 1 p. 1). In general, the dosage is related to the efficacy of the active ingredient which, in the context of embodiments of the invention, is related to its minimal inhibitory concentration (MIC) and the particular pharmacokinetics and pharmacology thereof for absorption, distribution, metabolism, excretion and toxicity (ADME-Tox) parameters. The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising the molecular structures presented herein formulated in a compatible pharmaceutical carrier may also be prepared, placed in an appropriate container, and labeled for treatment of an indicated condition, as is detailed herein.

The present embodiments further encompass any enantiomers, prodrugs, solvates, hydrates and/or pharmaceutically acceptable salts of the molecular structures described herein and methods, compositions and uses utilizing enantiomers, prodrugs, solvates, hydrates and/or pharmaceutically acceptable salts of the molecular structures described herein.

The term "prodrug" refers to an agent, which is converted into a bioactive agent (the active parent drug) in vivo. In essence, the molecular structures presented herein constitute a form of a prodrug, as drug moieties, which are designed for release as bioactive agents in a controllable manner, are linked thereto. Prodrugs are typically useful for facilitating and/or targeting the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of a bioactive agent in vivo. An example, without limitation, of a prodrug would be a bioactive agent, according to some embodiments of the present invention, having one or more carboxylic acid moieties, which is administered as an ester (the "prodrug"). Such a prodrug is hydrolyzed in vivo, to thereby provide the free bioactive agent (the parent drug). The selected ester may affect both the solubility characteristics and the hydrolysis rate of the prodrug. A prodrug is typically designed to facilitate administration, e.g., by enhancing absorption. A prodrug may comprise, for example, the active compound modified with ester groups, for example, wherein any one or more of the hydroxyl groups of a compound is modified by an acyl group, optionally ($C_{1-4}$)acyl (e.g., acetyl) group to form an ester group, and/or any one or more of the carboxylic acid groups of the compound is modified by an alkoxy or aryloxy group, optionally ($C_{1-4}$)alkoxy (e.g., methyl, ethyl) group to form an ester group.

The term "solvate" refers to a complex of variable stoichiometric (e.g., di-, tri-, tetra-, penta-, hexa-, and so on), which is formed by a solute (the molecular structures described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent molecular structure and its counter ion(s), which is typically used to modify the solubility characteristics of the parent molecular structure and/or to reduce any significant irritation to an organism by the parent molecular structure, while not abrogating the biological activity and properties of the administered molecular structure.

Examples of pharmaceutically acceptable salts include, but are not limited to, mineral or organic acid salts of basic residues such as amines, and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Conventional nontoxic salts include those derived from inorganic acids such as hydrochloric, hydrobromic, sulfuric, sulfamic, phosphoric and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic acids. The pharmaceutically acceptable salts can be synthesized from the parent compound, which contains a basic or acidic moiety, by conventional chemical methods. Generally, such salts can be prepared by reacting the free acid or base forms of these compounds with a stochiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed. (Mack Publishing Company, Easton, Pa., 19143, p. 1418).

Representative examples of pharmaceutically acceptable salts that can be efficiently used in the context of the present invention include, without limitation, conjugate hydrochloride and conjugate mesylate.

According to some embodiments of the present invention, the compositions, uses and method of treatment, according to some embodiment of the present invention, may include the co-administration of at least one additional therapeutically active agent, as this is defined and discussed herein.

Medical Conditions:

The molecular structure presented herein can be used to treat any medical condition that is treatable by administration of a bioactive agent (drug). According to some embodiments of the present invention, it is advantageous to use the molecular structure to treat medical conditions, which are treatable by administration of a combination of drugs. In some embodiments, the medical condition includes an autoimmune disease, a genetic disease, a degenerative disease, a psychiatric or mental disease or condition. In some embodiments, the medical condition includes a peptic ulcer disease, Alzheimer's disease, rheumatoid arthritis, post-traumatic stress disorder, Crohn's disease, tuberculosis, leprosy, malaria and HIV/AIDS.

According to some embodiments, the degenerative disease includes Alzheimer's disease, Amyotrophic Lateral Sclerosis (ALS), a.k.a., Lou Gehrig's Disease, Osteoarthritis, Atherosclerosis, Cancer, Charcot Marie Tooth Disease (CMT), Chronic Obstructive Pulmonary Disease (COPD), Chronic traumatic encephalopathy, Diabetes, Ehlers-Danlos Syndrome, Essential tremor, Friedreich's ataxia, Leg Disease, Huntington's Disease, Inflammatory Bowel Disease (IBD), Keratoconus, Keratoglobus, Macular degeneration, Marfan's Syndrome, Multiple sclerosis, Multiple system atrophy, Muscular dystrophy, Niemann Pick disease, Osteoporosis, Parkinson's Disease, Progressive supranuclear palsy, Prostatitis, Retinitis Pigmentosa, Rheumatoid Arthritis, and Tay-Sachs Disease.

According to some embodiments, the autoimmune disease includes Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis *nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo and Wegener's granulomatosis (now termed Granulomatosis with Polyangiitis (GPA).

In some embodiments of the present invention, the medical condition is associated with an infection caused by a pathogenic microorganism, including a viral infection, a bacterial infection, a yeast infection, a fungal infection, a protozoan infection, a parasite-related infection and the like.

Medical conditions associated with a pathogenic microorganism include, without limitation, actinomycosis, anthrax, aspergillosis, bacteremia, bacterial, bacterial skin diseases, *bartonella* infections, botulism, brucellosis, *burkholderia* infections, *campylobacter* infections, candidiasis, cat-scratch disease, *chlamydia* infections, cholera, *clostridium* infections, coccidioidomycosis, cryptococcosis, dermatomycoses, dermatomycoses, diphtheria, ehrlichiosis, epidemic louse borne typhus, *Escherichia coli* infections, *fusobacterium* infections, gangrene, general infections, general mycoses, gram-negative bacterial infections, Gram-positive bacterial infections, histoplasmosis, impetigo, *klebsiella* infections, legionellosis, leprosy, leptospirosis, *listeria* infections, lyme disease, maduromycosis, melioidosis, *mycobacterium* infections, *mycoplasma* infections, necrotizing fasciitis, *nocardia* infections, onychomycosis, ornithosis, pneumococcal infections, pneumonia, *pseudomonas* infections, Q fever, rat-bite fever, relapsing fever, rheumatic fever, *rickettsia* infections, Rocky-mountain spotted fever, *salmonella* infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, *vibrio* infections, yaws, *yersinia* infections, *Yersinia pestis* plague, zoonoses and zygomycosis.

Non-limiting examples of pathogenic fungi include genus *Absidia*: *Absidia corymbifera*; genus *Ajellomyces*: *Ajellomyces capsulatus, Ajellomyces dermatitidis*; genus *Arthroderma*: *Arthroderma benhamiae, Arthroderma flavum, Arthroderma gypseum, Arthroderma incurvatum, Arthroderma otae, Arthroderma vanbreuseghemii*; genus *Aspergillus*: *Aspergillus flavus, Aspergillus fumigatus, Aspergillus niger*; genus *Blastomyces*: *Blastomyces dermatitidis*; genus *Candida*: *Candida albicans, Candida glabrata, Candida guilliermondii, Candida krusei, Candida parapsilosis, Candida tropicalis, Candida pelliculosa*; genus *Cladophialophora*: *Cladophialophora carrionii*; genus *Coccidioides*: *Coccidioides immitis*; genus *Cryptococcus*: *Cryptococcus neoformans*; genus *Cunninghamella*: *Cunninghamella* sp.;

genus *Epidermophyton*: *Epidermophyton floccosum*; genus *Exophiala*: *Exophiala dermatitidis*; genus *Filobasidiella*: *Filobasidiella neoformans*; genus *Fonsecaea*: *Fonsecaea pedrosoi*; genus *Fusarium*: *Fusarium solani*; genus *Geotrichum*: *Geotrichum candidum*; genus *Histoplasma*: *Histoplasma capsulatum*; genus *Hortaea*: *Hortaea werneckii*; genus *Issatschenkia*: *Issatschenkia orientalis*; genus *Madurella*: *Madurella grisae*; genus *Malassezia*: *Malassezia furfur, Malassezia globosa, Malassezia obtusa, Malassezia pachydermatis, Malassezia restricta, Malassezia slooffiae, Malassezia sympodialis*; genus *Microsporum*: *Microsporum canis, Microsporum flavum, Microsporum gypseum*; genus *Mucor*: *Mucor circinelloides*; genus *Nectria*: *Nectria haematococca*; genus *Paecilomyces*: *Paecilomyces variotii*; genus *Paracoccidioides*: *Paracoccidioides brasiliensis*; genus *Penicillium*: *Penicillium marneffei*; genus *Pichia, Pichia anomala, Pichia guilliermondii*; genus *Pneumocystis*: *Pneumocystis carinii*; genus *Pseudallescheria*: *Pseudallescheria boydii*; genus *Rhizopus*: *Rhizopus oryzae*; genus *Rhodotorula*: *Rhodotorula rubra*; genus *Scedosporium*: *Scedosporium apiospermum*; genus *Schizophyllum*: *Schizophyllum commune*; genus *Sporothrix*: *Sporothrix schenckii*; genus *Trichophyton*: *Trichophyton mentagrophytes, Trichophyton rubrum, Trichophyton verrucosum, Trichophyton violaceum*; and genus *Trichosporon*: *Trichosporon asahii, Trichosporon cutaneum, Trichosporon inkin, Trichosporon mucoides*.

Non-limiting examples of other pathogenic microorganism include *Acanthamoeba* and other free-living amoebae, *Aeromonas hydrophila*, *Anisakis* and related worms, *Ascaris lumbricoides, Bacillus cereus, Campylobacter jejuni, Clostridium botulinum, Clostridium perfringens, Cryptosporidium parvum, Cyclospora cayetanensis, Diphyllobothrium, Entamoeba histolytica, Eustrongylides, Giardia lamblia, Listeria monocytogenes, Nanophyetus, Plesiomonas shigelloides, Salmonella, Shigella, Staphylococcus aureus, Streptococcus, Trichuris trichiura, Vibrio cholerae, Vibrio parahaemolyticus, Vibrio vulnificus* and other vibrios, *Yersinia enterocolitica* and *Yersinia pseudotuberculosis*.

Cancer Treatment and Chemotherapy:

In some embodiments of the present invention, the medical condition is associated with malignant cells and tumors, collectively referred to herein as cancer.

Cancer is a spontaneous, acquired or genetic disease in which mutations violate cell growth and survival pathways. Essentially abnormal tissue growth (neoplasm) develops through a process whereby cancer begins in a single cell and passes its malignant potential to subsequent generations of cells. A carcinogenic event is usually operated by some external disruptive factors, such as viruses, radiation (such as sunlight, x-rays and radioactive sources which emit energy and subatomic particles) and chemical carcinogens, mutagens or teratogens. Mammalian cells have multiple safeguards to protect them against the potentially lethal effects of cancer gene mutations, but when several genes are defective, an invasive cancer develops. Human cancers originate from mutations that usually occur in somatic tissues; however, hereditary forms of cancer exist in which individuals are heterozygous for a germline mutation.

The mutations target three types of genes (cancer genes), namely tumor suppressor genes, oncogenes, and stability genes. Loss-of-function mutations in tumor suppressors and gain-of-function mutations in oncogenes lead to cancer, while loss-of-function mutations in stability genes increase the rates of mutation of tumor suppressors and oncogenes. All cancer mutations operate similarly at the physiologic level: they drive the carcinogenic process by increasing tumor cell number through the stimulation of cell birth or the inhibition of cell-cycle arrest or cell death. The increase is usually caused by facilitating the provision of nutrients through enhanced angiogenesis, by activating genes that drive the cell cycle or by inhibiting normal apoptotic processes.

The most common types of cancer treatment are surgery, radiotherapy and chemotherapy. Radiotherapy is usually used alone or in combination with surgery and/or chemotherapy. Other types of treatments include hormone therapy that is used in combination with surgery and/or chemotherapy for treatment of, for example, androgen-dependent prostate cancer or estrogen-dependent breast cancer.

Cryosurgery uses cold liquid nitrogen or gas argon to destroy abnormal tissue. Relatively new additions to the family of cancer treatments include biological therapy and angiogenesis inhibitors. Biological therapy is based on the stimulation of the body's own immune system, either directly or indirectly, to fight off cancer or to diminish side effects caused by other treatments.

To date, chemotherapy remains the most common and most frequently used in cancer treatment, alone or in combination with other therapies. Currently available anticancer chemotherapies act by affecting specific molecular targets in proliferating cancer cells, leading to inhibition of essential intracellular processes such as DNA transcription, synthesis and replication.

Unfortunately anticancerous drugs are highly toxic, as they are designed to kill mammalian cells, and are therefore harmful also to normal proliferating cells resulting in debilitating and even lethal side effects. Some of these adverse effects are gastrointestinal toxicity, nausea, vomiting, and diarrhea when the epithelial lining of the intestine is affected. Other side effects include alopecia, when the hair follicles are attacked, bone marrow suppression and neutropenia due to toxicity of hematopoietic precursors. Therefore the effectiveness of currently used anticancerous drugs is dose-limited due to their toxicity to normal rapidly growing cells.

One of the contemporary approaches in the fight against cancer is engineering of molecular targeted drugs that permeate cancer cells and specifically modulate activity of molecules that belong to signal-transduction pathways. These targets include products of frequently mutated oncogenes, such as k-Ras and other proteins that belong to tyrosine kinase signal transduction pathways. For example, Imatinib (Gleevec®), is the first such drug, approved for treatment of chronic myelogenous leukemia (CML). Imatinib blocks the activity of non-receptor tyrosine kinase BCR-Abl oncogene, present in 95% of patients with CML. Imatinib was found to be effective in the treatment of CML and certain tumors of the digestive tract. Nevertheless, as others, this new compound is not completely specific to its target; therefore side effects emerge, including severe congestive cardiac failure, pulmonary tuberculosis, liver toxicity, sweet syndrome (acute febrile neutrophilic dermatosis), leukocytosis, dermal edemas, nausea, rash and musculoskeletal pain.

Angiogenesis inhibitors are currently investigated for their use in cancer treatment and to date, one anti-angiogenetic drug, Bevacizumab (Avastin®), was approved for the treatment of solid tumors in combination with standard chemotherapy. However, as in all chemotherapeutic drugs, Bevacizumab causes a number of adverse side effects such as hypertension, blood clots, neutropenia, neuropathy, proteinuria and bowel perforation.

In some embodiments, the targeting moiety of the molecular structures presented herein, is responsible for the higher concentration of the molecular structure at the targeted bodily site compared to non-targeted bodily sites, thereby reducing the adverse side effects associated with the toxicity of the anti-cancer drugs attached thereto. In addition, the linking moieties attached the anti-cancer drugs to the molecular structure are selected such that they cleave in conditions that are present at the targeted site more so than in non-targeted sites, thereby releasing the payload of drugs at the targeted site at a higher rate compared to non-targeted sites.

Treatment of cancer is becoming even more complicated, since on top of the many factors that cause tumor formation and the multiple adverse side effects associated with currently available anticancerous agents, there are a myriad of mechanisms by which cells become resistant to unspecific drugs.

Mechanisms of drug resistance include prevention from entering the cells, pumping the drug out of the cells, enzymatic inactivation, prevention of drug activity by mutation or altered expression of the target, and inhibition of biochemical pathways by mutations in oncogenes, tumor-suppressor genes or stability genes.

Many of the most prevalent forms of human cancer resist effective chemotherapeutic intervention. Some tumor populations, especially adrenal, colon, jejunal, kidney and liver carcinomas, appear to have drug-resistant cells at the outset of treatment [Barrows, L. R., "Antineoplastic and Immunoactive Drugs", Chapter 75, pp 1236-1262, in: Remington: The Science and Practice of Pharmacy, Mack Publishing Co. Easton, Pa., 1995]. In other cases, a resistance-conferring genetic change occurs during treatment; the resistant daughter cells then proliferate in the environment of the drug. Whatever the cause, resistance often terminates the usefulness of an anticancerous drug, and the emergence of multidrug resistance (MDR) sadly lead to therapeutic failure in many cancer patients [Liscovitch, M. and Lavie, Y., IDrugs, 2002, 5(4), 349-55].

Many studies have been conducted in order to elucidate the mechanism behind the development of MDR cancer cells. One of the most recognized mechanisms involves the ABC (ATP Binding Cassette) transporter proteins. These proteins are capable of coupling the energy of ATP binding and hydrolysis, so as to transport substrates across a cell membrane. The normal physiological role of these proteins is detoxification and clearance by active secretion of intracellular xenobiotic and other undesired substances out of the cell. Thus, in order to ultimately perform their normal physiological role, nature has designed these proteins capable of extruding a wide scope of molecules.

Due to their recognized activity in multidrug resistance (MDR) in tumor chemotherapy these transporter proteins are widely termed in the art as "MDR extrusion pumps".

The lowered efficacy of chemotherapy is linked to the fact that MDR extrusion pumps are over-expressed in cancer cells, as compared to their expression level in normal cells, and are responsible for pumping chemotherapeutic drugs out of the cell, which reduces the levels of intracellular drug below lethal thresholds regardless of the of nature of the cancer cell and/or the drug.

This mechanism of resistance may account for de novo resistance in common tumors, such as colon cancer and renal cancer, and for acquired resistance, as observed in common hematologic tumors such as acute nonlymphocytic leukemia and malignant lymphomas.

Both the resistance to conventional drugs monotherapy and the toxicity of currently use chemotherapeutic agents, support the rationale for combination drug therapy and the use of agents that can fight MDR. Compounds capable of inhibiting MDR extrusion pumps are known in the art as chemosensitizers or chemosensitizing agents. Combination of drugs with different modes of action may protect normal cells against chemotoxicity [Carvajal, D. et al., Cancer Res., 2005, 65, 1918-1924] or facilitate chemotherapy action on resistant tumors [Molnar, J. et al., Curr. Pharm. Des, 2006, 12, 287-311].

In some embodiments, the molecular structures presented herein is designed to carry a variety of anti-cancer drugs that differ from one another in their mechanism of action. This differential mechanism of action can overcome MDR by simultaneously attacking more than one biological system of the malignant cell, causing death before the cell can respond to the attack by the MDR mechanisms.

In the context of some embodiments of the present invention, the term "cancer" refers, but not limited to acute lymphoblastic, acute lymphoblastic leukemia, acute lymphocytic leukemia, acute myelogenous leukemia, acute myeloid leukemia, adrenocortical carcinoma, AIDS-related lymphoma, anal cancer, appendix cancer, basal-cell carcinoma, bladder cancer, brain cancer, brainstem glioma, breast cancer, bronchial adenomas/carcinoids, Burkitt's lymphoma, carcinoid tumor, cerebellar or cerebral astrocytoma, cervical cancer, cholangiocarcinoma, chondrosarcoma, chronic lymphocytic or chronic lymphocytic leukemia, chronic myelogenous or chronic myeloid leukemia, chronic myeloproliferative disorders, colon cancer, cutaneous T-cell lymphoma, desmoplastic small round cell tumor, endometrial uterine cancer, ependymoma, esophageal cancer, Ewing's sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal tumor (GIST), gestational trophoblastic tumor, glioma of the brain stem, hairy cell leukemia, head and neck cancer, heart cancer, hepatocellular (liver) cancer, Hodgkin lymphoma, hypopharyngeal cancer, hypothalamic and visual pathway glioma, intraocular melanoma, Islet cell carcinoma, Kaposi sarcoma, laryngeal cancer, leukaemia, lip and oral cavity cancer, liposarcoma, lymphoma, male breast cancer, malignant mesothelioma, medulloblastoma, melanoma, Merkel cell skin carcinoma, mesothelioma, metastatic squamous neck cancer, mouth cancer, multiple endocrine neoplasia syndrome, multiple myeloma, multiple myeloma/plasma cell neoplasm, mycosis fungoides, myelodysplastic/myeloproliferative diseases, nasal cavity and paranasal sinus cancer, nasopharyngeal carcinoma, neuroblastoma, non-Hodgkin lymphoma, non-melanoma skin cancer, non-small cell lung cancer, oligodendroglioma, oral cancer, oropharyngeal cancer, osteosarcoma and malignant fibrous histiocytoma, ovarian cancer, ovarian germ cell tumor, ovarian epithelial cancer (surface epithelial-stromal tumor), ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia, pleuropulmonary blastoma, primary carcinoma, primary central nervous system lymphoma, primary liver cancer, prostate cancer, rectal cancer, renal cell carcinoma, renal pelvis and ureter carcinoma, retinoblastoma, rhabdomyosarcoma, salivary gland cancer, Sézary syndrome, small cell lung cancer, small intestine cancer, soft tissue sarcoma, squamous cell carcinoma, stomach cancer, supratentorial primitive neuroectodermal tumor, testicular cancer, throat cancer, thymoma and thymic carcinoma, thyroid cancer, transitional cell cancer of the renal pelvis and ureter, urethral cancer, uterine sarcoma, vaginal cancer, visual pathway and hypothalamic glioma, vulvar cancer, Waldenström macroglobulinemia and Wilms tumor.

Preparation of Molecular Structures:

According to an aspect of some embodiments of the present invention, there is provided a process of preparing the molecular structure presented herein, which includes the following basic steps:

i) binding a targeting moiety to a solid support, typically a particulate resin material as widely used in the art of protein synthesis;

ii) linking a first amino acid to a functional group on the targeting moiety;

iii) attaching a first bioactive agent to a functional group on the first amino acid;

iv) linking a second amino acid to a functional group on the first amino acid;

v) attaching a second bioactive agent to a functional group on the second amino acid;

vi) attaching a third bioactive agent to a functional group on the second amino acid; and vii) detaching the targeting moiety from the solid support to thereby obtain the molecular structure.

An exemplary process, according to some embodiments of the present invention, is exemplified in the Examples section below and illustrated in Scheme 3 presented hereinbelow.

In some embodiments, the process may include the elongation of the peptide chain of the MAAP from two to more amino acids. In such embodiments, the process further includes, instead of attaching the third bioactive agent to the second amino acid:

vi) linking a third amino acid to a functional group on the second amino acid;

vii) attaching a third bioactive agent to a functional group on the third amino acid;

viii) attaching a fourth bioactive agent to a functional group on the third amino acid; and ix) detaching the targeting moiety from the solid support to thereby obtain the molecular structure.

It is noted herein that the construction of a molecular structure, according to embodiments of the present invention, can follow a different sequence of assembly steps, such as the construction of the fully formed MAAP plus active agents followed by linking thereof to the targeting moiety, or the simultaneous attachment of identical bioactive agents to a fully formed MAAP and so on.

According to some embodiments of the present invention, the amino acid residues in the MAAP can be linked to one another via their alpha amino and alpha carboxyl functional groups, or via a functional group on their side chain. For example, a MAAP can be formed by linking three lysine residues such that the first lysine is linked to the second lysine by an amide linking moiety comprising the alpha amino of the first lysine and the alpha carboxyl of the second lysine residue, and by linking the third lysine residue to the second lysine residue by an amide linking moiety comprising the ε-amino group on the side chain of the second lysine and the alpha carboxyl of the third lysine residue.

Figure 2:
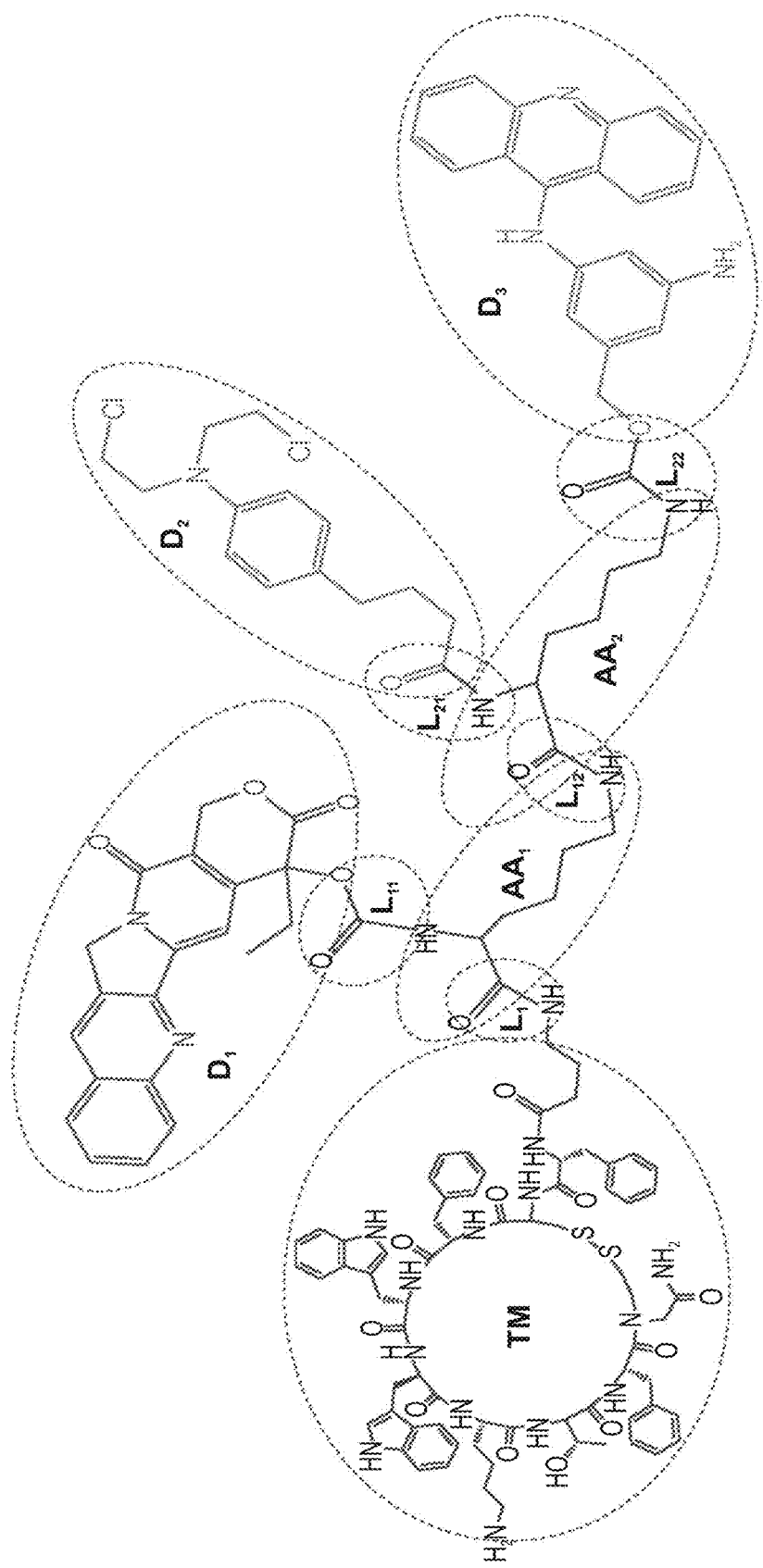
FIG. 2 presents an example of a molecular structure, according to some embodiments of the present invention, wherein the targeting moiety (TM) is a SSTR2 inhibitor variant; the linking moiety $L_0$ is amide; the amino acid residue $AA_1$ is lysine; the inking moiety $L_{11}$ is carbamate; the bioactive agent $D_1$ is camptothecin; the inking moiety $L_{12}$ is amide; the amino acid residue $AA_2$ is lysine; the inking moiety $L_{21}$ is amide; the bioactive agent $D_2$ is chlorambucil; the inking moiety $L_{22}$ is carbamate; and the bioactive agent $D_3$ is 3-(9-acridinylamino)-5-(hydroxymethyl)aniline.

Similarly, the bioactive agents can be attached to the MAAP via alpha functional groups or via side chain functional groups. For example, FIG. 2 presents an exemplary molecular structure, according to some embodiments of the present invention, wherein the first amino acid residue $AA_1$ is linked via its alpha carboxyl group to the targeting moiety (TM) by the amide linking moiety $L_0$, and further the drug $D_1$ is attached thereto via its alpha amino group by the amide linking moiety $L_{11}$, and further the second amino acid residue $AA_2$ is linked thereto via its side chain epsilon amino group by the amide linking moiety $L_{12}$, and so on.

According to some embodiments, some or all the steps of linking the various components of the molecular structure to one another further includes attaching controlled and sequential removal a variety of protection groups on the various functional groups, as commonly practiced in the art of organic synthesis, and in particular in peptide and peptidomimetic compound synthesis.

In general, peptide nucleic acids, oligopeptides, polypeptides, oligonucleotides such as DNA, RNA, and analogs and derivatives thereof, are commonly synthesized using solid phase peptide synthesis (SPPS) techniques, which involve in the case of peptides attaching a first amino acid to a solid phase substrate such as a polymeric resin. The alpha carboxyl group of an additional amino acid is coupled to the terminal amino group of the first amino acid via a condensation reaction. The terminal amino group of the additional amino acid and side chains of both the first and additional amino acid are protected during coupling to prevent unwanted reactions. Subsequent to coupling, the terminal amino group of the additional amino acid itself may be deprotected and coupled with an alpha carbonyl group of another additional amino acid. The process of deprotecting the amino acid attached to the polymer substrate and coupling with an additional amino acid may be repeated many times in order to add more amino acids to the peptide chain. When the desired peptide chain is produced, the peptide chain is deprotected and cleaved from the substrate.

As used herein, the term "protecting group" or "suitable protecting group", refers to amino protecting groups, hydroxyl protecting groups and the like, depending on its location within the compound and includes those described in detail in *Protecting Groups in Organic Synthesis*, T. W. Greene and P. G. M. Wuts, $3^{rd}$ edition, John Wiley & Sons, 1999.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzene sulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4', 8'-dimethoxynaphthylmethyl)benzenesulfonamide (DNMBS), benzylsulfonamide, trifluoromethylsulfonamide, and phenacylsulfonamide.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Examples of Molecular Structures:

Table 3 below presents non-limiting examples of molecular structures comprising at least two amino acids, according to some embodiments of the present invention, by listing the targeting moiety (TM), and first and terminal amino acid residues ($AA_1/AA_n$ respectively), and listing the drug moieties and the linking moieties by which they are attached to the MAAP ($L_{11}/D_1$, $L_{n1}/D_n$ and $L_2/D_{n+1}$), according to the variable of Formula I, wherein $n \geq 2$:

TABLE 3

Formula I $$TM-L_0-\underset{O}{\overset{\overset{\displaystyle D_1}{\overset{\displaystyle |}{\overset{\displaystyle L_{11}}{|}}}}{\underset{\|}{C}}}-AA_1-L_{12} \text{ // } \underset{O}{\overset{\overset{\displaystyle D_n}{\overset{\displaystyle |}{\overset{\displaystyle L_{n1}}{|}}}}{\underset{\|}{C}}}-AA_n-L_{n2}-D_{n+1}$$

| TM | $AA_1/AA_n$ | $L_{11}/D_1$ | $L_{n1}/D_n$ | $L_{n2}/D_{n+1}$ |
|---|---|---|---|---|
| Cyclic RGDfk peptide; c(RGDfk) | aspartic acid/aspartic acid | ester/Camptothecin | Asymmetric anhydride/ Chlorambucil | Primary aromatic carbamate/ Azatoxin |
| Gonadotropin-releasing hormone (GnRH); gonadorelin | glutamic acid/ glutamic acid | ester/Camtothecin | Aromatic ester/ Azatoxin | Primary aliphatic carbamate/ camptothecin |
| Octereotide; Sandostatin | Lysine/Lysine | carbamate with primary hydroxyl/ Azatoxin | Carbamate with secondary hydroxyl/Camptothecin | Primary amide/ Chlorambucil |
| Gonadotropin-releasing hormone (GnRH); gonadorelin | Threonine/D-Threonine | Ester with secondary hydroxyl/ Chlorambucil | Ester with secondary hydroxyl/Melphalan | Primary amide/ Methotrexate |
| Gonadotropin-releasing hormone (GnRH); gonadorelin | Homoserine/ D-Lys | Ester with primary hydroxyl/ Chlorambucil | Primary amide/ Chlorambucil | Primary amide/ Methotrexate |
| Octreotide; Sandostatin | D-Tyrosine/ Lys | Ester with phenolic hydroxyl/Melphalan | Primary amide/ Methotrexate | aliphatic carbamate/ Camptothecin |
| Octreotide; Sandostatin | Homotyrosine/ Aspartic | Ester with phenolic hydroxyl/Chlorambucil | aromatic amide/ amonafide | Phenolic carbamate/ Azatoxin |
| Octreotide; Sandostatin | Homocysteine/ Lys | Thioester/thiol Chlorambucil | aliphatic carbamate/ Taxol | aliphatic carbamate/ Camptothecin |
| Cyclic RGDfk peptide; c(RGDfk) | Cysteine/D-Serine | S-S/6-mercaptopurine (6-MP) | aliphatic carbamate/ deacylated Colchicine | Aromatic carbamate/ Combretastatin A-4 |
| Cyclic RGDfk peptide; c(RGDfk) | D-Lys/D-Lys | Aromatic carbamate/ Combretastatin A-4 | aliphatic carbamate/ Camptothecin | Primary amide/ Chlorambucil |

It is expected that during the life of a patent maturing from this application many relevant molecular structures will be developed and the scope of the phrase "molecular structure" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non-limiting fashion.

Example 1

Synthesis of Molecular Structure Vehicles

The following is an example of a process for affording drug-delivery vehicle in the form of a molecular structure, according to some embodiments of the present invention, which exhibits, as a targeting moiety, a variant of SSTR2 peptide inhibitor (a ligand/inhibitor of somatostatin receptor type 2 encoded by the SSTR2 gene), and three different drug moieties, chlorambucil (CLB), camptothecin (CAMP or CPT) and 3-(9-acridinylamino)-5-(hydroxymethyl)aniline (AHMA).

Materials:

Chlorambucil (CLB), camptothecin (CPT), 3-(9-acridinylamino)-5-(hydroxymethyl)aniline (AHMA), all protected amino acids, resins, and coupling reagents were purchased from Tzamal D-Chem Laboratories Ltd, Petah-Tikva, Israel.

Solvents were purchased from Gas Technologies Ltd, Kefar Saba, Israel.

Other chemicals were purchased from Holland Moran or Sigma-Aldrich.

Cell culture growth medium and all additives were purchased from Biological Industries, Bet-Ha'emek, Israel.

All the cell lines were kindly provided by Prof. Albert Pinhasov (Ariel University, Israel).

All the cell lines were cultured in RPMI medium, which was supplemented with the antibiotics penicillin and streptomycin, and 2 mM glutamine. All the cell cultures were grown at a 37° C. incubator where the environment contained 6% $CO_2$.

Methods:

Electron spray mass spectra (ESI-MS) were obtained using an Autoflex III smart-beam (MALDI), Q-TOF micro or LCQ Fleet™ ion trap mass spectrometer.

HPLC/LC-MS analyses were made using quadruple LC-MS equipped with C18, 2.1×50 mm, 1.8 μm column. In all cases the eluent solvents were A (0.1% FA in $H_2O$) and B (0.1% FA in ACN) and the elution gradient profile was 100% A for first 3 minutes, followed by 5 minutes (from third to eighth minute) during which it reached 100% B, followed by 5 minutes (from eighth to thirteenth minute) of 100% B, followed by two minutes (from thirteenth to fifteenth minute) during which it returned back to A, followed by 2 minutes (from fifteenth to seventeenth minute) of 100% A. The UV detection performed at 254 nm. The column temperature was kept at 50° C. The flow rate was of 0.3 ml/min. The MS fragmentor was tuned on 30 V or 70 V on positive or negative mode.

All HPLC purifications were done via reverse phase on semi-preparative system with dual UV detection at 254 nm and 230 nm. C18, 10 μm, 110 Å, 250×21.2 mm prep column was utilized. The column was kept at room temperature. The eluent solvents were A (0.1% TFA in $H_2O$) and B (0.1% TFA in ACN). A typical elution was a gradient of 100% A to 50% B over 45 minutes at a flow rate of 25 mL/min.

Cytotoxicity of substances was determined by measuring the mitochondrial enzyme activity, using an XTT assay kit (Biological Industries, Bet-Ha'emek, Israel).

All the culture wells in all the experiments contained DMSO at final concentration of less than 0.05%.

Rink amide 4-methylbenzhydrylamine (MBHA) resin was swelled in N-methyl pyrrolidone (NMP) by overnight agitation. The fluorenylmethyloxycarbonyl (Fmoc) group was removed from the resin upon treatment with 20% piperidine in dimethylformamide (DMF), followed by five washes with 10 ml NMP for 2 minutes each.

Building unit bearing carboxyl functionalities (Fmoc-GlyS2(Acm)-OH) was synthesized as described previously [Gellerman, G., et al., *J Pept Res,* 2001. 57(4): p. 277-91], and was activated with benzotriazol-1-yl-oxytripyrrolidino-phosphonium hexafluorophosphate (PyBoP) and N,N-diisopropylethylamine (DIPEA), transferred to the reaction vessel and allowed to react for 1 hour at room temperature, as described previously [Gazal, S., et al., *J Pept Res,* 2001. 58(6): p. 527-39] (see, Scheme 1 below).

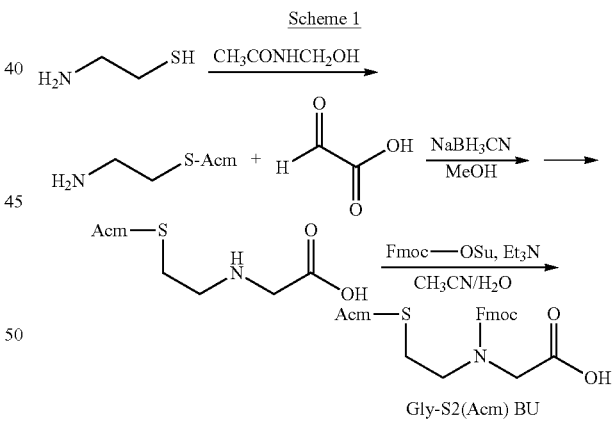

Scheme 1

Subsequently, Fmoc group was removed from the building unit and the linear SSTR2 octapeptide inhibitor was assembled, following stepwise Fmoc deprotection and standard repetitive Fmoc-amino-acid couplings [Gilon, C., et al., *J Med Chem,* 1998. 41(6): p. 919-29]. The cyclization of the acetaminomethyl-cysteine (Cys(Acm)) on the terminal amino acid (AA) at the first coupled building unit (GlyS2(Acm)) was carried out by iodide ($I_2$) followed by agitation at room temperature for 1 hour at ambient atmosphere to afford the disulfide bridge cyclization of the variant of SSTR2 peptide inhibitor, as described elsewhere [Falb, E., et al., *J. Pept. Res.,* 1999, 53(5): p. 507-17] (see, Scheme 2 below).

Scheme 2

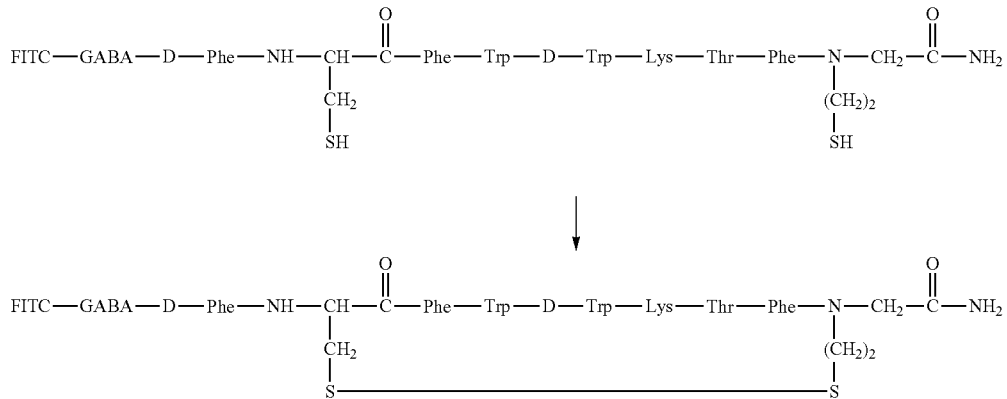

After cyclization, the Fmoc group on the N-terminal Cys was removed followed by repetitive Fmoc-amino-acid couplings of two AAs: Fmoc-D-Phe-OH and Fmoc-GABA-OH.

The synthesis of the entire molecular structure for targeted controlled release of three different bioactive agents (drugs) is illustrated as a general procedure in Scheme 3 below, wherein the empty circle denotes a solid support resin particle, PG denoted a protecting group; TM denotes a targeting moiety; $L_n$ denoted a linking moiety; $AA_n$ denoted an amino acid residue; and $D_n$ denoted a bioactive agent (drug moiety).

Scheme 3

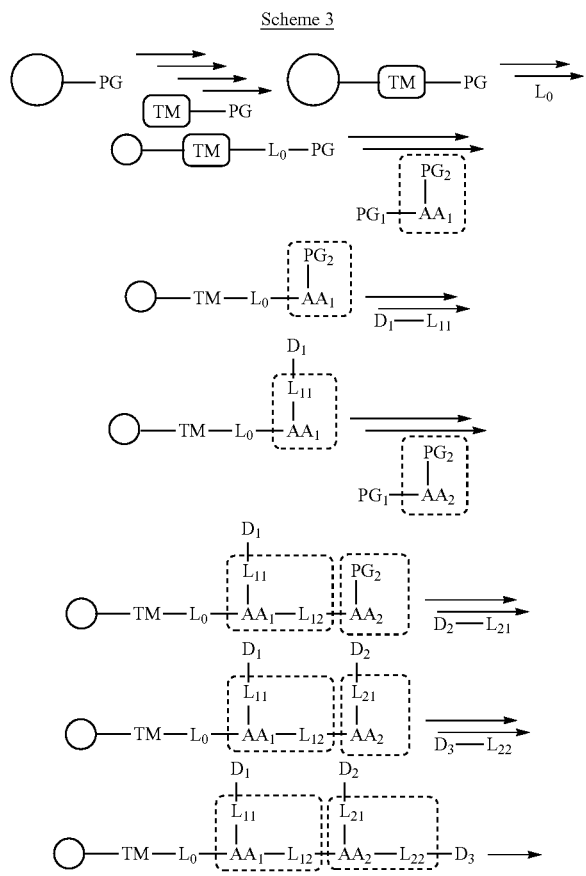

-continued

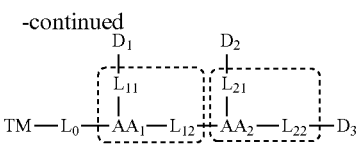

In this non-limiting example, three bioactive agents have been attached to respective functional groups on the amino acids. In this example, the three bioactive agents are the anti-cancer agents chlorambucil (CLB), camptothecin (CPT) and 3-(9-acridinylamino)-5-(hydroxymethyl)aniline (AHMA).

Fmoc chemistry has been employed to afford the bioactive agent attachment, followed by deprotection of the Fmoc group from the Fmoc-GABA-OH and then the orthogonally protected AA Fmoc-(L)Lys(Dde)-OH, which was linked to the resin by standard coupling protocol (PyBOP, DIPEA in NMP). Similarly, the deprotection of the Fmoc group from the Fmoc-(L)Lys(Dde)-OH was followed by coupling of the pre-activated anti-cancer compound CBL (PyBOP, DIPEA in NMP).

Thereafter, the ε-amine Dde protecting group was removed with 2% hydrazine mono-hydrate in DMF afforded the corresponding free ε-amine which was linked to the Fmoc-(L)Lys(Dde)-OH by standard coupling protocol (PyBOP, DIPEA in NMP). Similarly, the deprotection of the Fmoc group from the Fmoc-(L)Lys(Dde)-OH was carried out using 20% piperidine in DMF followed by coupling of the pre-activated anti-cancer compound camptothecin (CPT-_PNP) which was synthesized to exhibit a labile carbonate linker.

The removal of the ε-amine Dde protecting group was carried out using 2% hydrazine hydrate in DMF to afford the corresponding free ε-amine. The latter was subsequently linked to the third pre-activated anti-cancer compound (AHMA_PNP) and then the cyclic peptide was cleaved off the resin, and subjected to purification by preparative HPLC and identified by LC-MS.

FIG. 2 presents an example of a molecular structure, according to some embodiments of the present invention, referred to herein as GGRL11, wherein the targeting moiety (TM) is the SSTR2 inhibitor variant; linking moiety $L_0$ is amide; amino acid residue $AA_1$ is lysine; inking moiety $L_{11}$ is carbamate; bioactive agent $D_1$ is camptothecin; inking moiety $L_{12}$ is amide; amino acid residue $AA_2$ is lysine; inking moiety $L_{21}$ is amide; bioactive agent $D_2$ is chlorambucil; inking moiety $L_{22}$ is carbamate; and bioactive agent $D_3$ is 3-(9-acridinylamino)-5-(hydroxymethyl)aniline.

Example 2

Other Molecular Structures

Figure 3:
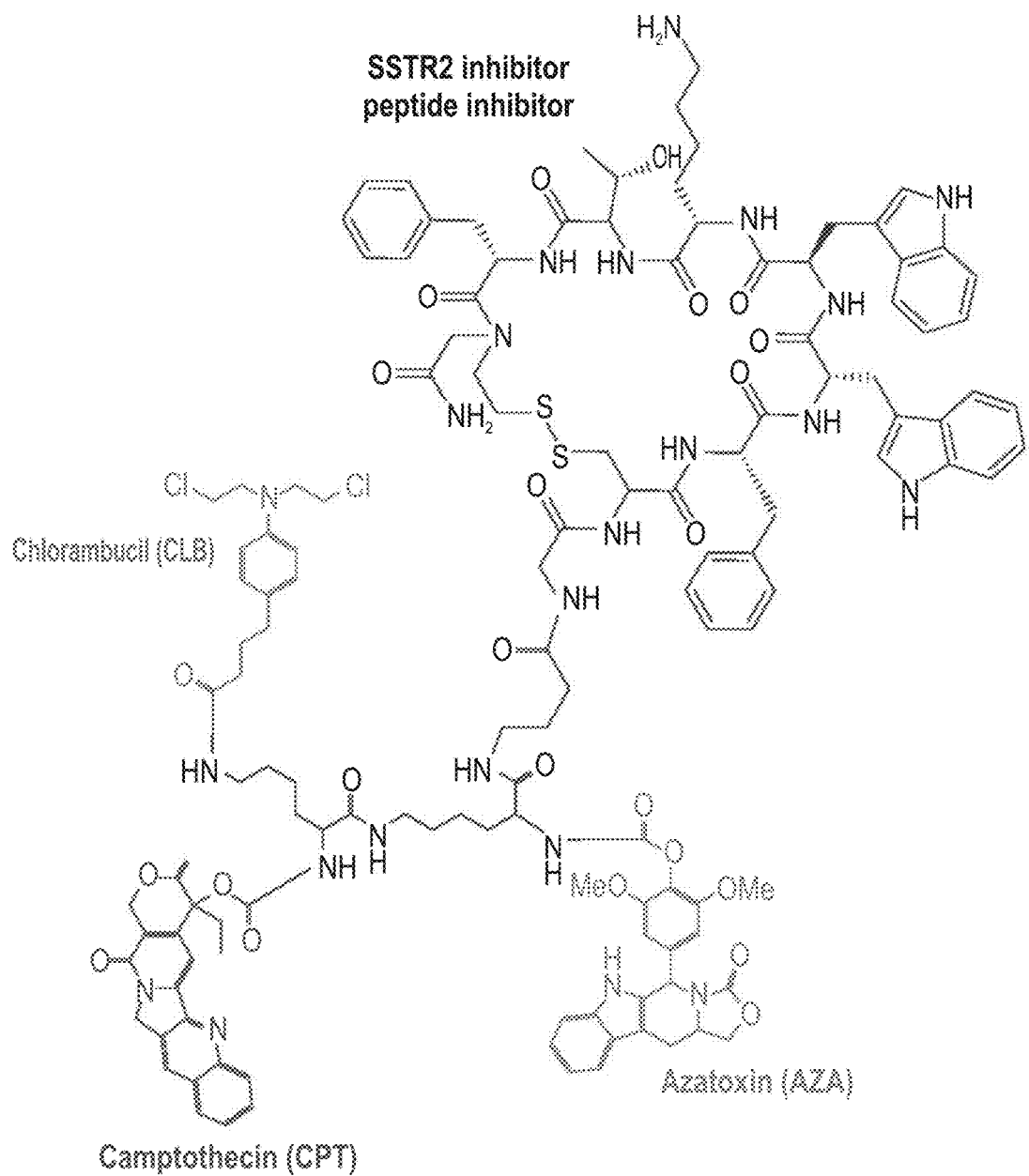
FIG. 3 presents a molecular structure, according to embodiments of the present invention, wherein the targeting moiety (TM) is the SSTR2 inhibitor variant, bearing azatoxin (AZA) as bioactive agent $D_1$, camptothecin (CPT or CAMP) as bioactive agent $D_2$, and chlorambucil (CLB) as bioactive agent $D_3$.

FIG. 3 presents a molecular structure, according to embodiments of the present invention, referred to herein as 9A, wherein the targeting moiety (TM) is the SSTR2 inhibitor variant, bearing azatoxin (AZA) as bioactive agent $D_1$, camptothecin (CPT or CAMP) as bioactive agent $D_2$, and chlorambucil (CLB) as bioactive agent $D_3$, has been prepared following a similar procedure as described hereinabove.

Figure 4:
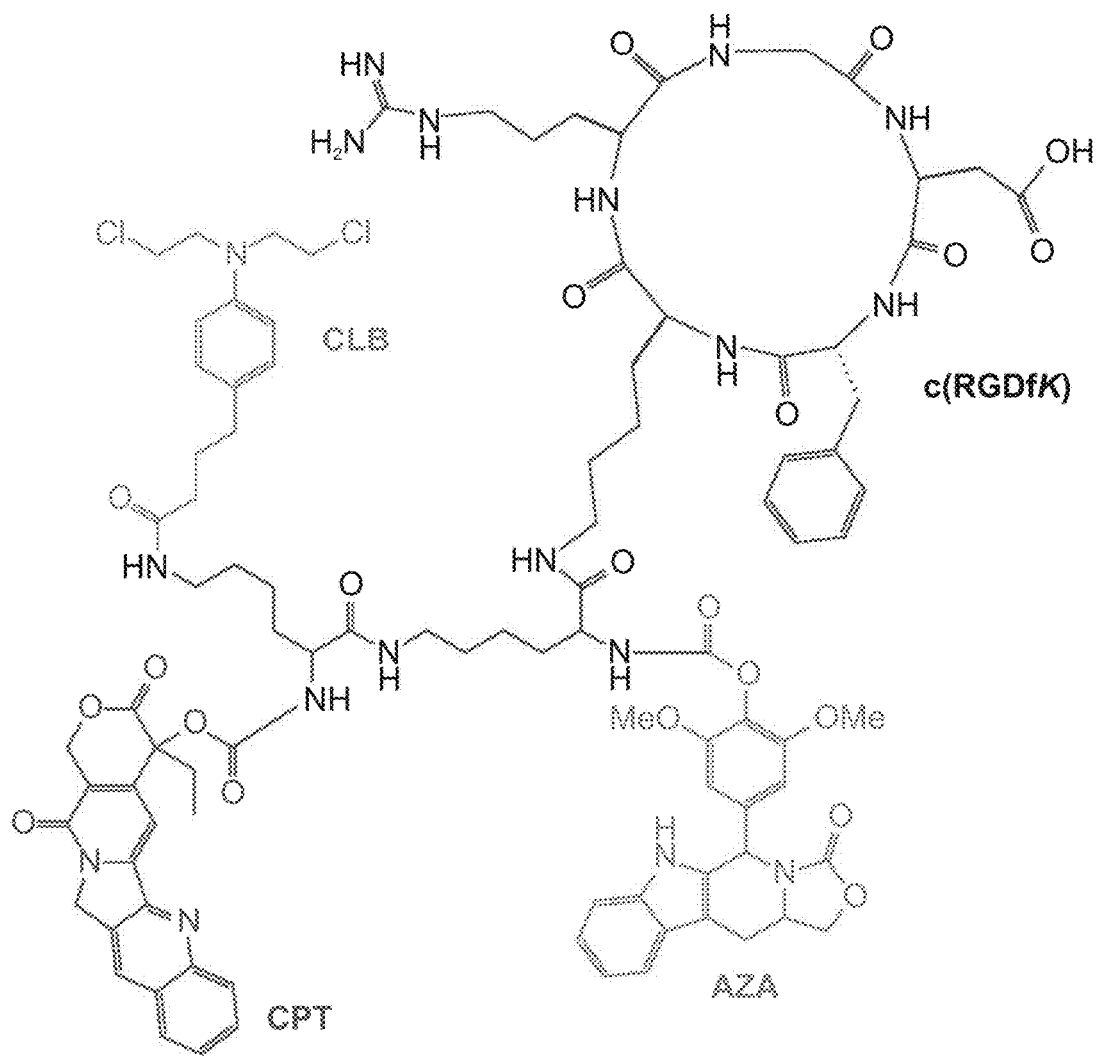
FIG. 4 presents a molecular structure, according to embodiments of the present invention, wherein the targeting moiety (TM) is the c(RGDfk), bearing azatoxin (AZA) as bioactive agent $D_1$, camptothecin (CPT or CAMP) as bioactive agent $D_2$, and chlorambucil (CLB) as bioactive agent $D_3$.
Figure 5:
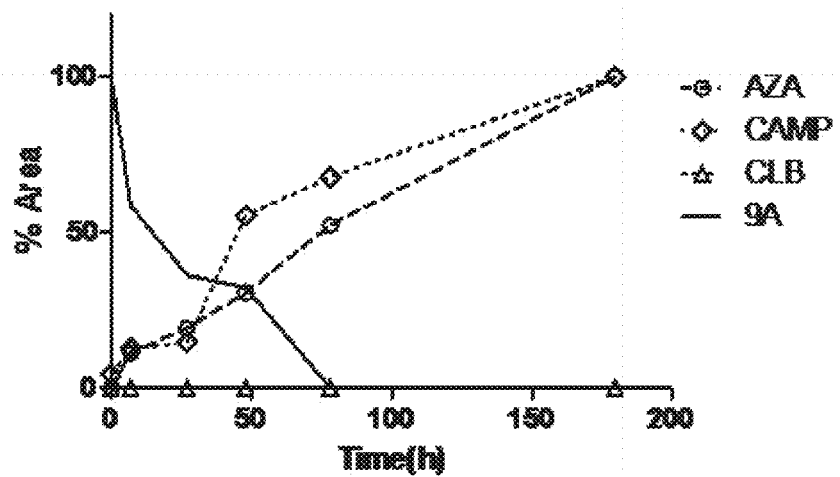
FIGS. 5, 6, 7, 8, 9 and 10 present the results of the drug release study using the molecular structure 9A as described hereinabove, showing the differential release profile, which has been observed for each of the drugs AZA, CAMP and CLB, according to some embodiments of the present invention.
Figure 6:
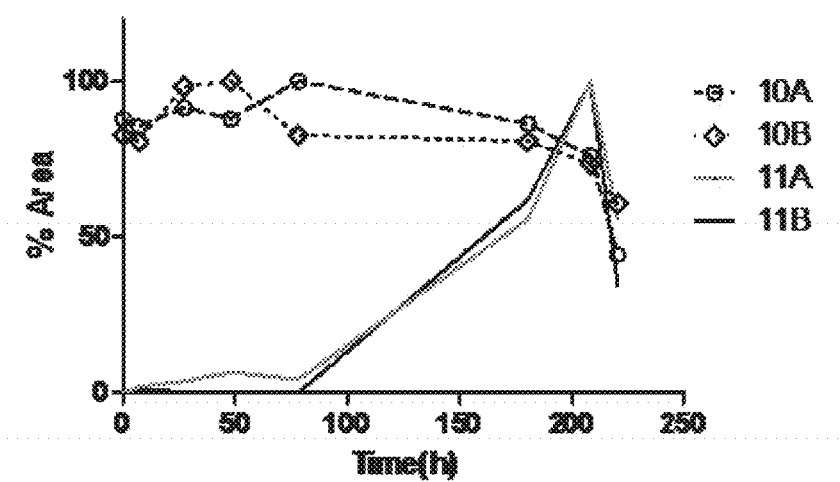
Figure 7:
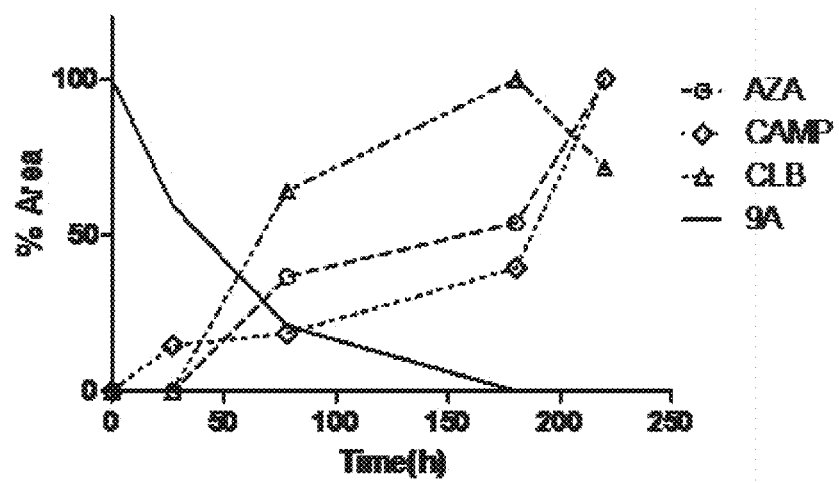
Figure 8:
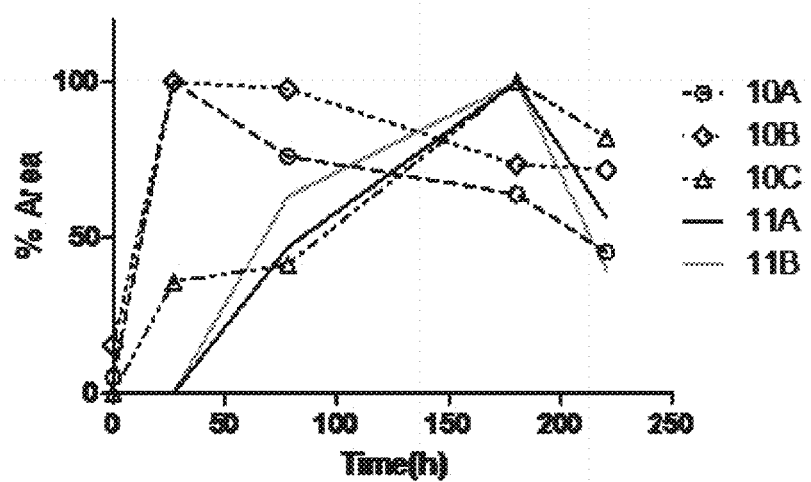
Figure 9:
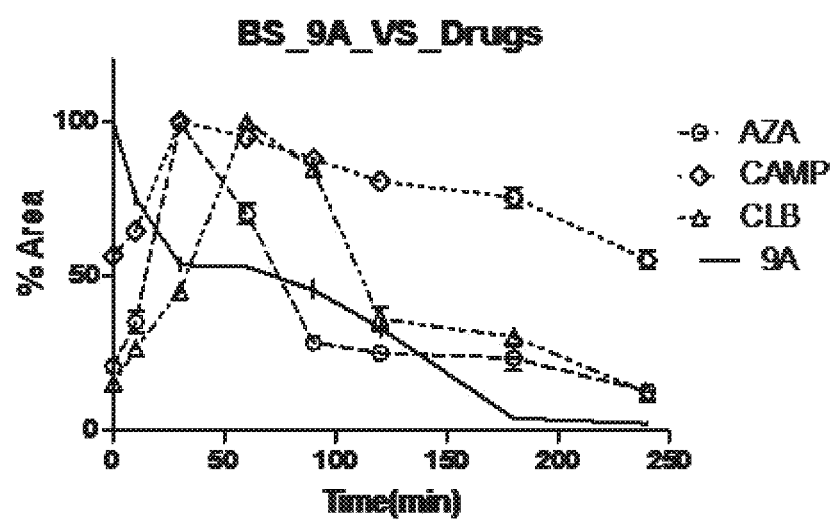
Figure 10:
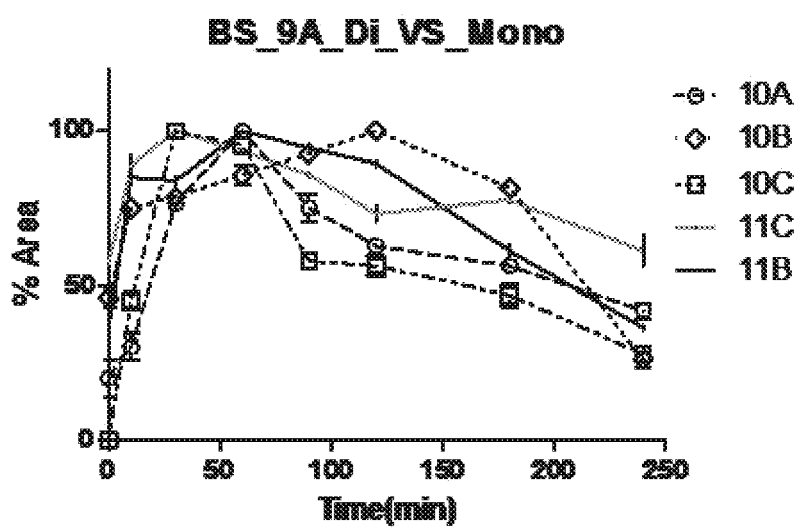

FIG. 4 presents a molecular structure, according to embodiments of the present invention, wherein the targeting moiety (TM) is the c(RGDfk) (binds specifically and with high affinity to $\alpha v \beta 3$ integrin receptors on neovascular blood vessel sections of different major human cancers), bearing azatoxin (AZA) as bioactive agent $D_1$, camptothecin (CPT or CAMP) as bioactive agent $D_2$, and chlorambucil (CLB) as bioactive agent $D_3$, has been prepared following a similar procedure as described hereinabove.

Example 3

Drug-Delivery Mechanism

In order to demonstrate the controllability over the multiple drug-release mechanism of the molecular structures presented herein, the molecular structure 9A was incubated at pH 5, mimicking the microenvironment in some tumors, and at physiological pH 7.4, at 37° C. Aliquots from the stock solutions were extracted at different time intervals and analyzed by LC-MS following the decrease in concentration (nM) of molecular structure 9A (chemical degradation). In addition, the increase in the concentration (nM) from the release of CLB, AZA and CAMP was also followed.

FIGS. 5-10 present the results of the drug release study using the molecular structure 9A as described hereinabove, showing the differential release profile, which has been observed for each of the drugs AZA, CAMP and CLB, according to some embodiments of the present invention.

Example 4

Targeted Chemotherapeutic Drug Delivery

Targeted drug delivery (TDD), an alternative chemotherapy approach, should lower toxicity in normal tissues and increase the efficacy of treatment. Considerable interest has been expressed in receptor-targeted cancer therapy since certain receptors are expressed in higher concentration in cancer cells than in normal cells. Therefore selective delivery of chemotherapeutic agents to target cancer cells is one of the most important and challenging issues in modern chemotherapy.

The study presented below describes the synthesis of five peptide-drug molecular structures based on the S—S bridged backbone cyclic peptide 3207-86, in which the GlyS2 building unit is introduced at the beginning of the assembly (see, Scheme 4 below). Herein and throughout, the term "conjugate" refers to a molecular structure, according to embodiments of the present invention.

Five chemotherapeutic agents, acting through different oncogenic mechanisms, were linked to the core peptide carrier, yielding SST-drug conjugates 1a-e: chlorambucil (CLB), through an amide bond—1a; Topo I inhibitor camptothecin (CPT), through an aliphatic carbamate bond—1b; Topo II inhibitor amonafide with glutaramide linker (AM-Glut), through an amide bond—1c; ABT-751 and combretastatin A4 (COMB) inhibitors of microtubule polymerization that bind β-tubulin on the colchine site, through the aromatic carbamate bond—1d and 1e respectively. The chemo-stability of the conjugates was measured at pH=2, 5 and 7.4. Their bio-stability was assessed in the presence of murine liver homogenate. The degradation products and the released drugs were identified by LC-MS. The conjugates in vitro cytotoxicity effect was evaluated by XTT assay on HCT 116 human colon adenocarcinoma, H1299 human non-small cell lung carcinoma, and TRAMP C2 human prostate cancer cell lines.

Materials and Methods

CAMP, CLB, all protected amino acids, resin and coupling reagents were purchased from Tzamal D-Chem Laboratories Ltd. Petah-Tikva, Israel. COMB, AM-Glut and ABT-751 were synthesized according to literature procedures. All the solvents were purchased from Bio-Lab Ltd. Jerusalem, Israel or Gas Technologies Ltd. Kefar Saba, Israel. All other chemicals were purchased from Holland Moran or Sigma-Aldrich. All the cell lines were cultured in an RPMI medium supplemented with glutamine, 10% fetal bovine serum and with penicillin and streptomycin (100 IU/ml each). The growth medium was supplemented with antibiotics and 2 mM glutamine. The cell culture growth medium and all of its additives were purchased from Biological Industries, Bet-Ha'emek, Israel. All cell cultures were grown at 37° C. in an environment containing 5% $CO_2$. The cytotoxicity of the materials was determined by measuring the mitochondrial enzyme activity, using a commercial XTT assay kit (Biological Industries, Bet-Ha'emek, Israel). All samples contained DMSO at final concentration <0.05%. All the cell lines were obtained from the laboratory of Prof. Albert Pinhasov (Ariel University, Israel) and the Advanced Technologies Center, Sheba Medical Center, Tel Hashomer, Israel.

High Performance Liquid Chromatography (HPLC):

All HPLC purifications were done via reverse phase on ECOM semi-preparative system with dual UV detection at 254 and 214 nm. Phenomenex Gemini® 10 μm C18 110 Å, LC 250×21.2 mm prep column was utilized. The column was kept at room temperature. The eluent solvents were 0.1% TFA in $H_2O$ (A) and 0.1% TFA in ACN (B). A typical elution was a gradient of 100% A to 50% B over 45 min at a flow rate of 25 mL/min. Analytical RP-HPLC was performed on an UltiMate 3000 system (Dionex) using a Vydac C18 column (250×4.6 mm) with 5 μm silica (300 Å pore size). Linear gradient elution (0 min 0% B; 5 min 0% B; 50 min 90% B) with eluent A (0.1% TFA in water) and eluent B (0.1% TFA in acetonitrile: $H_2O$ (80:20, v/v)) was used at a flow rate of 1 mL/min.

Liquid Chromatography-Mass Spectrometry (LCMS):

Electron spray mass spectra (ESI-MS) were obtained using an Autoflex III smart-beam (MALDI, Bruker), Q-TOF micro (Waters) or an LCQ Fleet™ ion trap mass spectrometer (Finnigan/Thermo). HPLC/LC-MS analyses were made using Agilent infinity 1260 connected to Agilent quadruple LC-MS 6120 series equipped with ZORBAX SB-C18, 50×2.1 mm, 1.8 μm column. In all cases the eluent solvents were A (0.1% TFA in $H_2O$) and B (0.1% TFA in ACN) and the elution gradient profile was: 100% A for first 4 min, 8 min (from min 4 to min 12) during which it reached 100% B, 4 min (from min 12 to min 16) of 100% B, 2 min (from min 16 to min 18) during which it returned back to A, and 2 min (from min 18 to min 20) of 100% A. The UV detection was at 254 nm. Column temperature was kept at 50° C. The flow rate was of 0.4 ml/min. The MS fragmentor was tuned on 100V on positive or negative mode.

Synthesis of Peptide-Drug Conjugates:

The synthesis of the cyclic peptide followed a procedure described elsewhere [Kostenich, G. et al., Cancer, 2005, 50, 319-328; Gellerman, G. et al., J Pept Res, 2001, 57, 277-91]. Briefly, in a reaction vessel equipped with a sintered glass bottom, rink amide MBHA resin (substitution level 0.56 mmol/g, 1 gram) was swelled in NMP by agitation overnight. The Fmoc group was removed from the resin by treatment with 20% piperidine in NMP (10 ml) for 15 minutes. This step was repeated twice. After washing the resin with NMP (7×10 nil, 2 min each), Fmoc-GlyS2(Acm)-OH building unit (3 eq, 10.5 mmol, 0.64 g), pre-activated with PyBroP (3 eq, 10.5 mmol, 0.7 g) and DIEA (6 eq, 21 mmol, 0.52 ml) for 4 min at room temperature in NMP (7 ml), was added and was allowed to react for 1 h at room temperature. Following coupling, the peptidyl resin was washed with NMP (5×7 ml, 2 min each). Completion of the reaction was monitored by ninhydrin test (Kaiser test, yellow). Linear peptide was synthesized under standard Fmoc protocol, with 3 equivalents of each amino acid and 3 equivalents of PyBrop as coupling reagent. The deblock mixture was a mixture of 80:20 DMF/piperidine (v/v).

Cyclization Step:

After coupling of Fmoc-Cys(Acm)-OH and NMP wash, the resin was washed with 4:1 DMF/water (3×6.5 ml, 2 min each). A solution of 12 (10 eq, 35 mmol, 1.29 g) in 4:1 DMF/water (10 ml) was added, followed by agitation at room temperature for 1 h to afford the disulfide bridge cyclization. The peptidyl-resin was filtered and washed extensively with 4:1 DMF/water (7×10 ml, 2 min each), DMF (6×10 ml, 2 min each), DCM (6×10 ml, 2 min each), $CHCl_3$ (4×10 ml, 2 min each), 2% ascorbic acid in DMF (6×10 ml, 2 min each), and DMF (6×10 ml, 2 min each). Finally, coupling of the last amino acid, Fmoc-D-Phe-OH after cyclization, afforded the cyclic peptide on the resin.

Coupling of Fmoc-γ-aminobutyric Acid (Linker):

Fmoc-γ-aminobutyric acid (3 eq, 10.5 mmol, 0.49 g) dissolved in NMP (7 ml) was activated with PyBroP (3 eq, 10.5 mmol, 0.7 g) and DIEA (6 eq, 21 mmol, 0.521 ml) for 4 min at room temperature, and then was transferred to the reaction vessel and allowed to react for 1 h at room temperature. After post coupling wash and Fmoc-deprotection (20% piperidine in NMP (10 ml) for 15 min), the peptidyl resin was ready for drug conjugation.

Synthesis of Conjugates 1a and 1c:

The peptidyl resin was washed and CLB or AM-Glut were then coupled to the primary amine through a standard coupling procedure, using 2-fold excess of the anticancer agent. The resin was thoroughly washed with DCM (4×10 ml, 2 min each), MeOH (4×10 ml, 2 min each), DCM (4×10 ml, 2 min each) and dried under vacuum for 20 min. The peptide conjugates were cleaved from the resin using a cocktail solution of 95:2.5:2.5 TFA/TIS/$H_2O$ (13 ml) for 5 min at 0° C. under argon and then 1 h at room temperature under argon. The resin was filtered and washed with the cocktail (10 ml) and TFA (2 ml). The filtrate solution was evaporated to give an oily residue, which solidified upon the addition of cold $Et_2O$. Centrifugation and decantation of the $Et_2O$ layer and repeated treatment with additional cold $Et_2O$ afforded the crude product as an orange solid which was purified by semi-preparative HPLC, yielding conjugate 1a and 1c with amide linkage. For 1a: (52% yield, purity 94%) LC-MS: retention time=11.09 min; HRMS: ESI-MS m/z calculated: 1650.6557, found: 1650.6483 ($MH^+$), calculated: 1672.6409, found: 1672.6432 ($MNa^+$); For 1c: (48% yield, purity 96%) LC-MS: retention time=8.32 min; HRMS: m/z calculated: 1742.7674, found: 1742.7693 ($MH^+$), calculated: 1764.7276, found: 1764.7291 ($MNa^+$).

Synthesis of Conjugates 1b, 1d and 1e:

The peptidyl resin was washed and a DMF/DCM (1:1) solution of premade 4-nitrophenylcarbonate derivative of CPT, ABT-751 and COMB (anticancer agent (1.2 eq.), 4-nitrophenyl chloroformate (1.2 eq.), DMAP (1.2 eq.), DIPA (3 eq.) in DCM, 3 h, room temperature) was added to the exposed primary amine for overnight at room temperature, leading to the corresponding carbamate conjugation site. The resin was thoroughly washed and the peptide conjugate was cleaved from the polymeric support with the TFA cocktail as for 1a. The solvents were removed under a gentle flow of $N_2$ and then the crude was precipitated from $Et_2O$. Purification on semi-preparative HPLC by the method mentioned above provided the final conjugates with carbamate linkage 1b, 1d and 1e. For 1b: (42% yield, purity 95%) LC-MS: retention time=9.11 min; HRMS: ESI-MS m/z calculated: 1759.6759 found: 1759.6792 ($MNa^+$). For 1d: (41% yield, purity 93%) LC-MS: retention time=9.84 min; HRMS: ESI-MS m/z calculated: 1759.6774 found: 1759.6758 ($MH^+$); For 1e: (38% yield, purity 95%) LC-MS: retention time=9.42 min; HRMS: ESI-MS m/z calculated: 1705.7385 found: 1705.7391 ($MH^+$), calculated: 1727.7143, found: 1727.7164 ($MNa^+$).

Stock solutions were prepared by dissolving 5 mg of the substance in 500 µl DMSO.

Chemo-Stability:

Incubation Procedure:

Aqueous stability was determined at pH 2.0 (phosphate buffer), 5.0 (citrate buffer) and 7.4 (PBS buffer). 100 µl of the stock solutions were diluted to 2.5 ml with the desired buffer and then incubated at 37° C. During the incubation period (up to 200 hrs.), aliquots were removed at different time intervals, filtered and analyzed by LC-MS.

Bio-Stability in Liver Homogenate (LH):

Preparation of liver homogenate: Mice were sacrificed by $CO_2$ inhalation euthanasia. The livers were removed, minced, washed three times in cold PBS buffer and homogenized in Tris-HCl buffer, pH 7.4 (wt/3 vol.) by dozen strokes in a Potter-Elvehjem glass tissue grinder. The tissue homogenate was centrifuged at 4° C., 14000 rpm, 20 min. The supernatant was carefully collected (liver homogenate) and used immediately or else stored in liquid nitrogen.

Protein Assay:

Protein concentration was measured using the BCA protein assay with bovine serum albumin as a standard.

Incubation Procedure:

Incubations were conducted in a 37° C. incubator with 2 ml homogenate (equivalent to 6 mg total protein of mouse liver homogenate) per incubation tube. The samples were prepared by adding 50 µl of stock solution to the homogenate (homogenate mixture) at the beginning of the incubation period. Aliquots of the homogenate mixture were removed after 10, 30, 60, 90, 120 and 180 min and then immediately quenched with 2.5 volumes of ethanol. The samples were centrifuged at 14000 rpm for 15 min. Supernatants were collected, filtered and analyzed by LC-MS.

Cytotoxicity Test:

The cytotoxicity of the peptide-drug conjugates was determined by measuring the mitochondrial enzyme activity, using a commercial XTT assay kit. All samples contained DMSO at final concentration <0.05%. Cells were cultured in micro wells at 2-4×10⁴ cells/ml and incubated for 24 h or 72 h. After the first incubation period the cultures were washed and then given fresh medium containing different concentrations of the tested substances. At the end of the second incubation, XTT reagent was added and the cells were re-incubated for additional 2-4 h. During that time the absorbencies in the wells were measured with a TECAN Infinite M200 plate reader at both 480 and 680 nm. The difference between these measurements was used for calculating the % Growth Inhibition (GI) in test wells compared to two controls: cells that were exposed to the medium and solvent, and those that were exposed to a solvent-free medium. All the tests were done in quadruplicates. Each experiment was conducted twice.

Results and Discussion

Synthesis of Conjugates 1a-e:

Bioconjugates with receptor mediated tumor targeting functions are able to deliver chemotherapeutic agents solely to malignant tissues, thus increasing their local efficacy while limiting the peripheral toxicity. Several peptide-drug conjugates employing analogs of the SSTR2 peptide as targeting moiety has already been synthesized and characterized as stated above.[8] Notably, all of these SSTR2 analogs are 'head-to-tail' or S—S 'side chain-to-side chain' bridged cyclic analogs with limited biostability. Therefore, the backbone cyclic peptide SSTR2 analog 3207-86 was used as a targeting moiety in order to increase the stability of the entire peptide drug conjugate. The fully protected cyclic peptide 3207-86 (SSTp) (see, Scheme 4 below) was synthesized on an acid-labile Rink amide MBHA resin (substitution level 0.56 mmol/g, 1 g) using standard Fmoc solid phase peptide synthesis (SPPS).

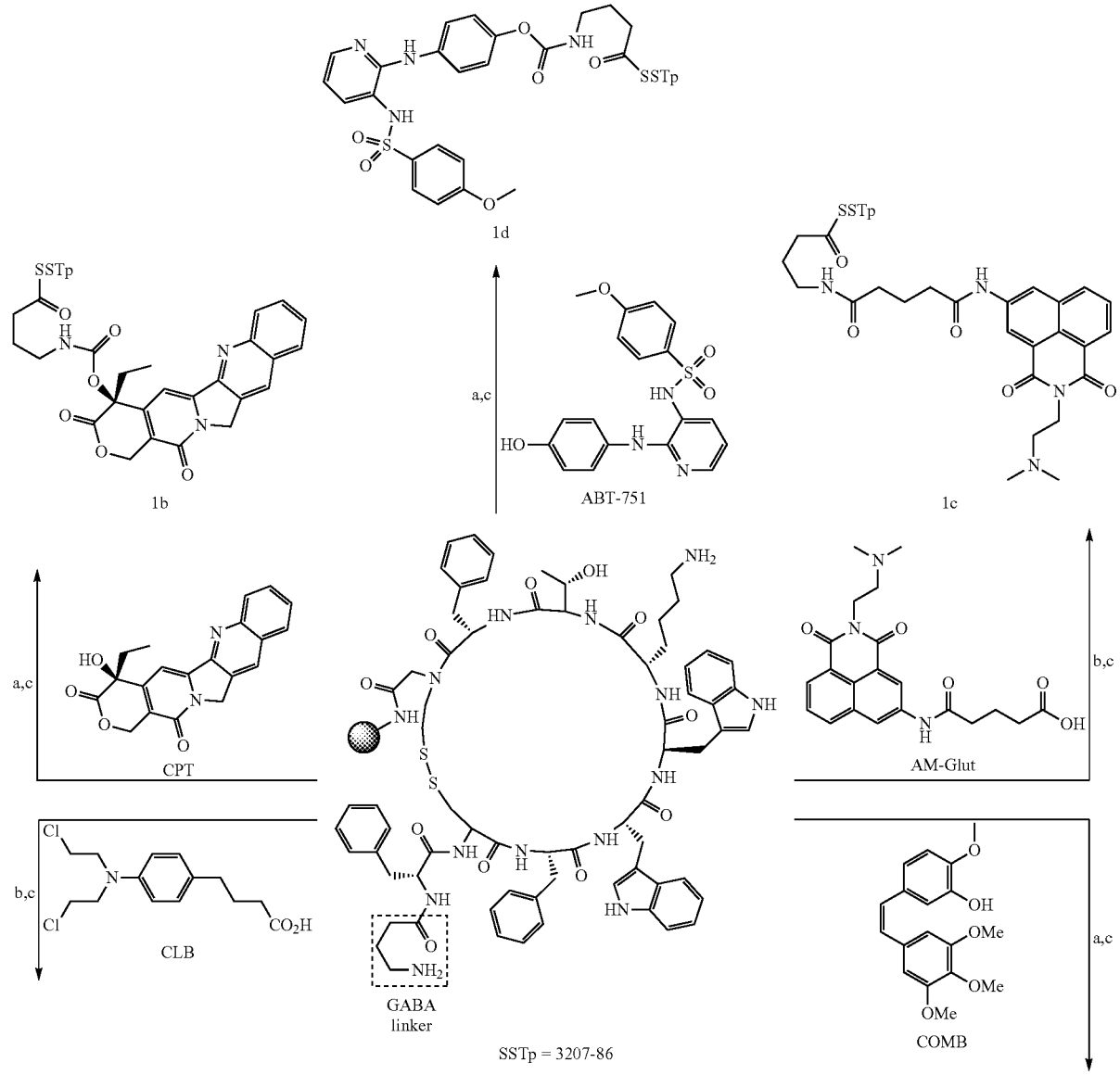

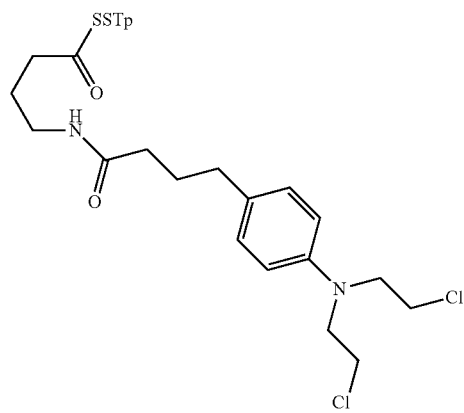

1a

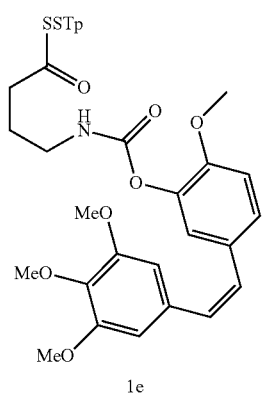

1e a. (i) 4-Nitrophenyl chloroformate, pyridine, 90° C., 1 h; (ii) DMAP (6 eq.) DCM, 0° C.; b. PyBop, DIPA/DMP, 3 hr, rt; c. 95:2.5:2.5 TFA/TIS/H$_2$O, 0° C. then rt, 1 h.

In order to synthesize conjugates 1a-e, first the N-terminal Fmoc group of the GABA linker was removed (20% piperidine in NMP, 10 ml) exposing the primary amine. Consequently, chlorambucil or amonafide glutaramide active esters (CLB (3 eq.) or AM-Glut (3 eq.), PyBop (3 eq), DIPA/DMF, 3 hrs., room temperature) were coupled to the primary amine, obtaining conjugates 1a and 1c respectively with an amide conjugation site. Activated capmtothecin, ABT-751 and combretastatin 4A (CPT, ABT-751 or COMB (3 eq.), 4-nitrophenyl chloroformate (3 eq.), pyridine, 90° C., 1 h; then DMAP (6 eq.) DCM, 0° C.) were reacted with the primary amine, providing conjugates 1b, 1d and 1e with an aliphatic and aromatic carbamate conjugation site respectively. Finally, the on-resin synthesized conjugates were cleaved from the solid support (cold 95:2.5:2.5 TFA/TIS/H$_2$O, room temperature, 1 h), precipitated by diethyl ether, purified by preparative HPLC and characterized by mass spectrometry (see supplementary information).

Stability Profiles:

The stability of the anticancer drug-3207-86 bioconjugates in chemolytic and proteolytic media is of remarkable importance for their therapeutic applications. As the main principle of targeted cancer chemotherapy is the delivery of a chemotherapeutic agent solely to cancer cells, the chemical bond between the 3207-86 and the anticancer drug should exhibit satisfactory stability until the compounds are taken up by the cancer cells for degradation in the lysosomes. This favors the release of the free chemotherapeutic agent or the formation of an active metabolite at the therapeutic site.

Chemo-Stability.

The chemo-stability tests of the conjugates were performed at three different pH values; a physiological pH of 7.4, the slightly acidic pH 5, mimicking the microenvironment in tumors, and the more acidic pH 2.

Figure 11G:
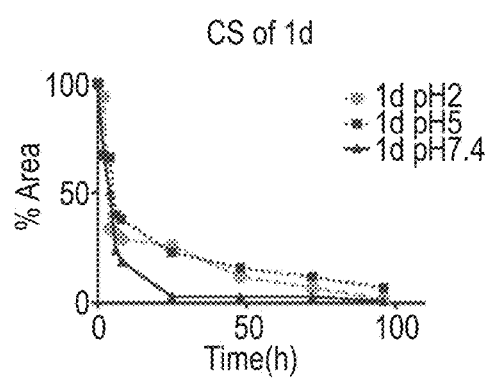
Figure 11H:
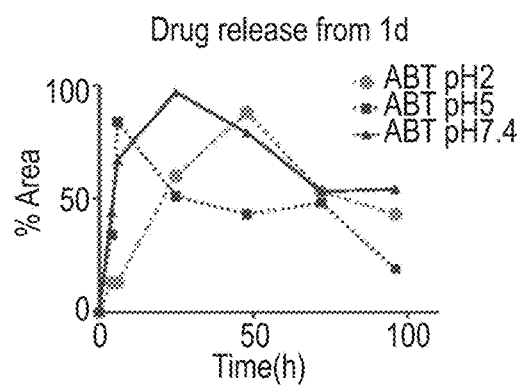
Figure 11I:
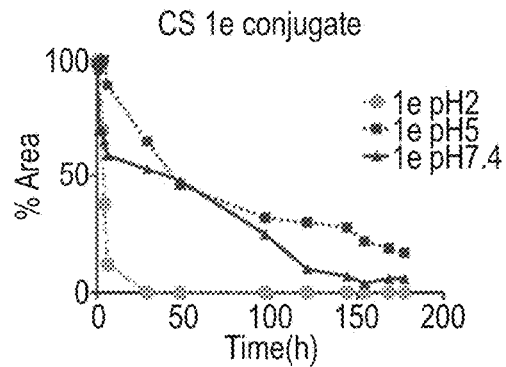
Figure 11J:
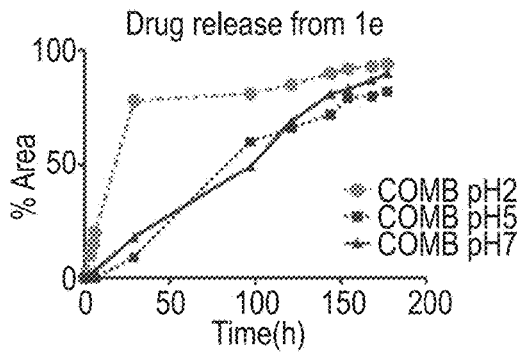

FIGS. 11A-J present the results of the chemo-stability and drug release profiles assays, conducted for conjugates 1a-e at pH 2, 5 and 7.4. Degradation of 1a (FIG. 11A), 1b (FIG. 11C), 1c (FIG. 11E), 1d (FIG. 11G), 1e FIG. 11 (FIG. 11I), and the release of the corresponding drugs: CLB (FIG. 11B), CPT (FIG. 11D), AM (FIG. 11F), ABT-751 (FIG. 11H), and COMB (FIG. 11J). Stock solutions were prepared by dissolving 5 mg of the measured conjugate in 0.5 ml DMSO. 100 μl of the stock solution were diluted to 2.5 ml with the relevant buffer and then incubated at 37° C. Along the incubation period, aliquots were taken at the desired time points and analyzed by LC-MS.

The solutions were incubated at 37° C. and aliquots were taken at desired times and analyzed by LC-MS. For CLB amide conjugate 1a the results show considerable degradation at all tested pH values (FIG. 11A) while CLB release was observed only at acidic pH 2 with $t_{1/2}$=51 h (FIG. 11B). This is consistent with the fact that CLB is more stable at acidic media due to the protonation of its mustard tertiary amine that prevents formation of the reactive aziridinium intermediate. On the other hand, the CPT conjugate 1b with a carbamate bond, exhibited pseudo first-order kinetics CPT release profile at all tested pH values (pH 2, $t_{1/2}$=36 h; pH 5, $t_{1/2}$=37 h; pH 7.4, $t_{1/2}$=58 h). As expected, the degradation rates are consistent with the release of CPT. For instance, faster degradation of 1b at acidic pH (FIG. 11C) is accompanied by faster appearance of the free drug (FIG. 11D). In the case of AM-Glut conjugate 1c conceivable degradation rate was also observed at all tested pH values (pH 2, $t_{1/2}$=48 h; pH 5, $t_{1/2}$=28 h; pH 7.4, $t_{1/2}$=103 h), associated with drug release, while free amonafide exhibited relatively low stability (FIG. 11F) at acidic pH 2. This can be attributed to the chemical instability of the NH$_2$ group at position 3 of amonafide, which is prone to chemical modifications in acidic media.[41] As for ABT-751 peptide conjugate 1d, the rapid degradation at all tested pH values (average $t_{1/2}$=8 h, FIG. 11G) was associated with corresponding release of the drug (FIG. 11H). ABT-751 is linked through the highly degradable aromatic carbamate functionality, which accelerates degradation and drug release rates. Apparently, free ABT-751 also exerts certain degradation behavior due to the presence of the unstable sulfonamide moiety. Finally, Combretastatine 4A (COMB) bioconjugate 1e, which also possesses aromatic carbamate linkage, degrades rapidly in acidic media, especially at pH 2 ($t_{1/2}$=4 min, FIG. 11J), effectively releasing the drug (FIG. 11I). All experiments were monitored by LC-MS against premade standards. The results presented here served as a basis for preparing peptide-multidrug conjugates.

Figure 12A:
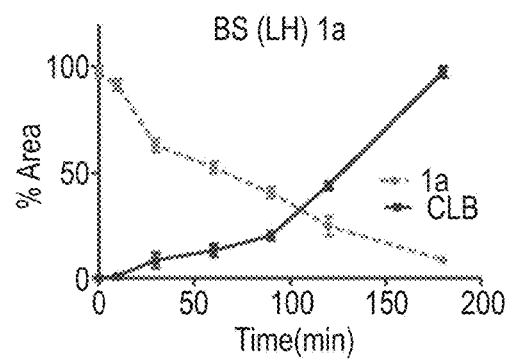
Figure 12B:
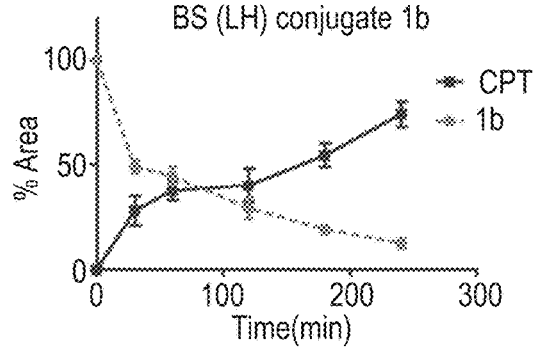

Bio-Stability of Bioconjugates 1a-e:

FIGS. 12A-E present the results of the bio-stability and drug release profiles assays conducted for conjugates 1a-e in LH. FIG. 12A shows the results of the biostability assay of conjugate 1a and release of CLB. FIG. 12B shows the results of the biostability assay of conjugate 1b and release of CPT.

Figure 12C:
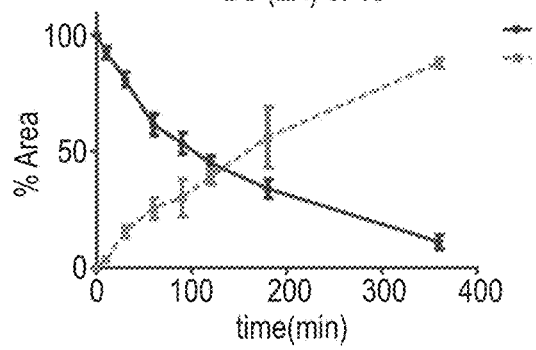
Figure 12D:
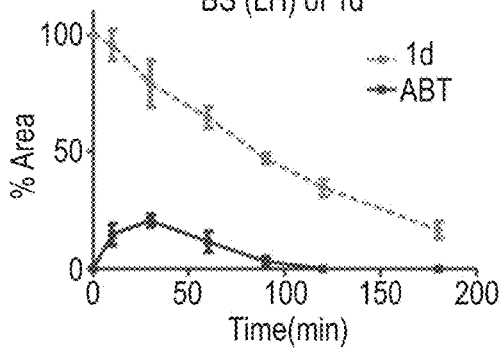
Figure 12E:
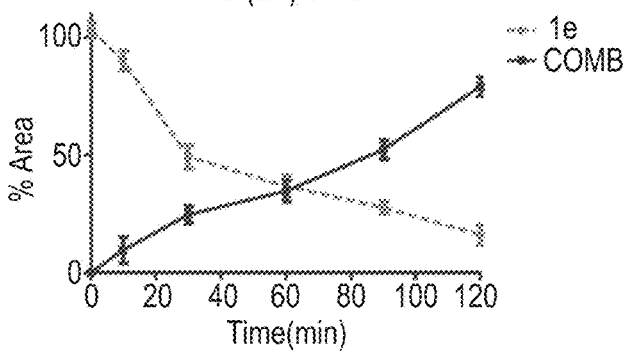

FIG. 12C shows the results of the biostability assay of conjugate 1c and release of AM. FIG. 12D shows the results of the biostability assay of conjugate 1d and release of ABT-751. FIG. 12E shows the results of the biostability assay of conjugate 1e and release of COMB. Stock solutions were prepared by dissolving 5 mg of the measured conjugate in 0.5 ml DMSO. 50 µl of the stock solution were diluted with 2 ml of fresh mouse liver homogenate and then the mixture was incubated at 37° C. Aliquots were collected at 10, 30, 60, 90 and 120 min, mixed with 2.5 volumes of ethanol and centrifuged (14,000 rpm, 15 min). The supernatants were collected, filtered and analyzed by LC-MS Degradation in the murine liver homogenate (LH) and free drug detection was investigated by LC-MS. The compounds, except for conjugate 1d, demonstrated high degradability in the homogenate, resulting in effective and consistent drug release profiling, presented in FIGS. 11A-J. In the case of 1d, the free ABT-751 could hardly be detected due to its rapid degradation (FIG. 12D). This indicates that the free antimitotic ABT-751 could not be released from the bioconjugate in the presence of strong proteolytic enzymes. The CLB conjugate 1a degrades (FIG. 12A, $t_{1/2}$=57 min) with the release of free CLB. The CPT conjugate 1b, possessing biodegradable aliphatic carbamate moiety, degrades more rapidly than CLB amide 1a ($t_{1/2}$=37 min, FIG. 12B) to release free CPT. The aromatic amide AM conjugate 1c presented relatively extended degradation rate ($t_{1/2}$=94 min, FIG. 12C) but with efficient release of free amonafide. The most degradable drug linkage moiety was the aromatic carbamate in 1e, releasing COMB in a relatively short period, ($t_{1/2}$=26 min, FIG. 12E).

The results presented here point at the carbamate and amide functionalities as efficient linkages for drug conjugation to the 8207-86 as targeting moiety. Notably, the aromatic carbamate moiety was found as the most biodegradable in LH. It should be noted that the degradations of peptide-drug conjugates in LH (FIGS. 12A-E) were more rapid compared with those in standard buffers. Such phenomena can accelerate the drug release in liver leading to unfavorable effects on liver tissue. Without being bound by a particular theory, it is understood that such problem can be solved by optimizing peptide-drug linkage chemistry using various bulky secondary or tertiary hydroxyls and amines, S—S linkers etc. Backbone cyclic analogs of 3207-86 presented similar stability in comparison with another SST cyclic peptide analog of therapeutic interest—Sandostatin (Octreotide). In general, all free drugs except ABT-751 were stable in murine LH proteolytic media at the measured time period.

Cell Cytotoxicity:

In order to compare the cytotoxic effects of the conjugates relative to the free drugs, the in vitro cytotoxic effect of the drug bioconjugates 1a-e was determined on SSTR2 overexpressed HCT 116 human colorectal carcinoma, H1299 human non-small cell lung carcinoma and TRAMP C2 human prostate cancer cell lines. The SSTR2 low-expressed HEK-293 (Human Embryonic Kidney 293) cell line was used as a negative control. The study was elaborated over a concentration range of 1-10 µM.

Figure 13A:
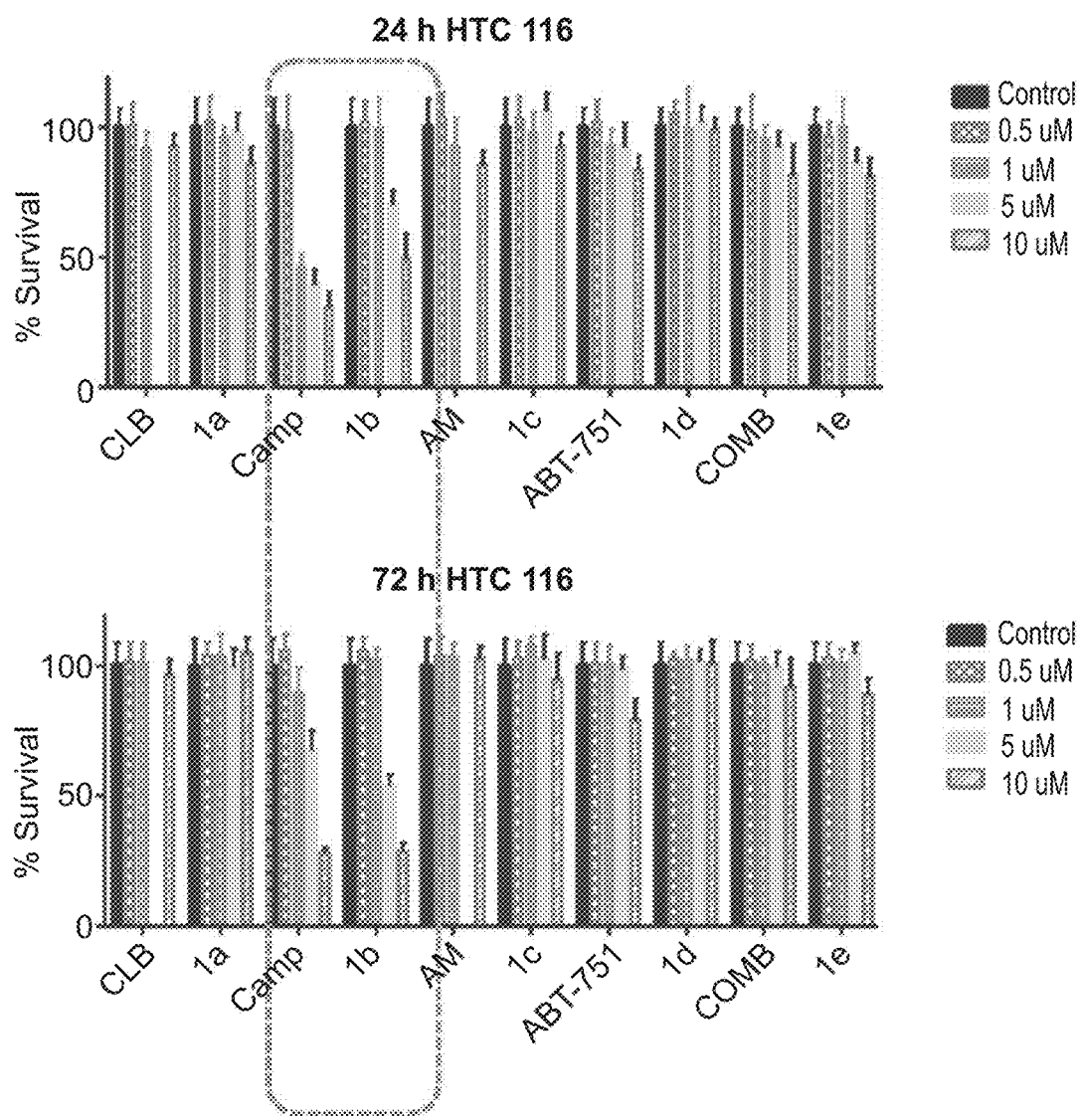
FIGS. 13A-D present the results of the XTT growth inhibition assay conducted for conjugates 1a-e, wherein growth inhibition effect of drug-conjugates versus free drugs was studied on three cell lines with an over-expression of SSTR2 (FIG. 13A. HCT 116.
Figure 13B:
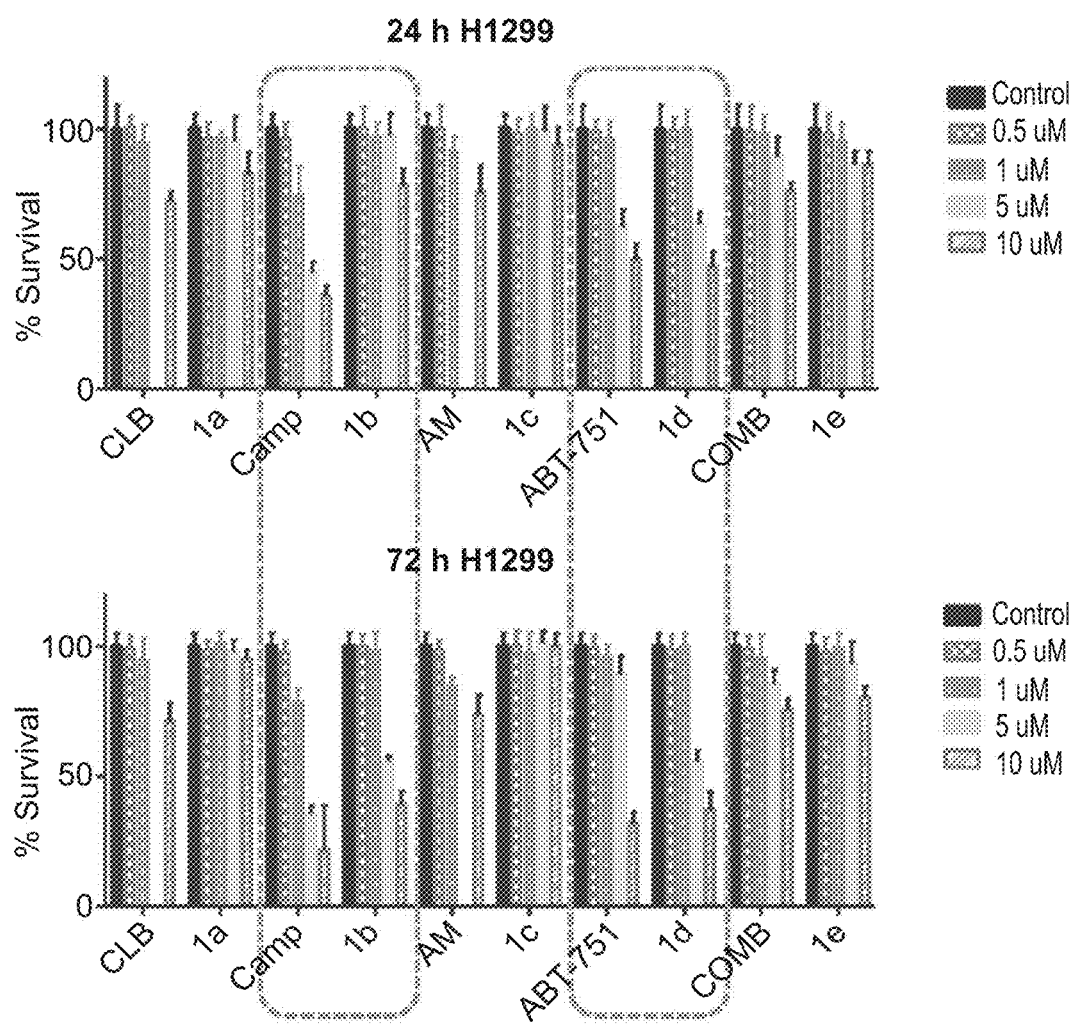
Figure 13C:
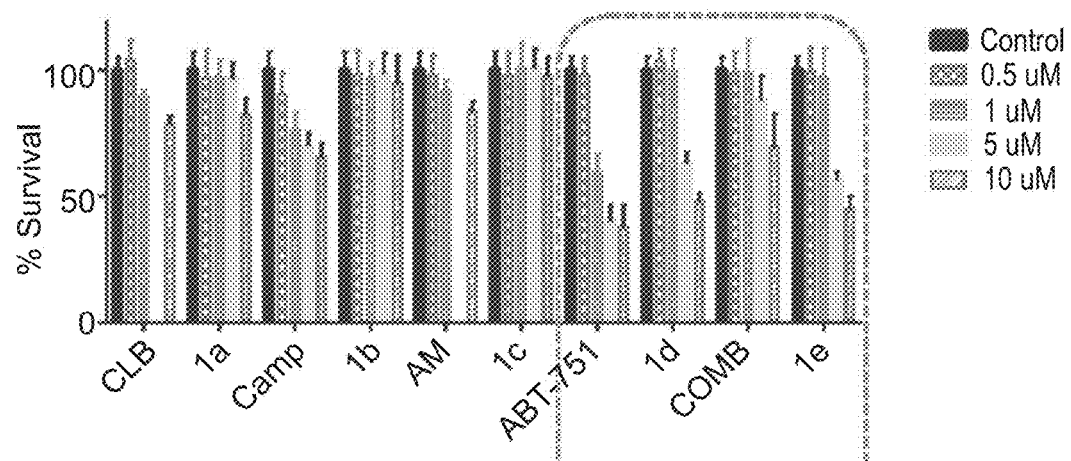
Figure 13C:
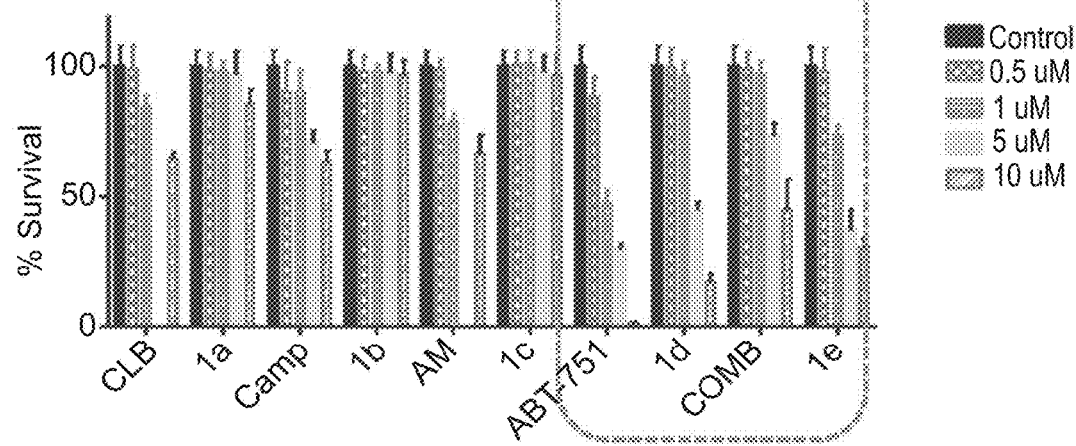
Figure 13D:
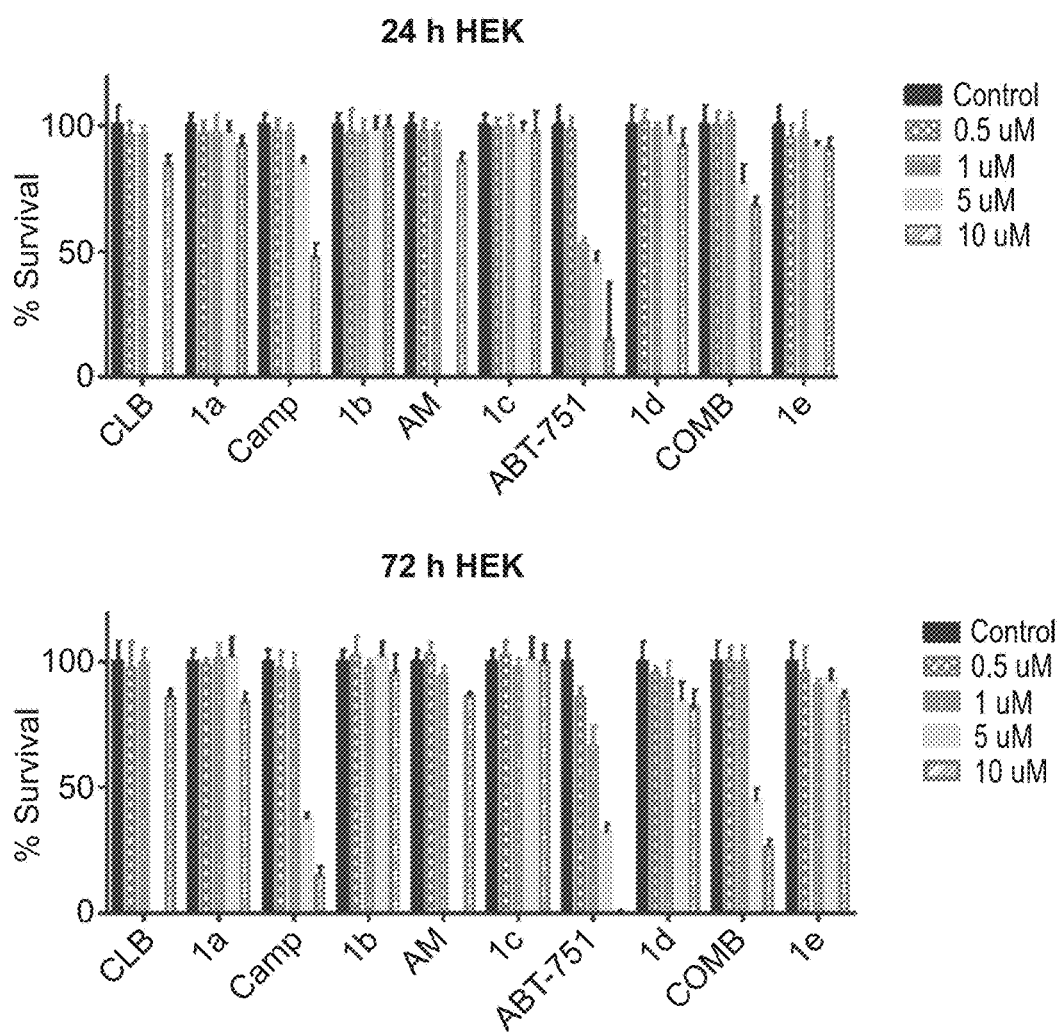

FIGS. 13A-D present the results of the XTT growth inhibition assay conducted for conjugates 1a-e. Growth inhibition effect of drug-conjugates versus free drugs was studied on three cell lines with an over-expression of SSTR2 (FIG. 13A. HCT 116; FIG. 13B. H1299; FIG. 13C. TRAMP C2) against the SSTR2 low expression cell line (FIG. 13D) HEK as negative control. All the cell lines were seeded and allowed to adhere in the wells, after which they were treated with the different compounds in increasing concentrations for 24 and 72 hr. After the treatment, growth inhibition was measured using the XTT assay: The culture medium was replaced by a new one, and then the XTT reagent was added. The wells were incubated for 2-4 hrs. after which the optical density (OD) was measured at 480 and 680 nm. Percentage of growth inhibition for each compound was calculated by comparison of the treated culture versus a control culture (free of any compound). The result shown for each concentration point represents the mean±standard error calculated from two different experiments. In each experiment the compounds were tested in quadruplicates.

Free peptide carrier 3207-86 didn't exhibit cytotoxic effect on HCT 116 and HEK-293 cell lines. In addition, cell penetration capabilities of 3207-86 linked to FITC versus free fluorescein has been studied previously. In this study peptide FITC conjugate presented remarkable accumulation inside the cancer cells as oppose to the free label, outlining the potential of this peptide as a carrier for TDD. During the cytotoxicity experiments, it turned out that drug bioconjugates 1b, 1d and 1e presented targeted but cell selective cytotoxicity. Bioconjugates 1a and 1c were poorly active throughout the study, as was also their free payload (CLB and amonafide). Importantly, all bioconjugates 1a-e were inactive on the negative control HEK cells upon incubation of 72 h (FIG. 13D), as opposed to the free drugs CPT, ABT-751 and COMB, showing overall high cytotoxic effects with $IC_{50}$ values in the low µM range on the tested cell lines including HEK (FIGS. 13A-D).

Thus, the survival of HCT-116 cell line was significantly inhibited after 72 h incubation with the topo I CPT bioconjugate 1b at 10 µM concentration (FIG. 13A). Free CPT presented similar cytotoxicity but was toxic also to HEK as stated above. In the case of H1299, 1b and the antimitotic ABT-871 containing conjugate 1d were most active at 10 µM concentration after incubation of 72 h. Interestingly, despite of the low metabolic stability of ABT-751 in the murine liver homogenate, 1d still had considerable cytotoxic effect, as well as the corresponding free drug (FIG. 13B). This could indicate that the metabolic environment of the cancer cell lines employed in this study and in particular HCT-116 is not 'aggressive' enough to deactivate either 1d or ABT-751 at the tested time period. Next, the cytotoxic effect on TRAMP C2 human prostate cancer cell lines was determined. Here, bioconjugates 1d and 1e, bearing the powerful antimitotic COMB, expressed the most potent targeted therapeutic effect, even more potent than the corresponding free ABT-751 and COMB (FIG. 13C).

This study shows high variability in the chemo- and bio-stability of the drugs linked through various moieties, and therefore strongly support our hypothesis that exposure of drug bioconjugates to cleavage enzymes of various pH dependence, will lead to different kinetics of drug release from these bioconjugates. Efficient SPPS conjugation of cytotoxic drugs, including CLB, CPT, amonafide with glutaramide linker (AM-Glut), ABT-751 and combretastatin A4 (COMB), to the SSTR2 backbone cyclic peptide analog 3207-86 has been demonstrated. In this study, free drugs were non-specifically cytotoxic to both cancer and normal cell lines, while the synthetic drug-bioconjugates exerted selective potency varied among the type of cancer cell lines, and at the same time were indifferent to the negative control HEK cells. Thus, the results from the antiproliferative assays reported here confirm our assumption that the backbone cyclic SSTR2 peptide analog 3207-86 has a potential to be implemented in targeted drug therapy on solid malignancies. A future perspective for multifunctional bioconjugates containing 3207-86 as a targeting moiety could be the attachment of other types of anticancer drugs in different linkage variations, which might act synergistically on the cancer cells and thereby could further enhance the bioconjugate's potency for preclinical targeted cancer therapy assessment.

Example 5

Sequential Drug Delivery

Compact carriers for peptidyl delivery systems (PDSs) loaded with various drugs were synthesized using a simple and convenient solid phase organic synthesis (SPOS) strategy, including semi-orthogonal functional group protection schemes. Each attachment point of the compact carrier can thus be bound to an anticancer agent through a biodegradable covalent link. Chemo- and bio-stability experiments of a model peptidyl platform loaded with three different drugs revealed pH and liver homogenate (metabolic) dependent sequential release behavior. The versatility of this approach will serve to expedite the preparation of PDS libraries. This approach may prove useful for applications suitable for personalized medicine where multiple drug delivery is required in a sequential and controlled fashion.

The present example demonstrates the flexibility of the present invention by generating a molecular structure in the form of an oligopeptide compact carrier, bearing several units of the same or different anticancer drugs. To that end, a short and efficient SPOS method was optimized to afford the rapid generation of dipeptide carriers loaded with various combinations of three anticancer drugs. By extrapolation, this strategy can be expanded to admit higher drug loading on lager oligopeptide carriers. In this context several anticancer drugs working through different anti-proliferative:

(1) Chlorambucil (CLB) is a nitrogen mustard DNA alkylating agent, used as standard chemotherapy treatment for chronic lymphocytic leukemia (CLL). Repeated use of CLB is known to induce drug resistance in CLL patients.

(2) Azatoxin (AZA) is an epipodophyllotoxin-ellipticine hybrid with non-intercalative DNA topoisomerase II (Topo II) inhibitory activity, which failed in clinical trials, but presented promising results in in-vivo testing.

(3) Camptothecin (CAMP) is a potent topoisomerase I (Topo I) inhibitor, showing strong antitumor activity both in-vitro and in-vivo. However, it suffers from poor water solubility and therefore is not orally available.

(4) 3-(9-acridinylamino)-5-hydroxymethylaniline (AHMA) is a potential (Topo II)-mediated anticancer 9-aminoacridine analog. It presents enhanced antitumor efficacy against solid tumors in-vivo, but it failed in clinical trials.

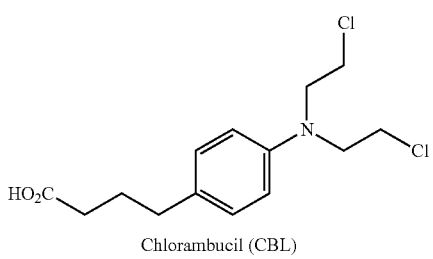

Chlorambucil (CBL)

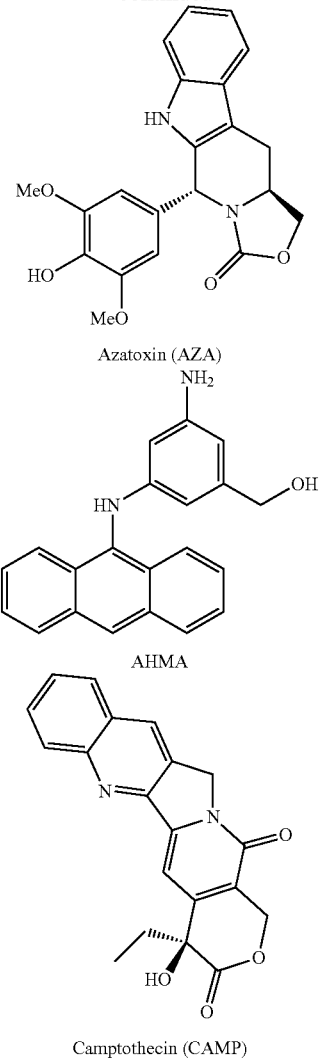

Azatoxin (AZA)

AHMA

Camptothecin (CAMP)

A common key feature shared by the selected active compounds resides in the presence of built-in functional groups that can be exploited to form bio-labile covalent bonds. In the instant study efforts were focused on the optimization of an Fmoc based protocol compatible with the assembly of compact peptidyl carriers, including pre-activation, orthogonal protection/deprotection, and coupling methods. The sequential release of different drugs from a di-Lys compact carrier was characterized, including the cytotoxic activity of the system in a biologically relevant milieu.

Materials:

CAMP and CLB were purchased from Tzamal Laboratories Ltd. Petah Tikva, Israel. All cell lines were cultured in an RPMI medium supplemented with glutamine, 10% fetal bovine serum and with penicillin and streptomycin (100 IU/mL of each). The growth medium was supplemented with antibiotics and 2 mM glutamine. The cell culture growth medium and all of its additives were purchased from Biological Industries, Bet-Ha'emek, Israel. All cell cultures were grown at a 37° C. incubator in an environment containing 6% $CO_2$. The cytotoxicity of the materials was determined by measuring the mitochondrial enzyme activity, using a commercial XTT assay kit (Biological Industries, Bet-Ha'emek, Israel). All samples contained DMSO at final concentration <0.05%.

HPLC purifications were done on an ECOM semi-preparative system equipped with dual UV detection at λ=254 nm and 214 nm and a Phenomenex Gemini® 10 μm C18 110 Å, LC 250×21.2 mm preparative column. The column was kept at r.t. The eluent solvents were 0.1% TFA in $H_2O$ (A) and 0.1% TFA in ACN (B). In a typical elution a gradient of 100% A to 50% B over 45 min at a flow rate of 25 mL/min was applied.

Liquid Chromatography Mass Spectrometry (LCMS) analyses were made using an HPLC Agilent Infinity 1260 equipped with ZORBAX SB-C18, 2.1×50 mm, 1.8 μm column connected to Agilent quadruple 6120 series MS. In all cases the used eluent solvents were 0.1% TFA in $H_2O$ (A) and 0.1% TFA in ACN (B), and the used elution gradient profile was as follows: 100% A for the first 3 min, followed by 5 min of a linear gradient to 100% B (from 3 to 8 min), then 5 min elution with 100% B (from 8 to 13 min), and finally 2 min of a linear gradient back to 100% A (from 13 to 15 min). The column was washed for 2 min with 100% A (from 15 to 17 min) before the next injection. The detector was set at λ=254 nm.

The column temperature was kept at 50° C. The flow rate was of 0.3 mL/min. The MS fragmentor was tuned on 30 or 70 eV on positive or negative mode.

High-Resolution Mass Spectrometry (HRMS) and Electron spray mass spectra (ESI-MS) were obtained using an Autoflex III smart-beam (MALDI, Bruker), Q-TOF micro (Waters) or an LCQ Fleet™ ion trap mass spectrometer (Finnigan/Thermo).

$^1H$ and $^{13}C$ NMR spectra were recorded at 700 and 75 MHz, respectively, in [$D_6$] DMSO, unless otherwise indicated. Assignments in the final products were supported by 2D All chemical shifts are reported with respect to TMS.

Stock solutions chemo-stability studies were prepared by dissolving 5 mg of the tested compound in 500 μl of DMSO.

Incubation procedure: Aqueous stability was determined at pH 2, 5 and 7.4. Aliquots (100 μl) of stock solution were diluted to a total of 2.5 ml with the desired buffer and incubated at 37° C. During the incubation period (up to 160 h) 250 μL portions were drawn at different time intervals, filtered and analyzed by LC-MS.

Bio-Stability in Liver Homogenate (LH) Studies:

Preparation of the LH and assay: Mice were sacrificed by $CO_2$ inhalation euthanasia. The livers were removed, minced, washed three times in cold PBS buffer and homogenized in Tris-HCl, pH 7.4 buffer (wt/3 vol.) by dozen strokes in a Potter-Elvehjem glass tissue grinder. The tissue homogenate was centrifuged at 4° C., 14000 rpm, 20 min. The supernatant was carefully collected (LH) and used immediately or else stored in liquid nitrogen. The concentration of protein was measured using the BCA protein assay with bovine serum albumin as a standard.

Assay incubation procedure: Incubations were conducted in an incubator oven set at 37° C. Each incubation tube contained 2 mL homogenate samples (equivalent to 6 mg total protein of mouse LH). The samples were prepared by adding 50 μL of stock solution to the LH at the beginning of the incubation period. Aliquots (100 μL) of the LH mixture were removed after 10, 30, 60, 90, 120, and 180 min. immediately quenched with 2.5 volumes of ethanol, and centrifuged at 14000 rpm for 15 min. The supernatants were collected, filtered and analyzed by LC-MS.

Cytotoxicity Studies:

The cytotoxicity of the conjugates was determined by measuring the mitochondrial enzyme activity, using a commercial XTT assay kit. All samples contained DMSO at a final concentration <0.05%. Cells were cultured in micro wells at 2-4×10$^4$ cells/mL and incubated for 24 h or 72 h at 37° C. After the first incubation period of 24 h the cultures were washed and then given a fresh medium containing different concentrations of the tested substances. At the end of the second incubation, XTT reagent was added and the cells were re-incubated for additional 2-4 h. During that time the absorbencies in the wells were measured with a TECAN Infinite M200 ELISA reader at both 480 and 680 nm. The difference between these measurements was used for calculating the % viability in test wells compared to two controls: cells that were exposed to the medium and solvent, and those which were exposed to a solvent-free medium. All the tests were done in triplicate. Each experiment was conducted twice.

Synthesis:

General procedure for the SPOS of Lys(Drug$_1$)-Lys (Drug$_2$)(Drug$_3$) platform on Cl-Trt resin:

a. Loading of First Amino Acid, Fmoc-Lys(Dde)-OH:

To 2-chlorotrityl resin (300 mg, 0.336 mmol loading) in a jacketed fritted peptide vessel was added a solution of Fmoc-Lys(Dde)-OH (447 mg, 0.84 mmol) in NMP (3.5 mL), and DIEA (0.439 mL, 2.52 mmol), and the mixture was shaken for 1.5 h. Dry MeOH (1.5 mL) was then poured into the vessel and shaking was continued for an additional 30 min. Usual washings (2×NMP/NMP and 2×DCM/NMP (1:1), 3 mL each) were applied, preparing the resin for the next step.

b. Fmoc Removal:

The Fmoc protecting group was removed by treatment with 20% piperidine in DMF (2×15 min, 5 mL each) and subsequent washings (2×DCM, 2×NMP, 5 mL each).

c. Loading of Azatoxin and Camptothesin:

Azatoxin (274 mg, 0.504 mmol) or camptothesin (251 mg, 0.504 mmol) where dissolved in DMF (3 mL) and NMM (0.234 mL, 1.51 mmol), and then a solution of ClCO$_2$C$_6$H$_4$-p-NO$_2$ (213 mg, 0.504 mmol) in 1 mL DMF was carefully added. The reaction was continued for 40 min at room temperature and the pre-activated compound was added to the resin for coupling and shaken for 1 h at room temperature. Then the resin was washed with 2×NMP/NMP and 2×DCM/NMP (1:1) (3 mL each).

d. Dde Removal:

Dde group was removed by treatment with 2% hydrazine in DMF (2×3 min, 4 mL each) and subsequent washing (2×DCM, 2×NMP, 5 mL each).

e. Loading of Second Amino Acid, Fmoc-Lys(Dde)-OH:

_Fmoc-Lys(Dde)-OH (447 mg, 0.84 mmol) and PyBop (262 mg, 0.84 mmol) were placed in pre-activation vessel with NMP/DCM (1:1) (4 mL). Then DIEA (0.439 mL, 2.52 mmol) was carefully added and the reaction mixture was pre-activated for 2 min, followed by addition to the resin and shaking for 1.5 h. Subsequent washings (2×DCM, 2×NMP, 5 mL each) afforded the peptidyl resin ready for the next step.

f. Loading of Chlorambucil and AHMA-monoglutaramide:

Chlorambucil or AHMA monoglutaramide (156 mg, 0.504 mmol or 216 mg, 0.504 mmol, respectively), DIEA (0.263 mL, 1.51 mmol) and PyBop (262 mg, 0.504 mmol) were pre-activated in NMP/DCM (1:1) (4 mL each) for 2 min at room temperature in the usual manner. Then, the pre-activated Drug was added to the peptidyl resin and shaken for 2 h. After usual workup (2×DCM, 2×NMP, 5 mL each), the resin was dried under nitrogen and transferred to a vial for cleavage.

g. General Procedure for Cleavage of Loaded Peptidy Platforms from Cl-Trt Resin:

A cold cleavage solution, TFA/triisopropylsilane/H$_2$O 95:2.5:2.5) (3 mL), was added to the dried resin in the cleavage vessel. After shaking for 1 h, the solution was collected and the resin was washed with cold TFA (2×1 mL each). The combined TFA solutions were evaporated first under an N$_2$ stream and then in vacuum, followed by the usual work-up (fast purification using solid-phase extraction pack on RP-18, first washed with H$_2$O and then extracted with MeCN, 5 mL each, then leophilization) to give the desired products. Analytical data for 9a: Yield 78%; purity (HPLC) 81%; HRMS (CI) m/z calculated for C69H$_{75}$Cl$_2$N$_9$O$_{15}$ (MH$^+$) 1339.483, found 1340.612; $^1$H NMR (700 MHz, DMSO-d$_6$): δ 0.92 (t, J=7.5 Hz, 3H, C-90), 1.19/1.23 (m, 2H, C-17), 1.3 (m, 2H, C-7), 1.3 (m, 2H, C-16), 1.39/1.4 (m, 2H, C-8), 1.49/1.54 (m, 2H, C-15), 1.59 (quintet, J=7.5 Hz, 2H, C-62), 1.62/1.71 (m, 2H, C-6), 1.87 (t, J=7.5 Hz, 2H, C-63), 2.06, 2.10 (m, 2H, C-89), 2.32 (t, J=7.5 Hz, 2H, C-54), 2.66/2.75 (m, 2H, C-18), 2.75 (dd, J=15.0, 10.5 Hz, 1H, C-32), 2.98/3.07 (m, 2H, C-9), 3.18 (dd, J=15.0, 4.5 Hz, 1H, C-32), 3.68 (m, 4H, C-56, C-57), 3.69 (m, 4H, C-58, C-59), 3.69 (s, 6H, C-43, C-47), 3.77 (td, J=9.0, 5.0 Hz, 1H C-12), 3.93 (td, J=8.5, 4.5 Hz, 2H, C-3,), 4.28 (dd, J=8.5, 4.5 Hz, 1H, C-35), 4.39 (m, 1H, C-31), 4.62 (t, J=8 Hz, 1H, C-35), 5.28 (s, 2H, C-78), 5.42 (d, J=16.5 Hz, 1H, C-86), 5.44 (d, J=16.5 Hz, 1H, C-86), 5.92 (s, 1H, C-29), 6.63 (AA'XX' system, 2H, C-48, C-50), 6.64 (s, 2H C-37, C-41), 6.95 (AA'XX' system, 2H, C-51, C-53), 7.01, (t, J=7.5 Hz, 1H, C-22), 7.08 (s, 1H, C-79), 7.09 (t, J=7.5 HZ, 1H, C-23), 7.32, (d, J=8 Hz, 1H, C-24), 7.45 (t, J=5.5 Hz, NH, C-19), 7.49 (d, J=7.5 Hz, 1H, C-21), 7.67 (t, J=7.5 Hz, 1H, C-66), 7.80 (t, J=7.5 Hz, 1H, C-67), 7.83 (t, J=5.5 Hz, NH, C-10), 7.89 (d, J=8.5 Hz, NH, C-14), 8.09 (d, J=8 Hz, 1H, C-71), 8.15 (d, J=8.5 Hz, 1H, C-68), 8.65 (S, 1H, C-75), 10.93 (s, NH-26). $^{13}$C-NMR (75 MHz, DMSO-d$_6$): 7.43 (C-90), 22.57 (C-7), 22.74$^c$ (C-16), 26.07 (C-32), 27.17 (C-62), 28.43$^d$ (C-17), 28.53$^d$ (C-8), 30.44 (C-89), 30.56 (C-6), 31.97 (C-15), 33.48 (C-54), 34.66 (C-63), 37.87 (C-18), 38.31 (C-9), 41.06 (C-58, C-49), 49.52 (C-31), 50.08 (C-78), 52.12 (C-56, C-57), 53.17 (C-29), 53.81 (C-3), 54.24 (C-12), 55.92 (C-43, C-47), 66.00 (C-86), 68.31 (C-35), 74.63 (C-83), 94.77 (C-79), 104.44 (C-37, C-41), 106.66 (C-28), 111.30 (C-24), 111.73 (C-48, C-50), 117.98 (C-21), 118.66 (C-22), 118.66 (C-81), 121.53 (C-23), 125.77 (C-20), 127.51 (C-66), 127.88$^b$ (C-70), 128.35 (C-71), 128.61 (C-39), 128.90 (C-68), 129.15 (C-51, C-53), 129.63$^a$ (C-52), 129.81$^a$ (C-74), 130.20 (C-67), 130.67 (C-27), 131.46 (C-75), 136.61 (C-25), 137.62 (C-36), 144.24 (C-49), 145.63 (C-76), 146.33 (C-80), 147.83 (C-69), 152.24 (C-73), 152.49 (C-38, C-40), 153.63 (C-45), 153.82 (C-92), 156.22 (C-33), 156.55 (C-82), 167.92 (C-84), 170.89 (C-11), 171.33 (C-64), 173.48 (C-2). (*a, b, c, d—signals with the same superscript designation may be interchanged). COSY, HMQC and HMBC spectra of 9a are depicted in the Supporting Info.

Results and Discussion:

This study demonstrated the implementation of a compact peptidyl carrier unit composed of two Lys amino acids. In principle, a di-Lys structure presents two possibilities. The peptide bond can be formed from either the α-NH$_2$ or the ε-NH$_2$. In any case, the resulting carrier presents three terminal primary amines (one amine group attached to a primary C atom and two attached to secondary C atoms or one amine group attached to a secondary C atom and the other two attached to two primary C atoms) that could be used to form covalent labile linkers with one, two or three units of the same or different anticancer agents. In the case of one or two drugs the remaining free amine groups can serve to improve the water solubility of the PDS, if necessary. Such a strategy could be advantageous when making use of hydrophobic drugs following Ringsdorf's model for drug delivery.

To test the SPOS compatibility of the Lys carrier with the assembly of the different drugs, Rink amide MBHA and Cl-Trt as solid supports was used. The Cl-Trt polystyrene resin represents a particularly advantageous solid support because it is susceptible to cleavage under mild acid conditions, with minimal drug degradation, and also because the cleavage products present a free acid functional group that can be readily conjugated to a desired carrier sequence.

Synthesis of compact carriers Lys-Lys-(CLB)(AZA) 1a and Lys-Lys-(CLB)(CAMP) 1b is presented in Scheme 5 below. Pre-loaded H-(L)Lys(Boc)-OH on Rink amide MBHA (4a) and Cl-Trt resins (4b) were coupled with pre-activated Fmoc-(L)Lys(Dde)-OH, using a standard coupling protocol (PyBOP, NMM in DMF), followed by Fmoc deprotection (piperidine/DMF, 4:1) to afford a solid supported dipeptide with two Lys side chains orthogonally protected (3a and 3b in Scheme 5). Similarly, pre-activated CBL (PyBOP, NMM in DMF) was successfully coupled to 3a and 3b at the free N-terminal amine. Removal of the ε-amine Dde protecting group (2% hydrazine hydrate in DMF) in 3a and 3b afforded the corresponding mono-CBL 2a and 2b which were treated differently in the next drug coupling step. 2a was coupled with pre-activated azatoxin (AZA) whereas 2b was coupled with pre-activated camptothecin (CAMP), both via a labile carbonate linker (ClCO$_2$C$_6$H$_4$-p-NO$_2$, NMM in DMF). After mild acidic cleavage and work up, the desired crude products 1a and 1b, each bearing two different drugs, were obtained in good yield and purity: 1a carries CBL bound through an amide bond and AZA linked as a carbamate, whereas 1b carries the same CBL bound via an amide bond at the same position as 1a but CAMP instead of AZA bound via the carbamate linker. Notably, the free carboxylic acid group on 1b, released after cleavage from the Cl-Trt acid sensitive resin, could serve as an anchor point for further conjugation chemistry, if required. In this study amides and carbamates were used to link between the peptidyl carrier and the loaded drugs. The amide bond is expected to be enzymatically cleaved whereas the carbamate release profile will mainly depend on the aliphatic or aromatic nature of the alcohol involved. In the past it has been established that control samples of amides and carbamates are chemically stable for a period of about a week (160 h) at pH 2 and 5 (at 37° C.) whereas at pH 7.4 the phenolic carbamate (AZA-carbamate, $t_{1/2}$=9 h) degrades faster than the aliphatic CAMP carbamate ($t_{1/2}$=76 h) and the amide bond remains intact.

Scheme 5
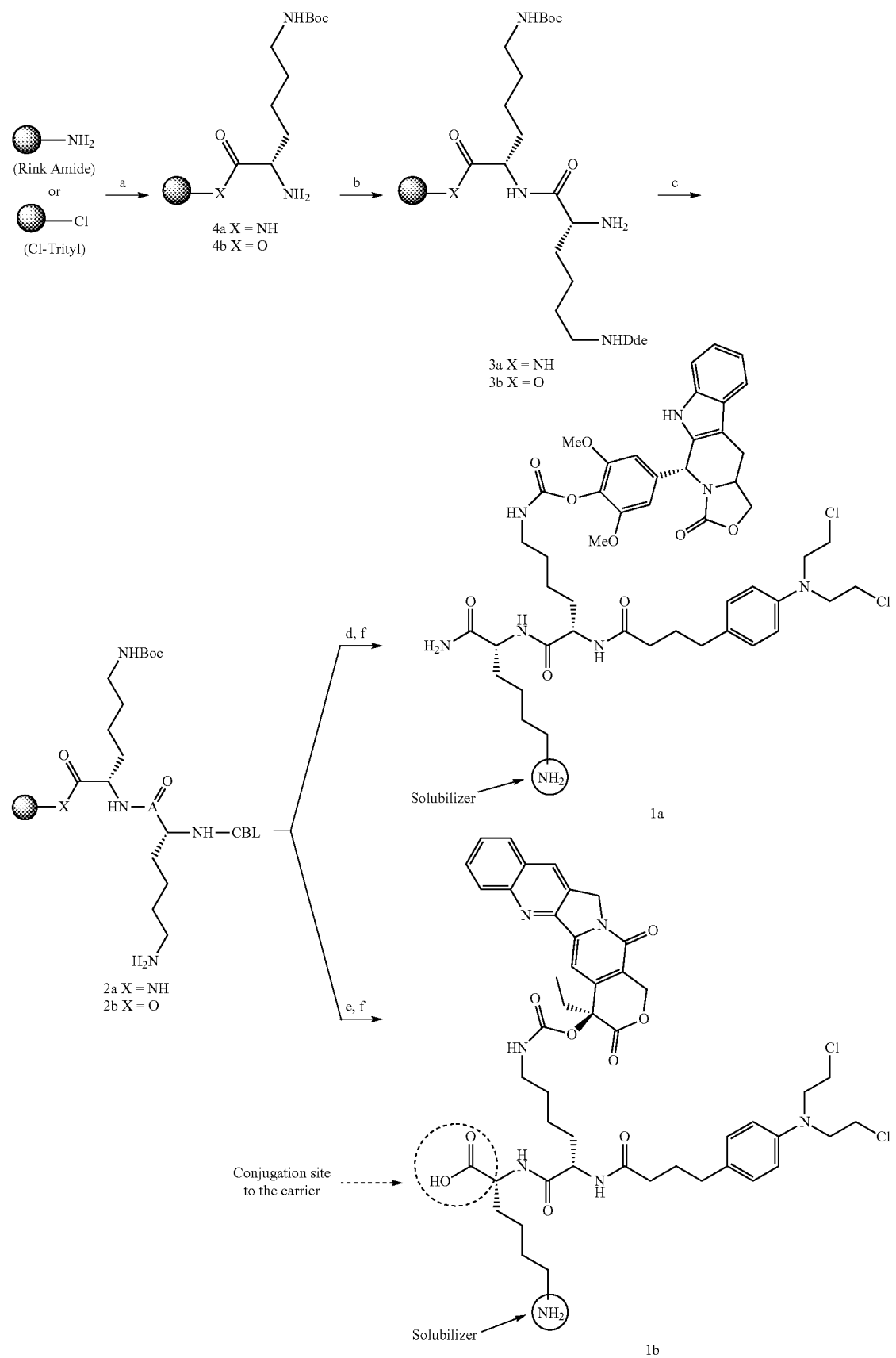

Reaction conditions as seen in Scheme 5 include: a. (i) X=NH, Fmoc (L)-Lys-(Boc)OH, PyBoP, DIEA in DMF, room temperature, 1 hour; X=O, Fmoc (L)-Lys-(Boc)OH, NMM, DCM, room temperature, 1 hour; (ii) 20% piperidine in DMF, room temperature, 20 minutes (twice); b. (i). Fmoc (L)-Lys-(Dde)OH, PyBoP, DIEA in DMF, room temperature, 1 hour; (ii) 20% piperidine in DMF, room temperature, 20 minutes (twice); c. (i) Chlorambucil, PyBoP, DIEA in DMF, room temperature, 1 hour; (ii) 2% $N_2H_4$ in DMF, room temperature, 10 minutes (twice); d. Azatoxin, $ClCO_2C_6H_4$-p-$NO_2$, NMM in DMF, room temperature, 40 minutes then 1 hour, room temperature; e. Camptothecin, $ClCO_2C_6H_4$-p-$NO_2$, NMM in DMF, room temperature, 40 minutes then 1 hour, room temperature; f. TFA/$H_2O$/TRIS (95:2.5:2.5), 0° C., 20 minutes. Product 1a was obtained at 86% yield and 91% purity, and product 1b was obtained at 83% yield and 87% purity.

In cases where the loaded drugs are not particularly hydrophobic and the free amino group is not absolutely required for solubility purposes, this amine functionality could be used to attach a third drug molecule. This third drug can be different than both or equal to any of the drugs already present on the Lys-Lys scaffold.

In order to prepare two compact peptidyl carriers, including two different drugs in a 1:2 ratio, preloaded H-(L)Lys (Dde)-OH on Cl-Trt resin (8) divided in two portions were used, each submitted to parallel coupling schemes with different drug combinations. Scheme 6 presents the synthesis of compact carriers Lys-(AZA)-Lys-(CLB)$_2$ 5a and Lys-(CLB)-Lys-(AZA)$_2$ 5b.

Scheme 6

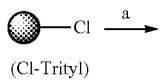

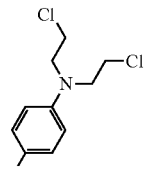

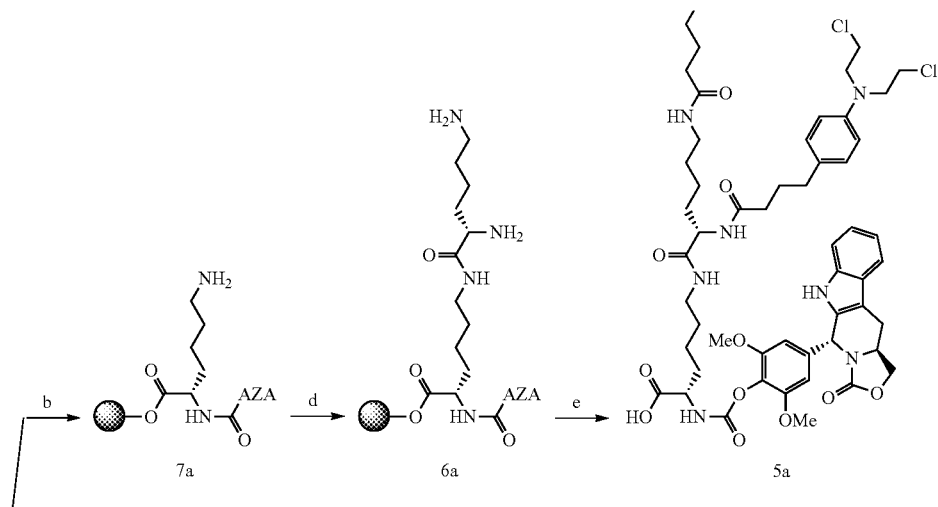

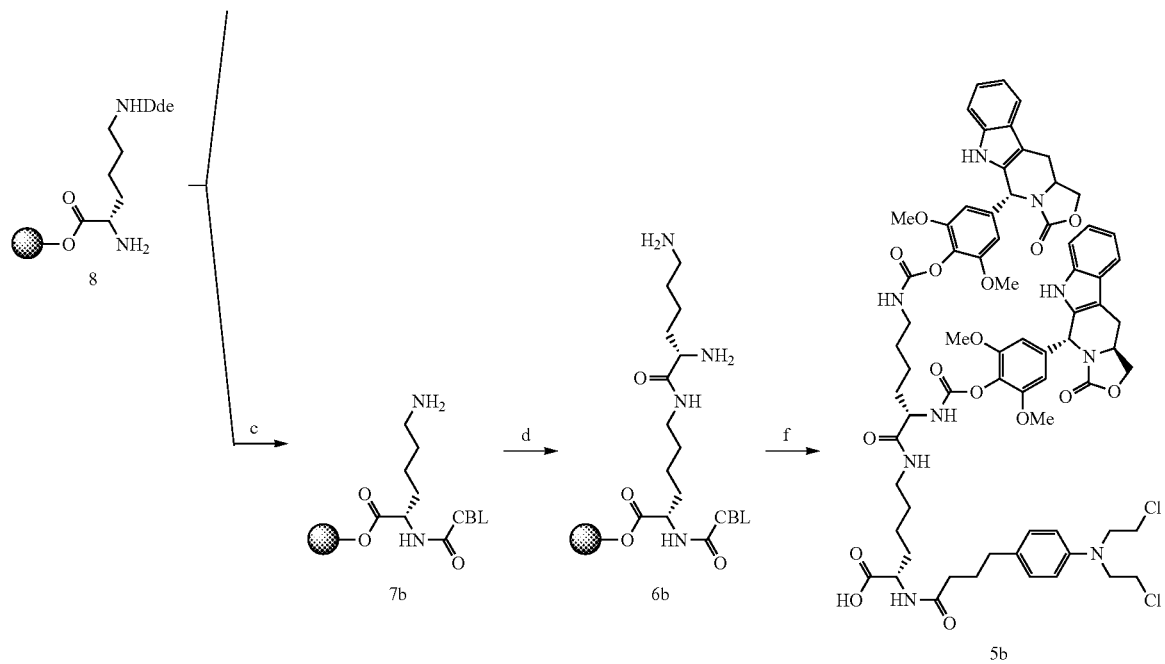

Reaction conditions as seen in Scheme 6 include: a. (i) Fmoc (L)-Lys-(Dde)OHOUR, NMM, DCM, room temperature, 1 hour; (ii) 20% piperidine in DMF, room temperature, 20 minutes (twice); b. (i) Azatoxin, Cl–CO2C6H4-p-NO2, NMM in DMF, room temperature, 40 minutes then 1 hour, room temperature; (ii) 2% N₂H₄ in DMF, room temperature, 10 minutes (twice); c. (i) Chlorambucil, PyBoP, DIEA in DMF, room temperature, 1 hour; (ii) 2% N2H4 in DMF, room temperature, 10 minutes (twice); d; (i) Fmoc (L)-Lys-(Fmoc)OHOUR, PyBoP, DIEA in DMF, room temperature, 1 hour; (ii) 20% piperidine in DMF, room temperature, 20 minutes (twice); e. (i) Chlorambucil (5 eq.), PyBoP, DIEA in DMF, room temperature, 1 hour; (ii) TFA/H2O/TRIS (95:2.5:2.5), 0° C., 20 minutes; f. (i) Azatoxin (5 eq.), ClCO₂C₆H₄-p-NO₂, NMM in DMF, room temperature, 40 minutes then 1 hour, room temperature; (ii) TFA/H2O/TRIS (95:2.5:2.5), 0° C., 20 minutes. Product 5a was obtained at 81% yield and 84% purity, and product 5b was obtained at 80% yield and 82% purity.

The first portion was reacted with pre-activated AZA (ClCO₂C₆H₄-p-NO₂, NMM in DMF) to obtain 7a, where AZA is attached via a carbamate linker at the a-amino group of the carrier precursor, after Dde deprotection. The second portion was first submitted to Dde deprotection and upon coupling with pre-activated CBL (PyBOP, NMM in DMF) led to 7b, where CBL is attached at the α-NH₂ of the carrier precursor via an amide bond. Further coupling of 7a and 7b with pre-activated Fmoc-(L)Lys(Fmoc)-OH employing a standard peptide coupling protocol (PyBOP, NMM in DMF), followed by Fmoc deprotection (piperidine/DMF, 4:1) yielded di-Lys carrier intermediates 6a and 6b respectively, ready to be loaded with two equivalents of a second selected drug. Thus, 6a and 6b were submitted to the second coupling step with a large excess (5 eq.) of the appropriately pre-activated reagent: 6a was reacted with a CBL active ester and 6b with a p-nitrophenol carbonated AZA, to give, after subsequent cleavage and work up, crude 5a and 5b in reasonable yield and purity (Scheme 2). This approach could be easily expanded to other combinations of two drugs in a 2:1 ratio.

In order to install three different drugs in a 1:1:1 ratio an Fmoc/Dde quasi-orthogonal protecting group strategy was used. The synthesis started with the AZA precursor 7a described above, which was now coupled with a pre-activated Fmoc-(L)Lys(Dde)-OH to give, after Fmoc removal, the di-Lys adduct 10 with an AZA moiety attached via a carbamate linker and a free □-amino group set for a second coupling step. To increase the diversity of the products and to show the practical potential of this approach while building small libraries, the resulting compound 10 was divided into three portions and each one was subjected to a different coupling sequence. Final acidic cleavage from the resin afforded the desired compact peptidyl carriers each loaded with a combination of three different drugs 9a, 9b and 9c. Scheme 7 presents the synthesis of trifunctional Lys (AZA)-Lys(CBL)(CAMP) 9a, Lys(AZA)-Lys(CAMP)(CBL) 9b, and Lys(AZA)-Lys(CB L)(AHMA-monoglutaramide) 9c.

Scheme 7
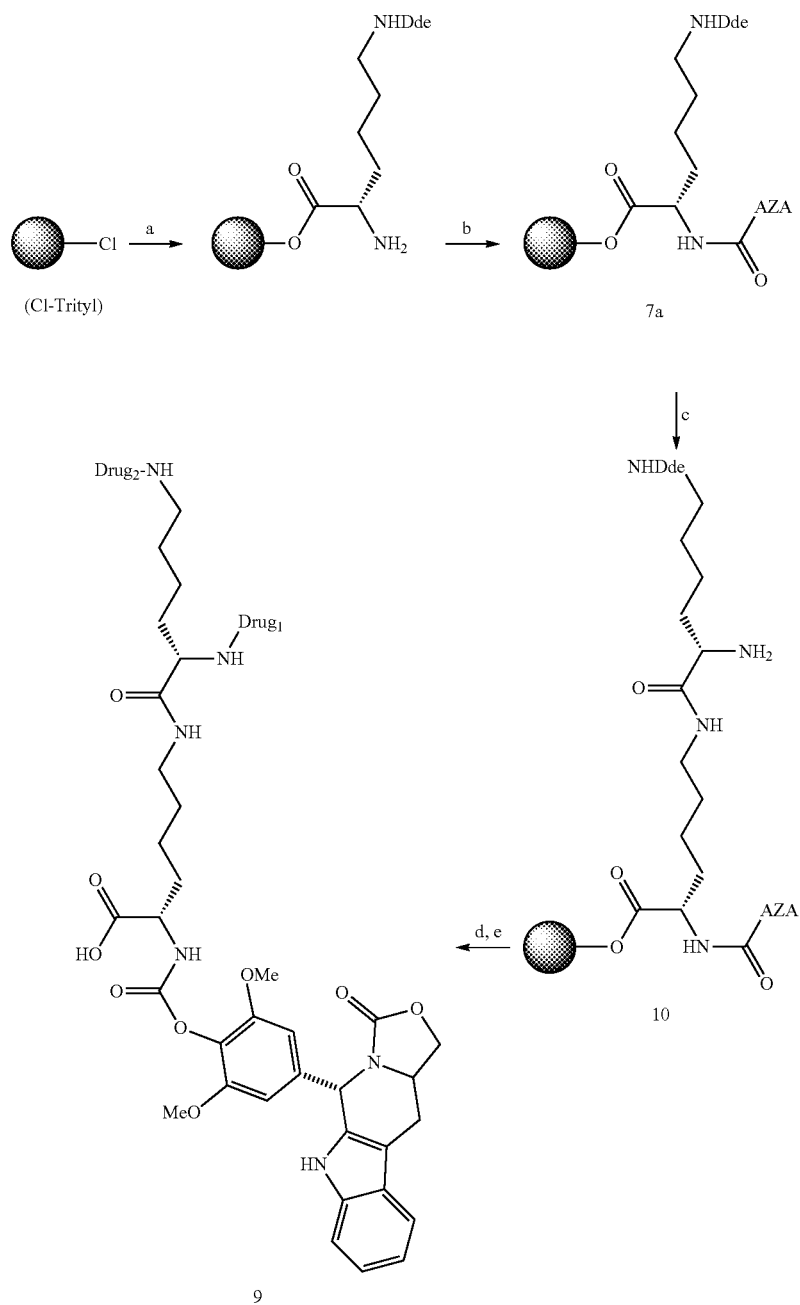
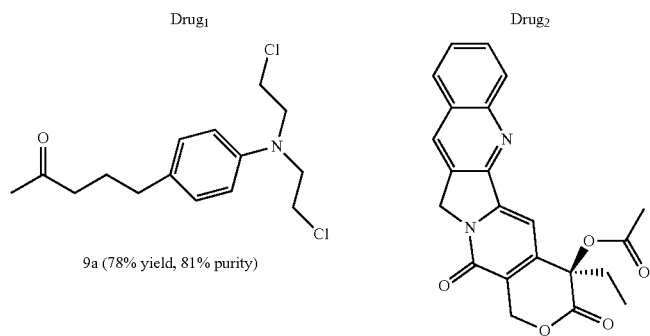

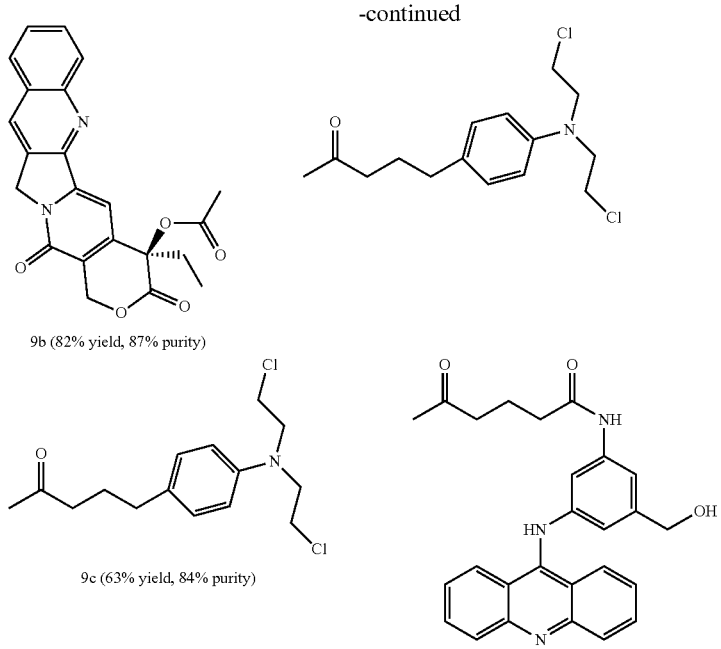

9b (82% yield, 87% purity)

9c (63% yield, 84% purity)

Reaction conditions as seen in Scheme 7 include: a. (i) Fmoc (L)-Lys-(Dde)OHOUR, NMM, DCM, room temperature, 1 hour; (ii) 20% piperidine in DMF, room temperature, 20 minutes (twice); b. (i) Azatoxin, Cl—CO₂C₆H₄-p-NO₂, NMM in DMF, room temperature, 40 minutes then 1 hour, room temperature; (ii) 2% N2H4 in DMF, room temperature, 10 minutes (twice); c. (i) Fmoc (L)-Lys-(Dde)OHOUR, PyBoP, DIEA in DMF, room temperature, 1 hour; (ii) 20% piperidine in DMF, room temperature, 20 minutes (twice); d. for 9a: (i) Chlorambucil, PyBoP, DIEA in DMF, room temperature, 1 hour; (ii) 2% N2H4 in DMF, room temperature, 10 minutes (twice); (iii) Camptothecin, Cl—CO₂C₆H₄-p-NO₂, NMM in DMF, room temperature, 40 minutes then 1 hour, room temperature; for 9b: (i) Camptothecin, ClCO2C6H4-p-NO2, NMM in DMF, room temperature, 40 minutes then 1 hour, room temperature; (ii) 2% N₂H₄ in DMF, room temperature, 10 minutes (twice); (iii) Chlorambucil, PyBoP, DIEA in DMF, room temperature, 1 hour; for 9c: (i) Chlorambucil, PyBoP, DIEA in DMF, room temperature, 1 hour; (ii) 2% N2H4 in DMF, room temperature, 10 minutes (twice); (iv) AHMA-monoglutaramide, PyBoP, DIEA in DMF, room temperature, 1 hour; e. TFA/H2O/TRIS (95:2.5:2.5), 0° C., 20 minutes.

In order to prepare compound 9a, CLB was attached to 10 through an amide bond. Thus, Dde removal and subsequent coupling of CAMP via a carbamate linker afforded the desired Lys(AZA)-Lys(CBL)(CAMP) (9a in Scheme 3). The combination Lys(AZA)-Lys(CAMP)(CBL) (compound 9b) was accomplished by attaching the pre-activated CAMP-carbonate through a labile carbamate linker at the free a-amino group present in 10. After removal of the Dde protecting group, pre-activated CLB to form an amide bond was used, which resulted in the final 9b. An additional example of a third possible combination of three drugs loaded on the di-Lys carrier can be found in 9c. In this last case 10 was coupled to CLB via an amide bond and the Dde protecting group was then removed. At that point, the remaining free amine was connected to AHMA-monoglutaramide through an amide bond, generating Lys(AZA)-Lys(CBL)(AHMA-monoglutaramide) (9c in Scheme 7).

For the simplest case, the carrier could be loaded with three molecular copies of the same drug. For instance, if the drug was CLB it would be linked via three amide bonds. In the case of a different drug like AZA, it would be attached via three carbonate linkers. In addition, other linkers for sequential release can also be envisioned. Some additional degradable linkers suitable for PDS are presented in Scheme 8 below.

Scheme 8

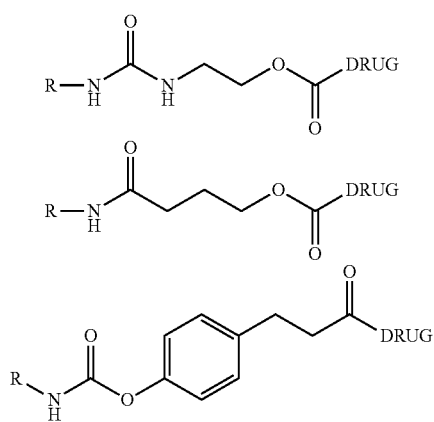

As mentioned before, the carrier could also be loaded with two molecules of one particular drug and a third molecule of a different drug. To illustrate this possibility, compound 5a which carries two CLB and one AZA moiety as well as compound 5b which includes two AZA units and one CLB (Scheme 6) were prepared. In addition three examples of Lys-Lys compact carriers attached to three different drugs 9a, 9b and 9c were prepared (Scheme 7). In principle, considering the selection of four drugs and the three amine available positions presented by the carrier, a library with a total of 20 PDS combinations is theoretically possible (4×3 equal drugs, 12×2:1 ratio of two out of the four drugs and 4×1:1:1 ratio of three different drugs).

The release rate of each drug from the carrier will be dictated by the chemical nature of its corresponding linker. Mixing and matching different amounts of PDSs from these 20 combinations following a simple algorithm to be developed after all relevant ADME parameters are determined, is beyond the scope of this paper and will afford appropriate PDS cocktails suitable for personalized medicine specifically tailored to fit the needs of a given patient at any given stage of treatment.

The applicability of our approach and a preliminary drug release profile of the compact peptidyl carrier was explored using 9a as a model compound. As seen above, 9a is encounter in a potential animal test. To that end, samples of 9a were incubated at pH 2, mimicking stomach conditions, at pH 5 mimicking the microenvironment in tumors, and at physiological pH 7.4, all at 37° C. Aliquots from the stock solutions were extracted at different time intervals and analyzed by LC-MS following the decrease in concentration of 9a (i.e., chemical degradation) and the formation of the dihydroxy derivative 11. In addition, the direct release of the different drugs was also followed based on the increase in the concentration of CLB, AZA and CAMP over time. In this analysis samples of 9a, 11, CLB, AZA and CAMP were used as references. Overall, the HPLC trace presents a very complex mixture of metabolites which could not be exhaustively characterized. Scheme 9 below presented the molecular structure 11.

Scheme 9

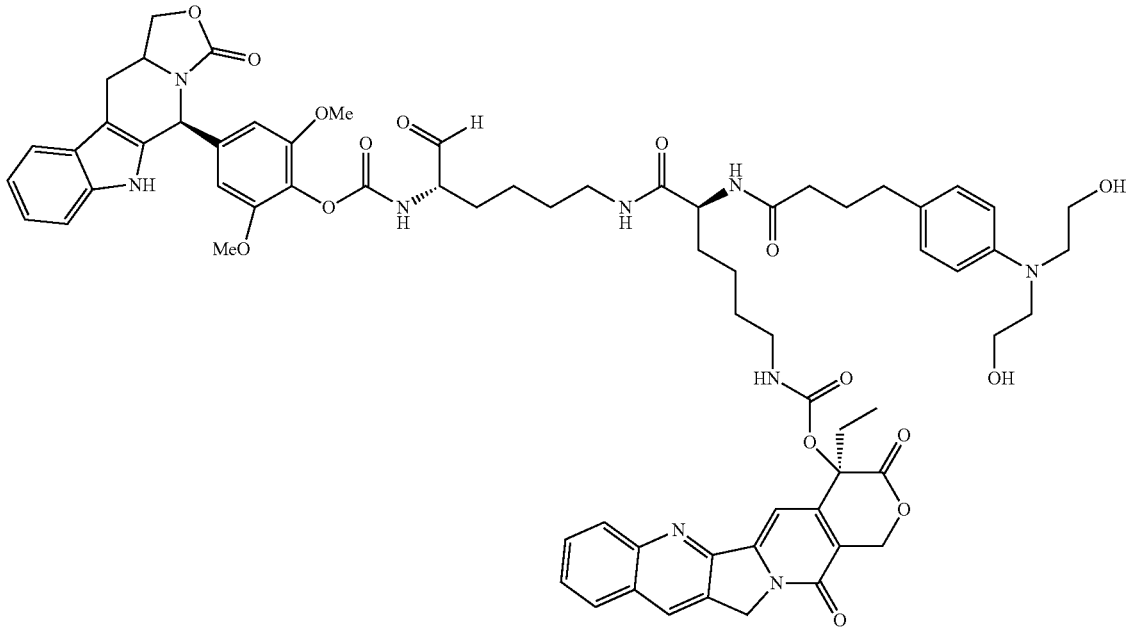

composed of a di-Lys skeleton linked to CAMP via a tertiary alcohol carbamate to a primary C atom, CLB via an amide bond to a secondary C atom, and AZA via a phenol carbamate to a hindered secondary C atom. In order to characterize the background release sequence, chemo-stability studies was initially performed. Samples of 9a were incubated at 37° C., at pH 2, 5 and 7.4. The integrity of the starting molecule 9a was followed by LC-MS for one week. The bio-stability of 9a in a liver homogenate (LH) model test was also followed. LH has been used to mimic the metabolism that would occur to a given drug in mammals, and may serve to assess the metabolic stability of the compound. Finally, the cytotoxic activity of 9a towards HEK293 and Tramp C2 cell lines was determined.

Chemo-Stability Studies:

Peptidyl delivery systems loaded with anticancer drugs are expected to reach their site of action with minimal degradation. The PDS should be stable enough to be absorbed by cancer cells and only then deliver its toxic cargo. Chemo-stability and bio-stability studies may give us a background check for the endurance of our compact peptidyl DDS under the different conditions it is expected to Chemo-stability should account for both the chemical stability of all the loaded drugs and for the resilience of the bio-labile link of each drug to the peptidyl carrier. Among the four chosen drugs, CLB is of particular interest since it is an N-mustard DNA alkylating compound that could be at risk of undergoing hydrolysis before being released at its site of action, was monitored.

Figure 14A:
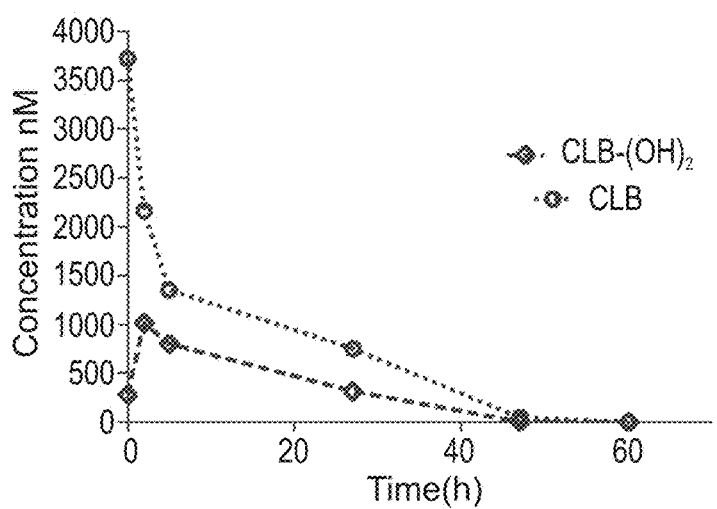
FIG. 14A-C present the results of the chemo-stability tests of CLB and transient formation of the dihydroxy intermediate at different pH values, pH 7.4 (FIG. 14A), pH 5 (FIG. 14B) and pH 2 (FIG. 14C)
Figure 14B:
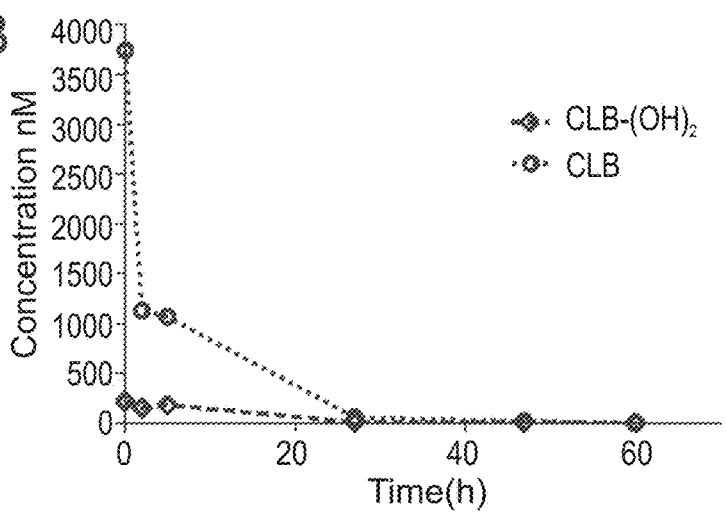
Figure 14C:
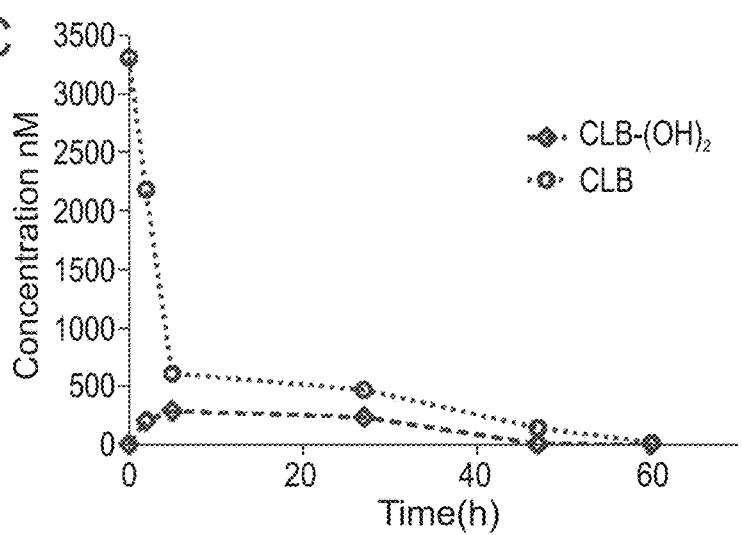

FIGS. 14A-C present the results of the chemo-stability tests of CLB and transient formation of the dihydroxy intermediate at different pH values, pH 7.4 (FIG. 14A), pH 5 (FIG. 14B) and pH 2 (FIG. 14C).

As can be seen in FIGS. 14A-C, a sample of pure CLB showed considerable degradation at all tested pH values. CLB is least stable at pH 5, whereas at pH 2 the protonation of the mustard tertiary amine may partially prevent the formation of the aziridinium intermediate, reducing the reactivity of the mustard moiety. Considering the observed reactivity, the hydrolysis of CLB may become an important factor contributing to the loss of 9a before the cleavage of any of the amide or carbamate linkers.

Figure 15A:
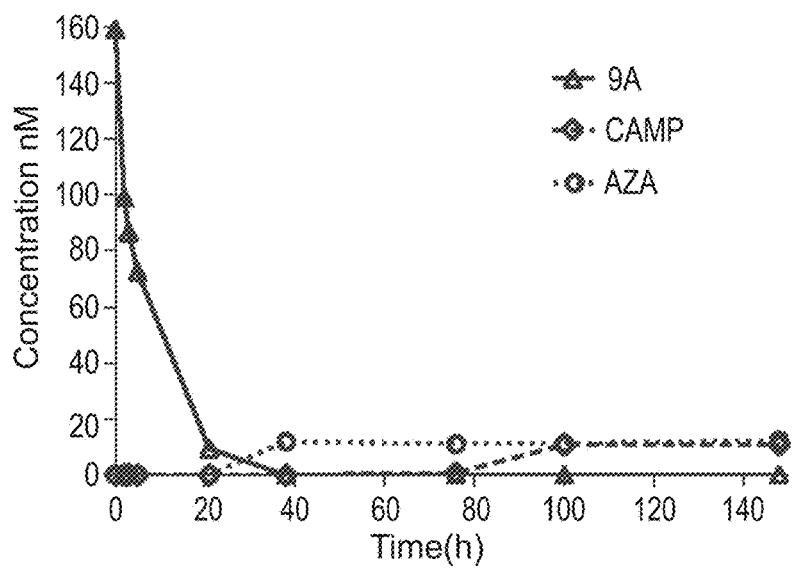
FIGS. 15A-C present the results of the chemo-stability tests of 9a at different pH values, pH 7.4 (FIG. 15A), pH 5 (FIG. 15B) and pH 2 (FIG. 15C)
Figure 15B:
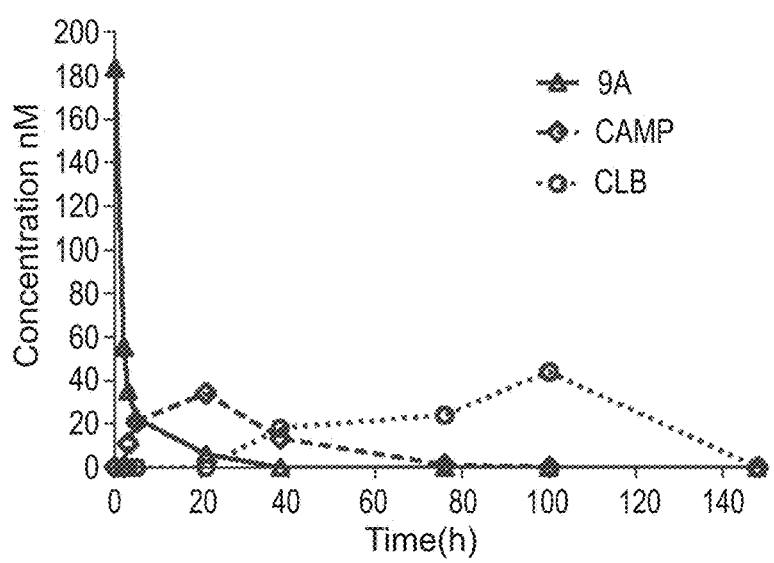
Figure 15C:
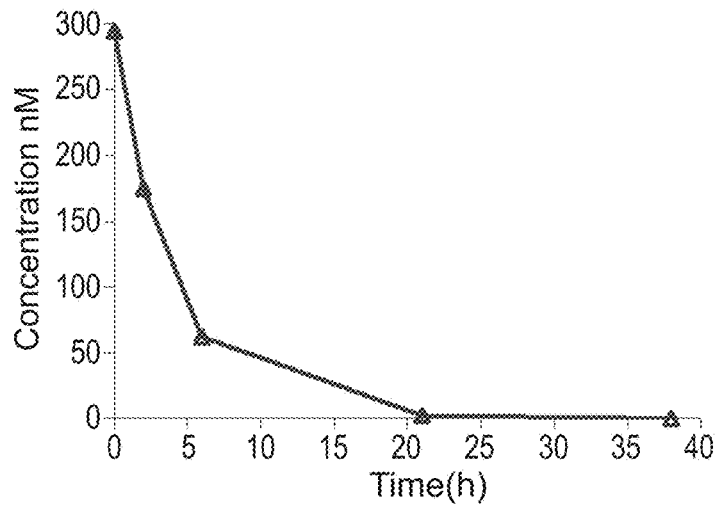

FIGS. 15A-C present the results of the chemo-stability tests of 9a at different pH values, pH 7.4 (FIG. 15A), pH 5 (FIG. 15B) and pH 2 (FIG. 15C).

As can be seen in FIGS. 15A-C, the degradation of 9a at pH 2 displayed a $t_{1/2}=2$ h while none of the three drugs appeared to be released intact or at all. At pH 5 the degradation rate of 9a was slightly faster, $t_{1/2}=1.5$ h and was accompanied by appearance of CAMP and CLB. The appearance of free AZA at pH 5 was not detected. CAMP is linked to the carrier through a carbamate from a tertiary alcohol. PDS released CAMP reaches its maximum concentration (34 nM) after 21 h and slowly decays completely into unidentified products within a period of 80 h. At pH 5 CLB could be first detected after 38 h and its concentration slowly rises up to (44 nM) after 100 h. At pH 7.4 AZA is, as expected, the first drug to be cleaved from the peptidyl carrier. The observed concentration of AZA starts to rise above base-line level after 20 h reaching a maximum concentration plateau (12 nM) at 40 h. A similar behavior was observed for CAMP but in this case the drug could be detected only after 75 h reaching its maximum concentration after 100 h. At this pH, free CLB was not detected probably due to the stability of the amide linker at physiological pH. The presumed reaction of an alcohol and the CLB N-mustard could partially account for the absence of free CLB and also for the low maximal concentration of AZA and CAMP. In order to test this assumption, equimolar amounts of CLB were incubated with AZA as well as CLB with CAMP at 37° C., for 48 h, at physiological pH. In both cases no reaction between the drugs could be observed, as judged by LC-MS analysis.

Figure 16:
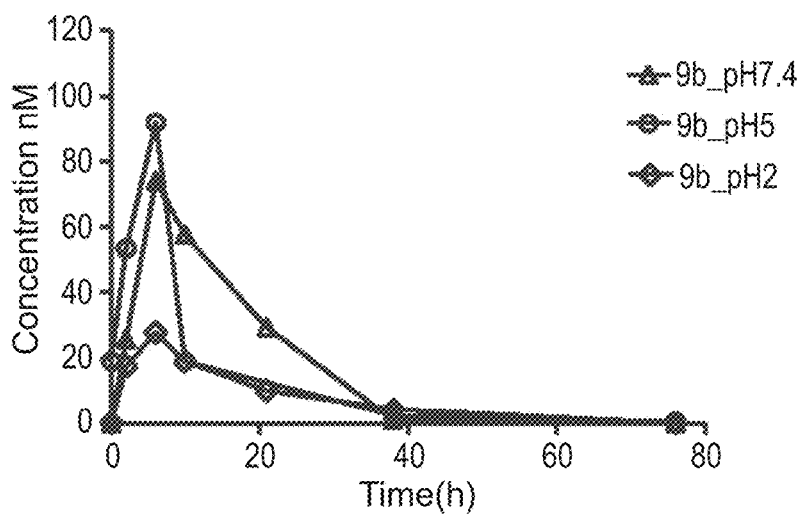
FIG. 16 presents the formation of the dihydroxy derivative 11 from 9a at different pH values.

FIG. 16 presents the formation of the dihydroxy derivative 11 from 9a at different pH values.

As can be seen in FIG. 16, the relatively fast disappearance of 9a at all tested pH values correlates well with the formation of the dihydroxy derivative of CLB (11). The dihydroxy derivative 11 was readily identified and followed by LC-MS. In all three pH cases the formation of 11 reaches it maximum at 5 h and then it slowly declines due to further reactions, leaving no traces after 40 h.

Bio-Stability Studies:

In order to get a biologically relevant picture of the release sequence of the different drugs, the bio-stability of 9a in murine liver homogenate (LH) was studied. Examination of the degradation rate of 9a, accompanied by cleavage of free drugs, was carried out following the LC-MS trace at different time intervals using premade authentic samples as reference signals.

Figure 17:
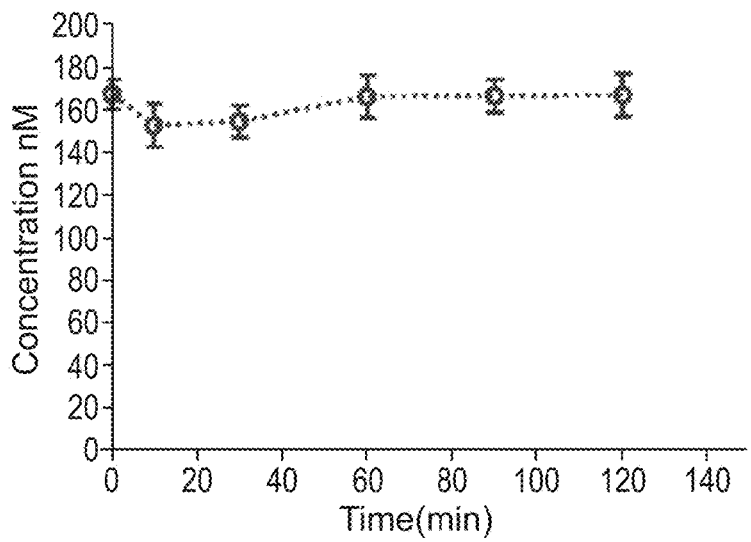
FIG. 17 presents the studies of the stability studies of the model compound 12 and its corresponding LH stability test.

FIG. 17 presents the studies of the stability studies of the model compound 12 and its corresponding LH stability test.

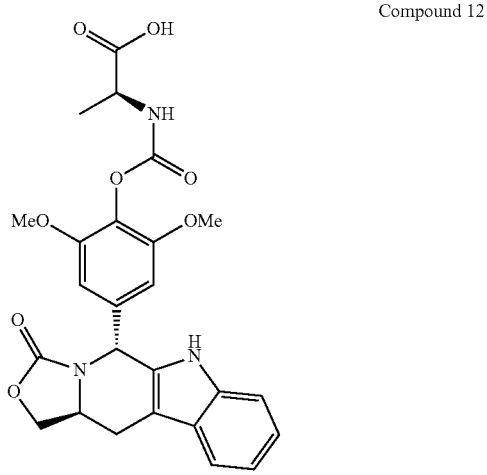 [SMILES: COc1cc([C@@H]2c3[nH]c4ccccc4c3C[C@H]3COC(=O)N32)cc(OC)c1OC(=O)N[C@@H](C)C(=O)O]

Compound 12

In sharp contrast to the buffered solutions at pH 7.4 previously used in the chemo-stability studies, which showed decomposition of the PDS without showing the release of any drug before 20 h, 9a in LH conditions resulted in the quick release of CLB and CAMP. The CLB amide bond is presumably cleaved by proteases present in the LH. The concentration of CLB gradually rises and reaches a steady state plateau after 80 min. CAMP possessing a biodegradable aliphatic carbamate moiety was also detected in the LH mixture. CAMP presents a slower onset rate relative to CLB, and reaches a lower concentration plateau only after 30 min. The presence of free AZA could not be detected. AZA is linked through a phenolic carbamate connection to the carrier and would a priori be expected to be cleaved at the fastest rate compared to the other two drugs. Failure to detect free AZA may be explained by its conversion into unknown derivatives, by its reaction with CLB, or by unforeseen LH inability to cleave the carbamate link. Under these conditions AZA itself appears to be stable and, as shown before, free AZA does not react with CLB. After ruling out the cross-reactivity of the drugs, the stability of carbamate link to AZA was re-examined. It is possible that the steric hindrance provided by the AZA methoxy groups and the secondary carbon of the carrier protects this bond from proteolytic cleavage. Incubation of a model compound Ala-AZA (12) in LH indicates that this link remains intact for at least 120 min.

It is noted that the degradation processes in LH were considerably faster compared to the measured background reactions in standard buffered solutions at the same temperature. The results presented here offer experimental support for the carbamate and amide functionalities as practical linkages for drug conjugation to our compact carrier.

Figure 18:
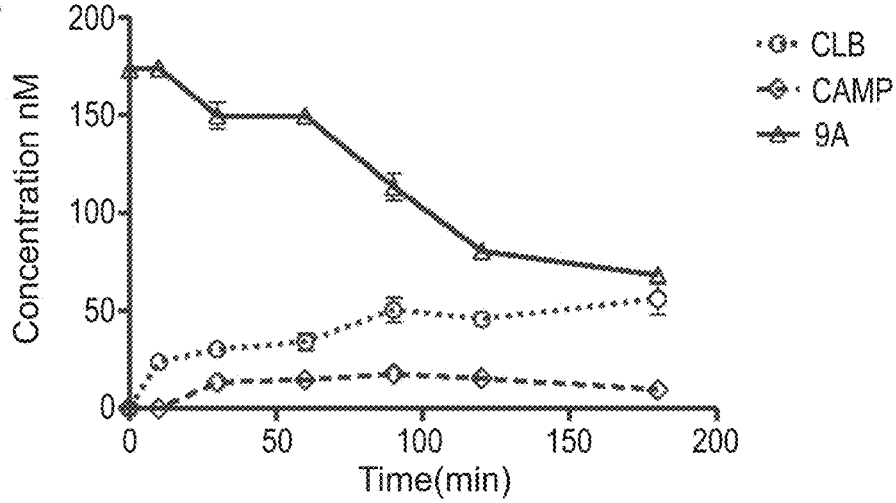
FIG. 18 presents the results of the bio-stability assay of 9a under liver homogenate conditions.

FIG. 18 presents the results of the bio-stability assay of 9a under liver homogenate conditions.

As can be seen in FIG. 18, the amide moiety was found to be fastest undergoing biodegradation under LH conditions. This observation may indicate an enhanced rate of drug release in the liver, potentially leading to unfavorable side effects on hepatocytes. The slow hydrolysis of the carbamate AZA link and the fast cleavage of the amide CLB connection could be tuned by optimizing the carrier-drug linkage chemistry as suggested above.

Cell Cytotoxicity:

The in vitro activity of 9a was determined on human embryonic kidney 293 (HEK293) cells and human prostate cancer TRAMP C2 cell lines in order to compare the cytotoxicity of 9a relative to the three selected free drugs. The HEK293 cell line was used as a model for healthy cells while TRAMP C2 was used as a model for prostate cancer tumor cells. The cytotoxicity of 9a was determined by measuring the mitochondrial enzyme activity of the different cell lines after incubation with the different substances for 24 h and 72 h. The viability factor (% of surviving cells) of the cell cultures was calculated relative to a control sample incubated with the vehicle only, considered as 100% viability. The experiment comprised two consecutive incubation steps. After the first incubation period cultures were washed and then exposed to a fresh medium containing different concentrations of the tested substances. The difference between these measurements was used for calculating the viability factor. The study was performed over a concentration range of 0.1-10 µM. No cytotoxic effect was exhibited by the free di Lys peptidyl carrier (data not shown).

Figure 19A:
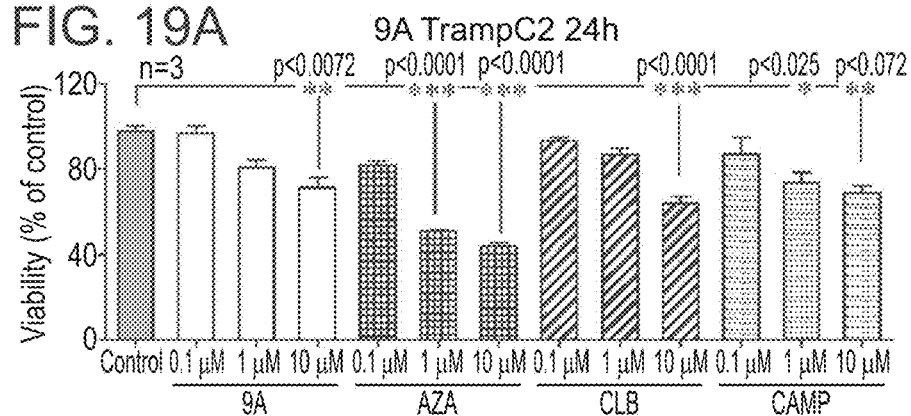
Figure 19B:
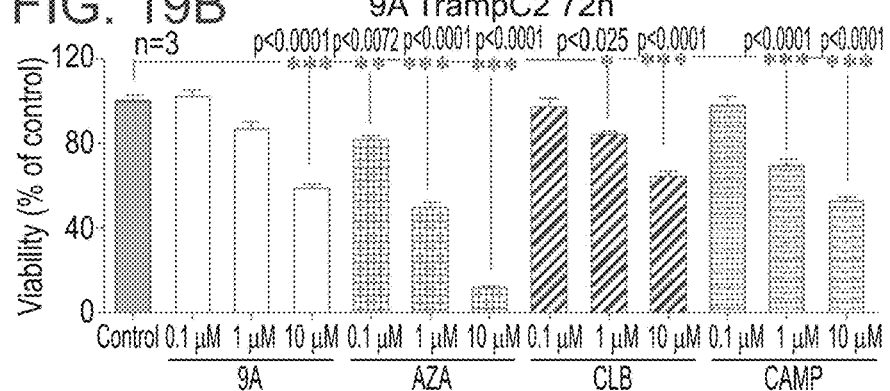
Figure 19C:
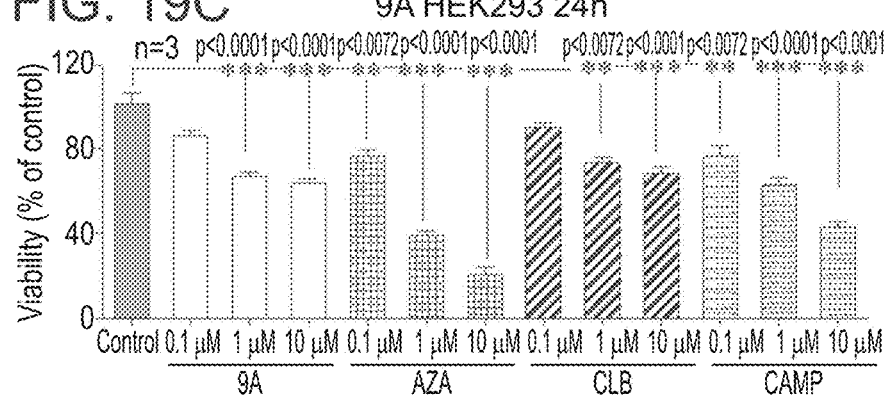
Figure 19D:
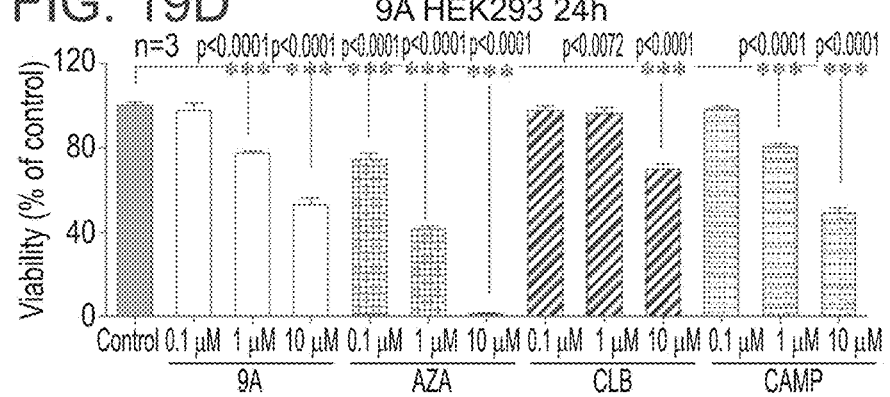

FIGS. 19A-D present the results of the viability assay (% surviving cells) of the cell cultures calculated relative to the control, 100% viability. The significances of the results are shown by the corresponding p values, wherein FIG. 19A and FIG. 19B show the viability of treated TRAMP C2 cells after 24 h and 72 h, respectively, and FIG. 19C and FIG. 19D show the viability of HEK 293 cells after 24 h and 72 h, respectively.

In addition to 9a, the toxic effects of the corresponding three drugs (CLB, AZA and CAMP) was also checked. After 72 h, all tested compounds showed no measurable activity at 0.1 μM and revealed well behaved dose response with considerable cytotoxic effects at the 10 μM range, clearly showing that the survival of both cell lines was significantly compromised under these conditions. AZA was found to be the most active drug leaving less than 10% surviving cells after 72 h incubation, in both cell lines (HEK293 and TRAMP C2). Not surprisingly, the parallel results between the two cell lines indicate a lack of selectivity which ought to be provided by the missing targeting sequence (selectivity studies are beyond the scope of this communication). It is apparent that the release of CLB and CAMP from the compact carrier is accountable for the observed cytotoxicity. Although unlikely, one could not rule out that 9a may exhibit some intrinsic cytotoxicity.

CONCLUSIONS

The development of an efficient SPOS conjugation strategy for cytotoxic drugs, including CLB, AZA, CAMP and AHMA, to a compact peptidyl carrier has been demonstrated hereinabove. The synthetic approach presented here also enables the use of other amino acids for the construction of compact carriers, which can potentially become fascinating molecular architectures exhibiting highly versatile and tunable drug linkage/release capabilities. Moreover, it has been shown that different semi-orthogonal and orthogonal combinations of protecting groups may also be applicable. Importantly, the reported facile SPOS is suitable for combinatorial synthesis of PDSs, with the potential to significantly accelerate the discovery of optimized targeted delivery and drug release systems. This concept can be expanded to carry a larger number of drugs by simply adding additional amino acid units to the carrier scaffold. The different kinetics of drug release from these peptidyl compact carriers remains a work in progress and will depend on the chemical nature of the used linkers. The carbamates and amide groups present good chemo-stability as drugs linkers. Judging by its stability at pH 7.4, CLB would not seem to be the most suitable choice to be used in a slow release prodrug approach mainly because the N-mustard reacts with water to produce harmless ethanolamine derivatives at a rate that could exceed the CLB cleavage from the peptidyl carrier. The LH bio-stability study demonstrates that enzymatic cleavage of the amide bond is more efficient than its background neutralizing hydrolysis reaction, as judged by the accumulation of CLB, which could be readily observed. In this case, early release of CLB may result in liver toxicity as an unwelcomed side effect.

It has been shown that incubation of 9a results in overall cytotoxic activity to both cancer and normal cell lines in a comparable level to the tested free drugs. Selectivity between the cell lines will be achieved once the peptidyl carrier is linked to a targeting sequence of choice.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of preparing a molecular structure represented by Formula I:

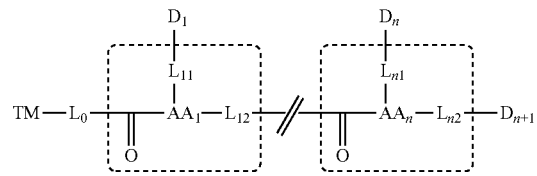

Formula I wherein:

$AA_1$ and $AA_n$ are each independently an amino acid residue;

n is an integer equal to or larger than 2 and denoting the number of said amino acid residues in the structure;

TM is a targeting moiety;

$L_0$, $L_{11}$, $L_{12}$, $L_{n1}$ and $L_{n2}$ are each independently a linking moiety;

$D_1$, $D_n$ and $D_{n+1}$ are each independently a bioactive agent or absent, provided that at least two of $D_1$, $D_n$ and $D_{n+1}$ are each independently a bioactive agent; and at least one bioactive agent of said $D_1$, $D_n$ and $D_{n+1}$ is different than at least one other bioactive agent of said $D_1$, $D_n$ and $D_{n+1}$, the process comprising:

binding a targeting moiety to a solid support;
linking said $AA_1$ to said targeting moiety;
optionally attaching said $D_1$ to said $AA_1$;
linking $AA_2$ to said $AA_1$;
optionally attaching $D_2$ to said $AA_2$;
optionally attaching $D_{2+1}$ to said $AA_2$;
when n is larger than 2, linking said $AA_n$ to said $AA_2$;
optionally attaching $D_n$ to said $AA_n$;
optionally attaching $D_{n+1}$ to said $AA_n$; and
detaching said targeting moiety from said solid support to thereby obtain the molecular structure.

2. The process of claim 1, wherein said linking and/or said attaching is effected via a functional group on said targeting moiety, or a functional group on a side chain of said amino acid, or on an alpha carbon of said amino acid.

3. The process of claim 2, wherein said linking and/or said attaching to said functional group further includes removing a protection group on said functional group.

* * * * *